(12) United States Patent
Fujimoto et al.

(10) Patent No.: US 12,310,597 B2
(45) Date of Patent: May 27, 2025

(54) CLIP CARTRIDGE, MEDICAL DEVICE, AND ATTACHMENT METHOD FOR MEDICAL DEVICE

(71) Applicant: OLYMPUS CORPORATION, Tokyo (JP)

(72) Inventors: Yasuyuki Fujimoto, Tokyo (JP); Kensuke Uesaka, Tokyo (JP); Ryu Yorita, Tokyo (JP); Yuta Muyari, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 885 days.

(21) Appl. No.: 17/386,207

(22) Filed: Jul. 27, 2021

(65) Prior Publication Data

US 2021/0353296 A1    Nov. 18, 2021

Related U.S. Application Data

(63) Continuation of application No. PCT/JP2019/003134, filed on Jan. 30, 2019.

(51) Int. Cl.
*A61B 17/128*    (2006.01)
*A61B 17/00*    (2006.01)
(Continued)

(52) U.S. Cl.
CPC .......... *A61B 17/128* (2013.01); *A61B 17/122* (2013.01); *A61B 90/03* (2016.02);
(Continued)

(58) Field of Classification Search
CPC ............ A61B 17/1222; A61B 17/1227; A61B 17/083; A61B 17/1285; A61B 2017/0053;
(Continued)

(56) References Cited

U.S. PATENT DOCUMENTS

2006/0155308 A1    7/2006  Griego
2011/0245855 A1    10/2011 Matsuoka et al.
2019/0046205 A1*   2/2019  Ikeda ................. A61B 17/1285

FOREIGN PATENT DOCUMENTS

EP    1818020 A1    8/2007
EP    3420975 A1    1/2019
(Continued)

OTHER PUBLICATIONS

Aug. 5, 2022 Extended European Search Report issued in European Patent Application No. 19913755.5.
(Continued)

*Primary Examiner* — Katherine H Schwiker
*Assistant Examiner* — Lauren Dubose
(74) *Attorney, Agent, or Firm* — Oliff PLC

(57) ABSTRACT

A clip cartridge includes a clip unit having a pressing tube, an arm member and a connection portion. The connection portion can transition between a protrusion configuration and an accommodation configuration. The clip cartridge also includes a housing that can accommodate the clip unit. The housing has a stopper that restricts movement of the connection portion and a release mechanism or a groove that permits movement of the connection portion. The stopper is able to restrict movement of the clip unit by contacting the arm member or the pressing tube.

20 Claims, 40 Drawing Sheets

(51) Int. Cl.
*A61B 17/122* (2006.01)
*A61B 90/00* (2016.01)
(52) U.S. Cl.
CPC ............... *A61B 2017/00477* (2013.01); *A61B 2090/034* (2016.02)
(58) Field of Classification Search
CPC .......... A61B 2017/00477; A61B 90/03; A61B 2090/034
See application file for complete search history.

(56) References Cited

FOREIGN PATENT DOCUMENTS

| | | |
|---|---|---|
| JP | 2007-507307 A | 3/2007 |
| JP | 2007-209775 A | 8/2007 |
| JP | 2008-526376 A | 7/2008 |
| JP | 2009-011852 A | 1/2009 |
| JP | 2009-268637 A | 11/2009 |
| JP | 2010-178897 A | 8/2010 |
| JP | 2013-085859 A | 5/2013 |
| JP | 2017-148182 A | 8/2017 |
| WO | 2005/032381 A2 | 4/2005 |
| WO | 2006-062019 A1 | 6/2006 |
| WO | 2018-011846 A1 | 1/2018 |

OTHER PUBLICATIONS

Aug. 9, 2022 Office Action issued in Japanese Patent Application No. 2020-569229.

Apr. 16, 2019 International Search Report issued in International Application No. PCT/JP2019/003134.

\* cited by examiner

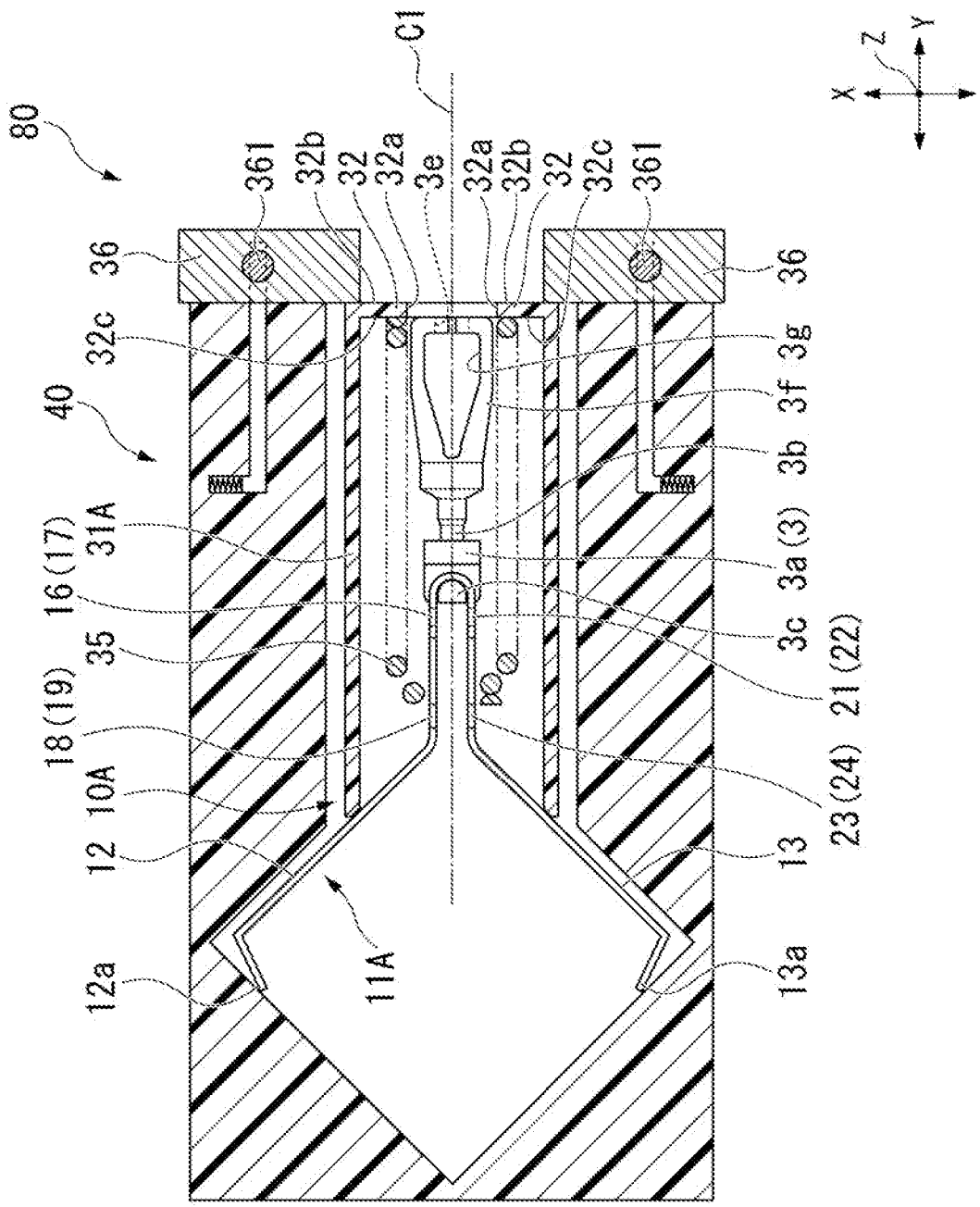

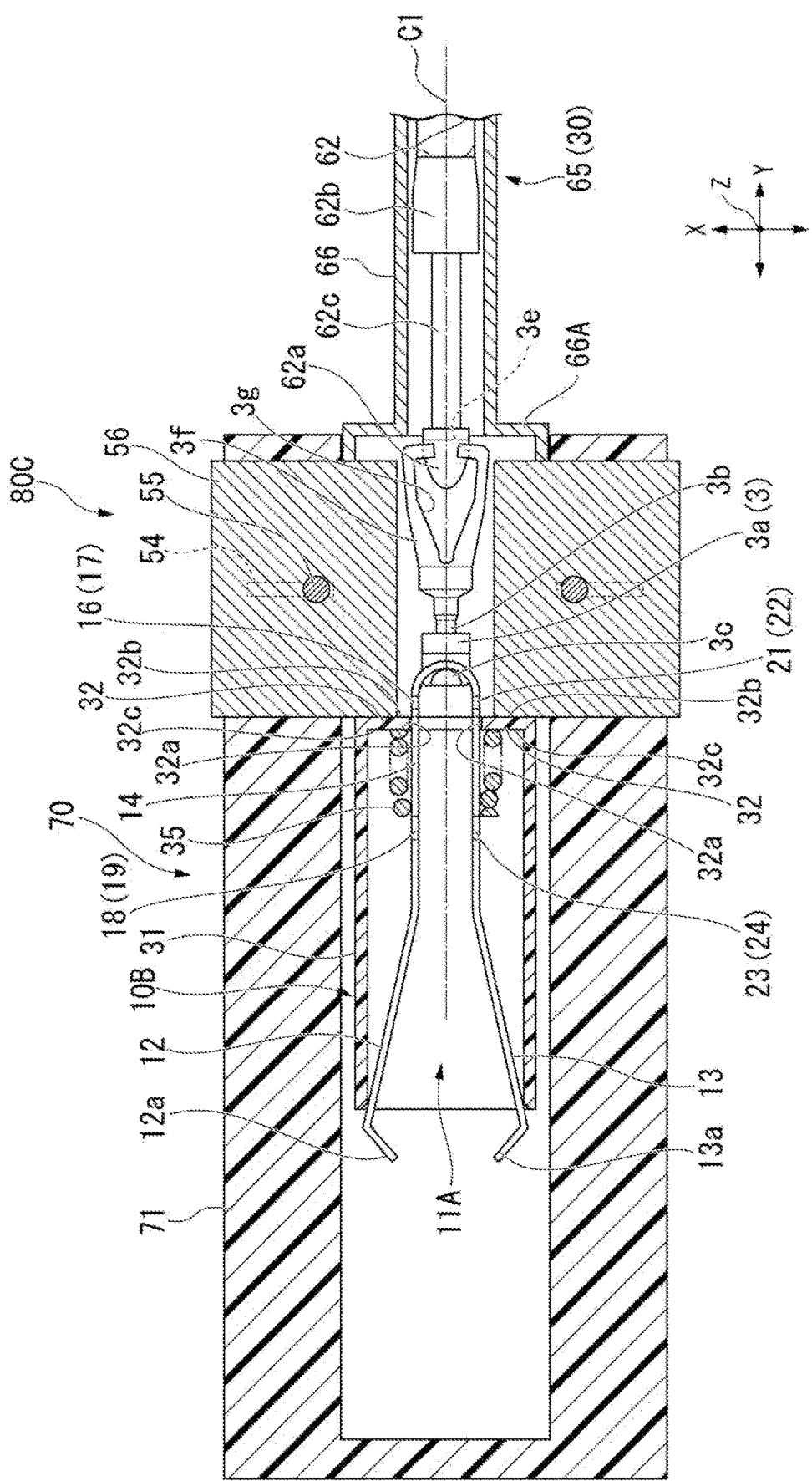

CLIP CARTRIDGE, MEDICAL DEVICE, AND ATTACHMENT METHOD FOR MEDICAL DEVICE

This application is a continuation application of PCT International Application No. PCT/JP2019/003134, filed on Jan. 30, 2019. The content of the PCT International Applications is incorporated herein by reference.

TECHNICAL FIELD

The present disclosure relates to a clip cartridge for accommodating a clip unit configured to treat a target tissue in a body, a medical device (more specifically, a ligating device used for ligating a tissue), and an attachment method for attaching the medical device.

BACKGROUND ART

Conventionally, an endoscope treatment device introduced into the body of a patient through a channel of the endoscope for ligating the openings formed in the tissues and the blood vessels in the body is disclosed in Japanese Unexamined Patent Application, First Publication No. 2009-011852.

The treatment instrument for an endoscope described in Japanese Unexamined Patent Application, First Publication No. 2009-011852 is configured by engaging a clip unit accommodated in a clip case and an operation wire inserted through an insertion portion of the endoscope with each other. According to the endoscope treatment device disclosed in Japanese Unexamined Patent Application, First Publication No. 2009-011852, the operation wire and the clip unit are engaged with each other by inserting a hook formed at the distal end side of the operation wire and in an arrowhead shape into a notch portion formed at the proximal end side of the clip unit. According to the endoscope treatment device disclosed in Japanese Unexamined Patent Application, First Publication No. 2009-011852, at the time when the operation wire and the clip unit are engaged with each other, the engagement portion of the hook and the connection member is positioned in the sheath of the insertion portion of the endoscope.

In the endoscope treatment device disclosed in Japanese Unexamined Patent Application, First Publication No. 2009-011852, a pair of arms of the clip unit are formed to be intersected with each other and part of the pair of arms are accommodated in the pressing tube. Accordingly, in the state in which the operation wire and the clip unit are engaged with each other, by the operation of retracting the operation wire to the proximal end side, the pair of arms are in contact with the pressing tube while the opening width between the pair of arms are increased once and then decreased to a degree suitable to tightly bind the target tissue.

According to the endoscope treatment device disclosed in Japanese Unexamined Patent Application, First Publication No. 2009-011852, the connection member disposed at the proximal end side of the clip unit has a small-diameter portion configured to be broken in a case in which a force exceeding the predetermined tensile strength is applied to the connection member. Accordingly, according to the endoscope treatment device disclosed in Japanese Unexamined Patent Application, First Publication No. 2009-011852, in the state in which the target tissue is grasped by the pair of arms of the clip unit, when the operator retracts the operation wire toward the proximal end side, the connection member is broken. In this manner, it is possible to indwell the clip unit grasping the target tissue in the body.

Generally, the medical device configured to perform treatment (ligation) with respect to the tissues inside the body is configured by connecting the treatment device (for example, the clip) inserted into the body and the applicator configured to adjust the position and the orientation of the treatment portion by the hand of the operator. When using the treatment device to perform treatment to the target tissues inside the body, for example, there is a case to further perform treatment to the new target tissues that are not discovered before the surgeon. At this time, for example, in the case of using the clip as the treatment device, it is necessary to exchange the plurality of clips so as to perform ligation to each of the plurality of target tissues. In other words, in the medical device for treating the target tissues inside the body, it is preferable to attach the new treatment device to the applicator, that is, it is preferable that the treatment device may be reloaded.

On the other hand, at the time of treating one target tissue inside the body, for example, in a case in which the tissue is unintentionally grasped by the clip used as the treatment device or in a case in which the state of grasping the target tissues is necessary to be adjusted, it is preferable to once release the grasping state of the tissues by the treatment device and then grasp the tissues again, that is, it is preferable to re-grasp the target tissue by the treatment device.

As disclosed above, in order to suitably perform treatment to the target tissues inside the body, it is preferable to achieve both goals of reloading the treatment portion and re-grasping the target tissues by the treatment device.

SUMMARY

According to an aspect of the present disclosure, a clip cartridge includes a clip unit having a pressing tube extending along a longitudinal axis; an arm member inserting into the pressing tube; and a connection portion provided in the arm member and configured to be capable to transition between a protrusion configuration protruding from the pressing tube and an accommodation configuration of being accommodated in the pressing tube; and a housing configured to be able to accommodate the clip unit, wherein the housing having: a stopper configured to restrict the transition of the connection portion from the protrusion configuration to the accommodation configuration; and a release mechanism configured to release the restriction by the stopper with respect to the transition of the connection portion from the protrusion configuration to the accommodation configuration, and wherein the stopper is configured to restrict the transition of the clip unit by coming in contact with the arm member or the pressing tube.

According to another aspect of the present disclosure, a medical device includes the clip according to the first aspect; and an applicator including an operation wire being engageable with the connecting portion, wherein the connection portion includes an engagement configuration in which the connection portion and the operation wire are engaged with each other and a release configuration in which the engagement configuration between the connection portion and the operation wire is released, wherein the connection portion is able to transition from the release configuration to the engagement configuration in the protrusion configuration, and wherein the transition of the connection portion from the release configuration to the engagement configuration in the accommodation configuration is restricted by an inner wall of the pressing tube.

According to a further aspect of the present disclosure, An attachment method for a medical device, wherein the medical device includes a clip unit having a pressing tube (31) extending along a longitudinal axis and an arm member (11) having a connection portion (3); a stopper (36) configured to restrict a transition of a position of the connection portion with respect to the pressing tube by the stopper coming in contact with the arm member or the pressing tube; a release mechanism (vertical groove 393) configured to release the restriction by the stopper with respect to the transition of the position of the connection portion; a housing (40) being able to accommodate the clip unit, and an applicator including an operation wire being engageable with the connection portion, the attachment method for a medical device to attach the clip unit to the applicator includes a step of moving the operation wire so as to engage the operation wire with the connection portion when the connection portion is at a position protruding from the pressing tube; and a step of moving the release mechanism to release the restriction with respect to the transition of the position of the connection portion and causing the connection portion to transition from the protruding position to a position where the connection portion is accommodated in the pressing tube in a state in which the connection portion is engaged with the operation wire.

BRIEF DESCRIPTION OF DRAWINGS

FIG. 15A is a partial cross-sectional planar view showing the state in which the clip unit is accommodated in the clip cartridge according to a modification of the present embodiment.

FIG. 29 is a view showing an operation of attaching the clip unit to the applicator according to the present embodiment.

DESCRIPTION OF EMBODIMENTS

First Embodiment

Hereinafter, configurations of a clip cartridge and a medical device according to a first embodiment of the present disclosure will be described with reference to FIG. 1 to FIG. 14.

A medical device 1 according to the present embodiment is used by being inserted into the body of a patient body through a channel formed in an endoscope (not shown). More specifically, the medical device 1 according to the present embodiment is a ligation device for ligating a target tissue in the body.

In this specification, the side on which the endoscope operation portion for the operator to operate the endoscope is located is defined as a proximal side, and the side on which the distal end portion of the endoscope inserted into the body is located is defined as a distal end side. More specifically, the proximal end side of the medical device 1 according to the present embodiment is defined as the side on which the endoscope operation portion is located when the medical device 1 is inserted into the channel formed in the endoscope. The distal end side of the medical device 1 is defined as the side where the distal end portion of the endoscope is located when the medical device 1 is inserted into the channel formed in the endoscope.

Figure 10:
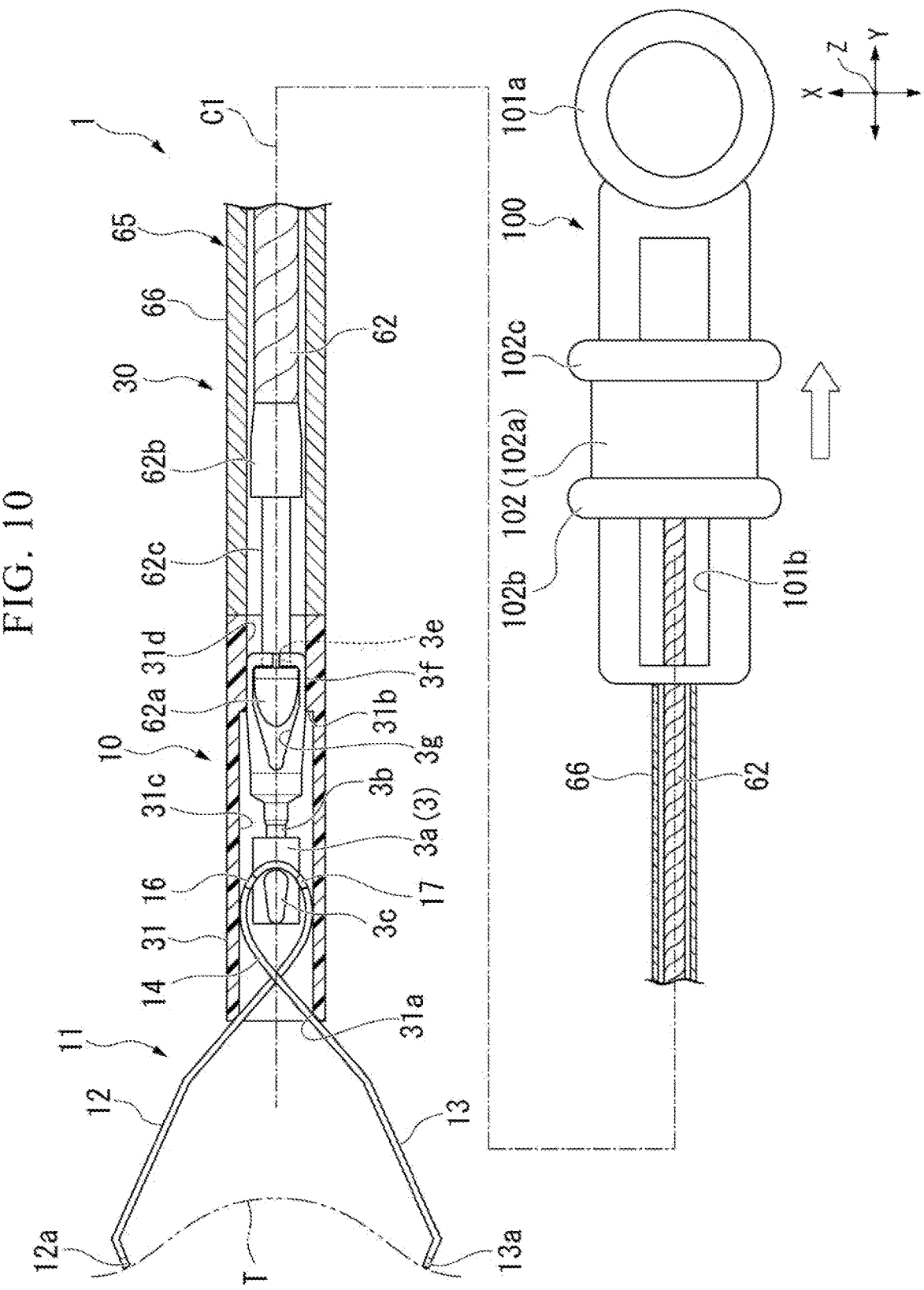
FIG. 10 is a view showing an operation of treating the target tissue using a medical device according to the present embodiment.
Figure 13:
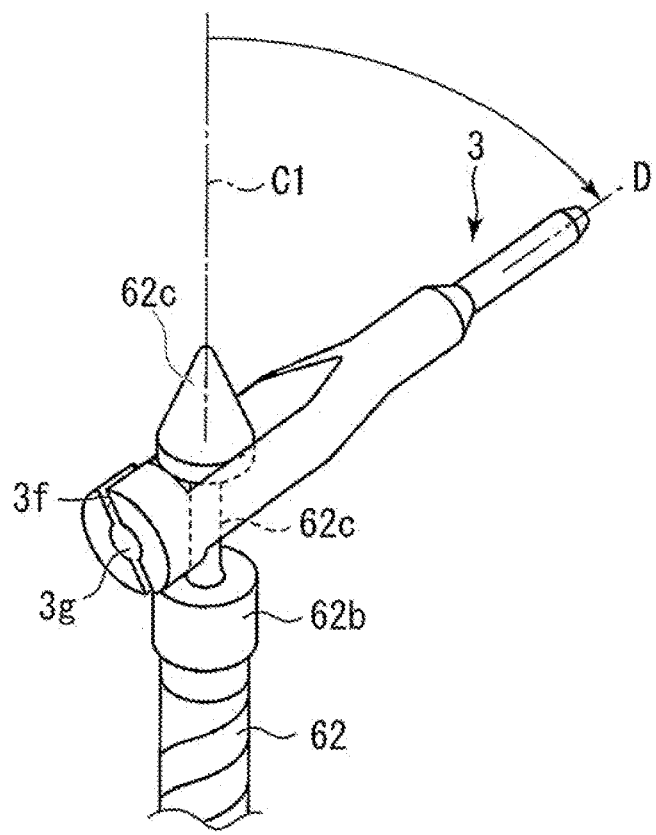
FIG. 13 is a perspective view schematically showing a configuration of a connection portion between the clip unit and the applicator in the medical device according to the present embodiment.
Figure 14:
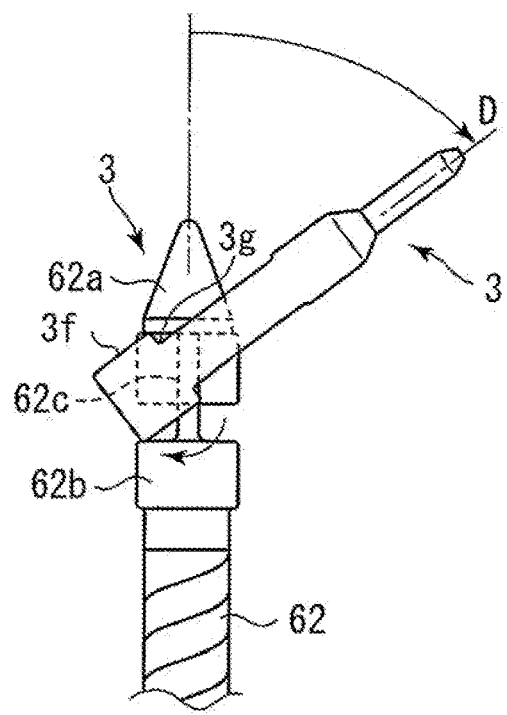
FIG. 14 is a side view schematically showing the configuration of the connection portion between the clip unit and the applicator in the medical device according to the present embodiment.

The medical device 1 according to the present embodiment is configured to include a clip unit (treatment portion) 10 provided on the distal end side and an applicator 30 (see FIG. 10). Hereinafter, for convenience of description, the clip unit 10 will be simply referred to as the clip 10. As shown in FIG. 13 and FIG. 14, the clip 10 is detachably connected to a distal end portion of an applicator 30 described later.

Hereinafter, the configuration of the clip 10 according to the present embodiment will be described with reference to FIG. 1 to FIG. 3.

Figure 1:
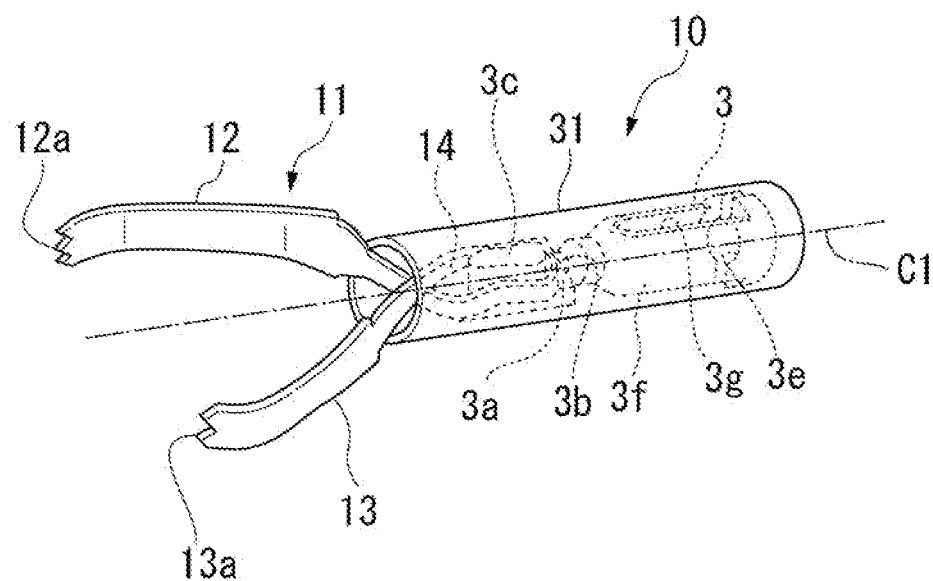
FIG. 1 is a perspective view schematically showing a configuration of a clip unit according to a first embodiment of the present disclosure.

FIG. 1 is a perspective view of a clip 10 according to the present embodiment. FIG. 2 is a perspective view of the arm member 11 of the clip 10 according to the present embodiment. FIG. 3 is a partial cross-sectional planar view of the clip 10 according to the present embodiment.

As shown in FIG. 1, the clip 10 according to the present embodiment includes an arm member 11, a pressing tube 31, and a connecting portion (first link) 3.

(Structure of Arm Member)

Figure 2:
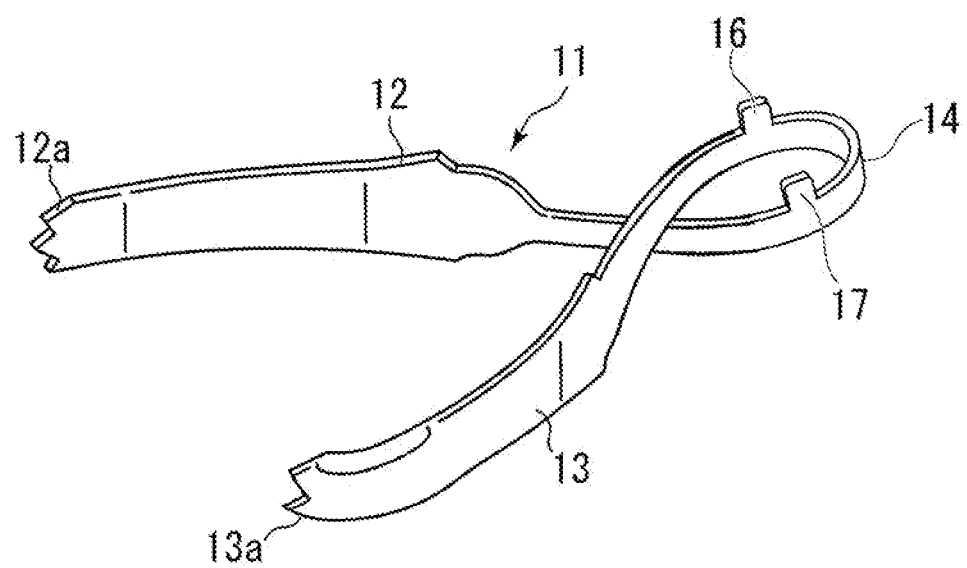
FIG. 2 is a perspective view schematically showing a configuration of an arm member in the clip unit according to the present embodiment.

As shown in FIG. 1 and FIG. 2, the arm member 11 includes a first arm 12, a second arm 13, and an intermediate portion 14. The first arm 12 and the second arm 13 extend from the proximal end side toward the distal end side and are arranged to be opposite to each other. The arm member 11 is configured by the first arm 12 and the second arm 13 intersecting with each other. As shown in FIG. 3, the first arm 12 and the second arm 13 may be formed at positions symmetrical with respect to the axis C1 of the pressing tube 31.

The intermediate portion 14 is located between the proximal end portion of the first arm 12 and the proximal end portion of the second arm 13. More specifically, as shown in FIG. 2, in the arm member 11, a portion located at more proximal end side than the intersection portion where the first arm 12 and the second arm 13 intersect is defined as the intermediate portion 14. The intermediate portion 14 is formed to have a loop shape that can be hooked by the distal end portion 3a of the connection portion 3 described later.

According to the present embodiment, the first arm 12 and the second arm 13 have an elastic restoring force such that in a natural state, the first arm 12 and the second arm 13 are separated from each other, and the distance therebetween increases along the direction from the proximal end side to the distal end side. In the present specification, the "natural state" refers to a state in which an external force is not applied to the arm member 11. A claw 12a extending toward the second arm 13 side is formed at the distal end portion of the first arm 12. A claw 13a extending toward the first arm 12 side is formed at the distal end portion of the second arm 13. The arm member 11 is biased by the elastic restoring force of the first arm 12 and the second arm 13 in a direction in which the loop shape formed in the intermediate portion 14 expands. Since the arm member 11 has the above-described configuration, for example, when the intermediate portion 14 retracts with respect to the pressing tube 31 in a state in which the intermediate portion 14 is in contact with an inner wall (internal circumferential surface) at more distal end side than a step portion 31b of the pressing tube described below, the distance between the first arm 12 and the second arm 13 may become larger by the intermediate portion 14 being pressed by the inner wall of the pressing tube 31 until the intersection portion where the first arm 12 and the second arm 13 intersect enters the pressing tube 31. Furthermore, when the first arm 12 and the second arm 13 are further moved toward the proximal end side with respect to the pressing tube 31 in a state where the intersection portion of the first arm 12 and the second arm 13 has entered the pressing tube 31, the first arm 12 and the second arm 13 are in contact with the tapered surface 31a formed in the opening at the distal end side of the pressing tube 31 and the distance therebetween decreases. That is, the first arm 12 and the second arm 13 may transition from an open configuration in which they are separated from each other to a closed configuration in which they approach each other to be close to each other.

The arm member 11 is formed, for example, by bending a metal material such as a plate spring material such as stainless steel to form the first arm 12 and the second arm 13, and then intersecting the first arm 12 and the second arm 13. The arm member 11 has this configuration such that the arm member 11 is slidable along the inner wall of the pressing tube 31 when moving inside the pressing tube 31 as described below.

A pair of first locked portions 16, 17 are formed on the first arm 12 and the second arm 13 of the arm member 11 respectively. More specifically, the pair of first locked portions 16, 17 protrude orthogonally to the longitudinal direction in which the first arm 12 and the second arm 13 of the arm member 11 extend. The pair of first locked portions 16, 17 may be formed at positions symmetrical with respect to the axis in the longitudinal direction in which the arm member 11 extends. By forming the pair of first locked portions 16, 17 of the clip 10, when the arm member 11 is retracted into the pressing tube 31, the arm member 11 comes into contact with the inner wall of the pressing tube 31 to restrict the movement of the arm member 11 with respect to the pressing tube 31. According to the present embodiment, the pair of first locked portions 16, 17 only have to be able to come in contact with the inner wall of the pressing tube 31 and the shape thereof is not particularly limited. However, in order to smoothly re-grasp the target tissue using the clip 10 described later, it is preferable that the pair of first locked portions 16, 17 be formed in a shape that does not bite into the inner wall of the pressing tube 31. For example, the pair of first locked portions 16, 17 may be formed in a circular arc shape or the like whose surface that abuts the inner wall of the pressing tube 31 is rounded.

(Structure of Pressing Tube)

According to the present embodiment, the pressing tube 31 is a pipe formed in a cylindrical shape having a longitudinal axis. For convenience of description, an example in which the longitudinal axis of the pressing tube 31 is the axis C1 will be described. The pressing tube 31 has an inner diameter such that the intermediate portion 14 of the arm member 11 is able to enter. That is, the pressing tube 31 is formed with a lumen into which the first arm 12 and the second arm 13 of the arm member 11 are enterable. At least part of the connection portion 3 described later can also enter the lumen formed in the pressing tube 31. According to the present embodiment, the pressing tube 31 is formed to have the outer diameter that is larger than the inner diameter of the sheath 66 of the insertion portion 65 described later.

Figure 8:
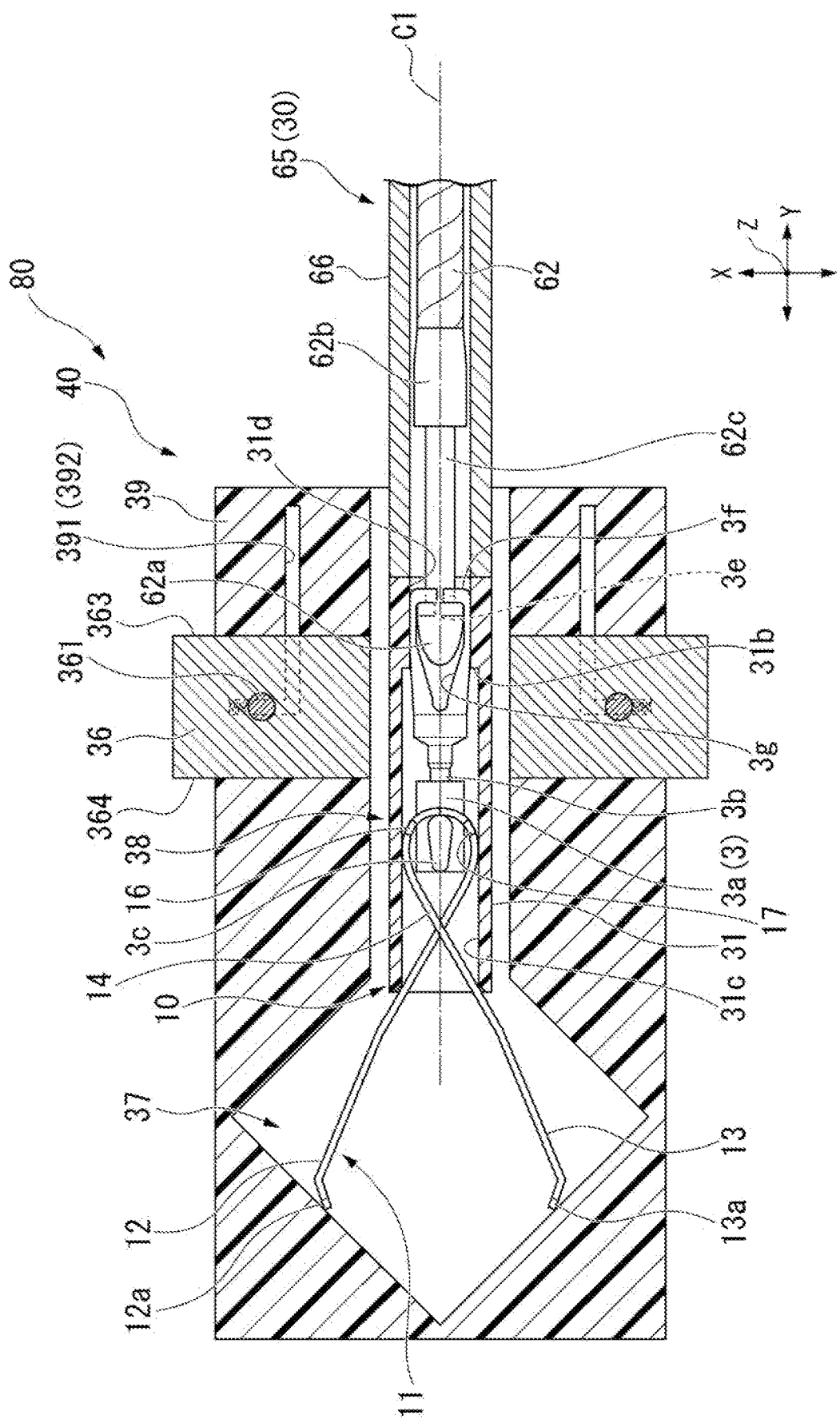
FIG. 8 is a view showing the operation of attaching the clip unit to an applicator according to the present embodiment.
Figure 9:
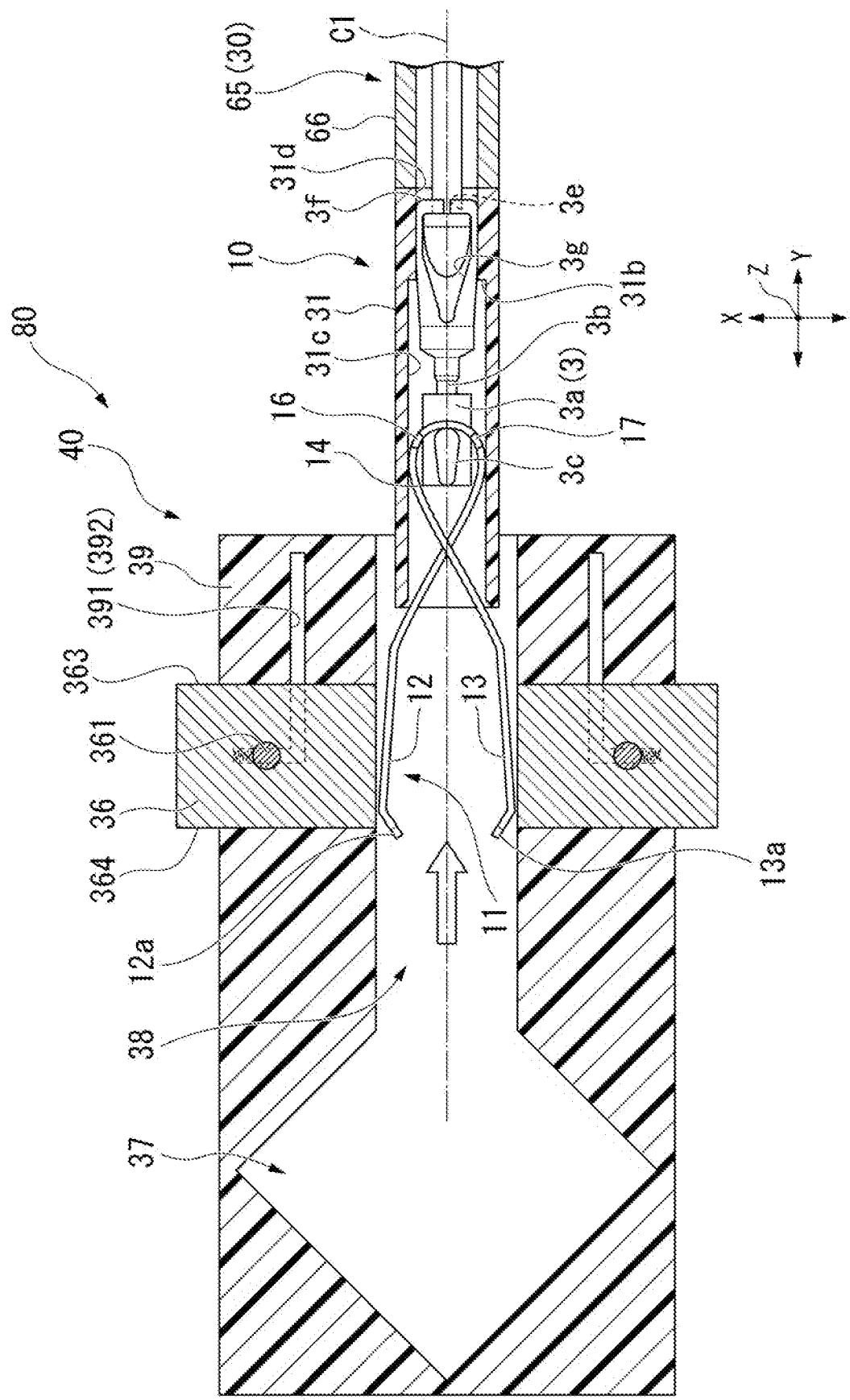
FIG. 9 is a view showing the operation of attaching the clip unit to an applicator according to the present embodiment.

According to the present embodiment, the pressing tube 31 is formed to have the inner diameter such that when the pressing tube 31 is positioned inside the pressing tube 31 with the hook 62a provided at the distal end of the operation wire 62 described later and the notch 3g of the connection portion 3 are engaged with each other, the connection portion 3 cannot rotate with respect to the hook 62a. More specifically, as shown in FIGS. 8 to 10, in the above-described state, the connection portion 3 only has to be formed to rotate with respect to the hook 62a in a direction intersecting the direction of axis C1 so as to release the engagement state between the hook 62a and the connection portion 3, and it is not necessary that the connection portion 3 does not rotate with respect to the hook 62a at all.

The members including the arm member 11 that configure the clip 10 are made of a material such as the cobalt chromium alloy, the titanium, or the stainless steel and the like. The clip 10 is also configured to be observable under MRI (Nuclear Magnetic Resonance Imaging).

For example, the arm member 11 is integrally formed by punching a plate material formed of a cobalt chrome alloy or the like in which the first arm 12 and the second arm 13, the intermediate portion 14, and the pair of first locked portions 16 and 17 are expanded in a planar shape.

Figure 3:
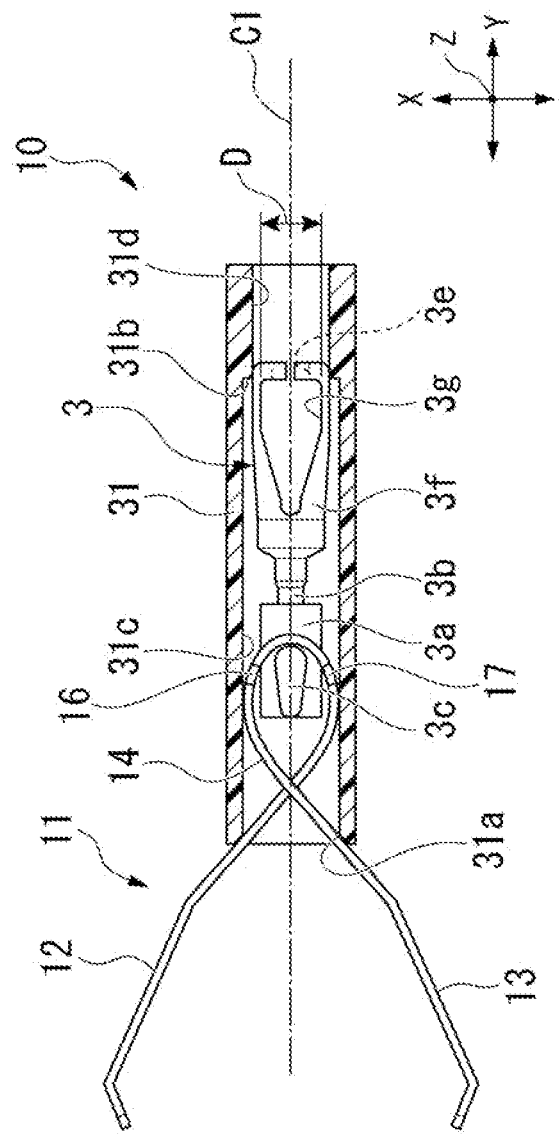
FIG. 3 is a partial cross-sectional planar view showing the clip unit according to the present embodiment.

As shown in FIG. 3, a tapered surface 31a is formed on the inner wall of the distal end portion of the pressing tube 31 over the entire circumference. The tapered surface 31a has a diameter increasing toward the distal end side. In the present embodiment, the pressing tube 31 may be integrally formed of a material such as the 64 titanium alloy (Ti-6AL-4V) or the cobalt chromium alloy and the like.

According to the present embodiment, a step portion 31b is formed which protrudes from the inner wall of the pressing tube 31 toward the inside of the pressing tube 31 in the radial direction. The pressing tube 31 is formed to have a large-diameter portion 31c located on the distal end side of the step portion 31b and a small-diameter portion 31d located on the proximal end side of the step portion 31b. That is, in the pressing tube 31, the large-diameter portion 31c has a larger inner diameter than the small-diameter portion 31d. The large-diameter portion 31c of the pressing tube 31 has an inner diameter such that the pair of first locked portions 16, 17 of the arm member 11 can advance and retract therein. Further, the small-diameter portion 31d of the pressing tube 31 has an inner diameter smaller than the width of the portion of the arm member 11 where the pair of first locked portions 16 and 17 are formed. Therefore, when the arm member 11 is retracted into the pressing tube 31 to be located at the proximal end side of the step portion 31b, the pair of first locked portions 16, 17 of the arm member 11 cut into the inner wall of the small-diameter portion 31d of the pressing tube 31 such that the movement of the arm member 11 toward the distal end side with respect to the pressing tube 31 is restricted.

(Structure of Connection Portion)

According to the present embodiment, the connection portion (first link) 3 is formed to have, as shown in FIGS. 1 and 3, a distal end portion 3a, a rod portion 3b, a hook portion 3c, a notch portion 3g, an insertion hole 3e, and a proximal end portion 3f. The connection portion 3 is formed by a method such as injection molding using a resin material having a predetermined strength.

As shown in FIG. 3, the connection portion 3 is configured to connect the arm member 11 of the clip 10 and an operation wire 62 described later. The distal end portion 3a of the connection portion 3 is configured to support the hook portion 3c for connecting the arm member 11, and the shape thereof is not particularly limited. The hook portion 3c is formed to protrude from the distal end portion 3a in a direction orthogonal to the direction of the longitudinal axis in which the connection portion 3 extends, and the hook portion 3c is hooked on a loop formed in the intermediate portion 14 of the arm member 11 so as to connect the arm member 11 to the connection portion 3.

As shown in FIG. 3, the proximal end portion 3f of the connection portion 3 is formed by bifurcating from the distal end side toward the proximal end side of the connection portion 3. In other words, the proximal end portion 3f is formed to have a pair of legs being apart from each other and an insertion hole 3e formed between the pair of legs. More specifically, as shown in FIG. 3, the insertion hole 3e is formed to have a width suitable for the arrowhead-shaped hook 62a (see FIG. 6) disposed at the distal end of the operation wire 62 described later to be inserted between the pair of legs of the proximal end portion 3f. Although details will be described later, when the hook 62a is inserted into the insertion hole 3e formed in the proximal end portion 3f, the outer circumferential surface of the hook 62a presses while contacting the inner circumferential surface of the insertion hole 3e such that the pair of legs of the proximal end portion 3f are elastically deformed outward in the radial direction with respect to the longitudinal axis direction of the connection portion 3 (see FIG. 6). Therefore, the hook 62a may pass through the insertion hole 3e and enter the notch portion 3g of the proximal end portion 3f.

As shown in FIG. 1 and FIG. 3, a notch portion 3g is formed by cutting a part of the proximal end portion 3f. The notch portion 3g has a width D that is large enough to accommodate the hook 62a when the hook 62a, which will be described later, enters the notch portion 3g through the insertion hole 3e formed in the proximal end portion 3f.

According to the present embodiment, the rod-shaped portion 3b connecting the distal end portion 3a and the proximal end portion 3f of the connection portion 3 is set to have lower strength than the other portions. Therefore, as will be described in detail later, when the clip 10 is indwelled, the connection portion 3 is broken at the rod-shaped portion 3b by retracting the operation wire 62 with a predetermined amount of force by the operator. At this time, the distal end portion 3a of the connection portion 3 is indwelled inside the body together with the clip 10, and the proximal portion 3f is removed from the body by the operation wire 62 while being engaged with the hook 62a (see FIG. 12).

According to the present embodiment, the connection portion 3 that engages with the intermediate portion 14 of the arm member 11 is biased toward the direction of moving to the distal end side by the elastic restoring force of the first arm 12 and the second arm 13 of the arm member 11. Further, since the connection portion 3 has the dimension capable of being accommodated in the pressing tube 31, as shown in FIG. 1, the connection portion 3 is in an accommodation configuration of being accommodated in the pressing tube 31 in a natural state where no external force is applied thereto. Further, as shown in FIG. 3, in this state, the outer diameter of the proximal end portion 3f is slightly smaller than the inner diameter of the small-diameter portion 31d of the pressing tube 31. Therefore, even if the operator inserts the hook 62a of the operation wire 62 into the insertion hole 3e, the pair of legs of the proximal end portion 3f cannot be elastically deformed radially outward with respect to the longitudinal axis direction of the connection portion 3. In other words, the clip 10 cannot be attached to the operation wire 62, which will be described later, when the connection portion 3 is in the accommodation configuration of being accommodated in the pressing tube 31.

Although not shown in the present embodiment, when the connection portion 3 is located in the large-diameter portion 31c of the pressing tube 31, a certain clearance between the outer circumferential surface of the proximal end portion 3f and the inner circumferential surface of the large-diameter portion 31c of the pressing tube 31 is available. Therefore, when the operator inserts the hook 62a of the operation wire 62 into the insertion hole 3e, the pair of legs of the proximal end portion 3f can be elastically deformed slightly outward in the radial direction with respect to the longitudinal axis direction of the connection portion 3. However, even in this state, the hook 62a cannot be inserted through the insertion hole 3e having a slightly enlarged diameter. In other words, in the present embodiment, the operator cannot attach the clip 10 to the operation wire 62 by inserting the hook 62a of the operation wire 62 into the notch portion 3g of the connection portion 3 in a state where the connection portion 3 is located inside the pressing tube 31.

Further, since the pressing tube 31 in the present embodiment has the above-described configuration, when the hook 62a is located inside the pressing tube 31 in a state of being engaged with the notch portion 3g, it is possible to prevent the hook 62a from being unintentionally slipped from the notch portion 3g.

For convenience of description, in the present embodiment, the connection portion 3, the pressing tube 31, and the operation portion 100 described below are arranged along the common longitudinal axis C1.

(Structure of Clip Cartridge)

Figure 4:
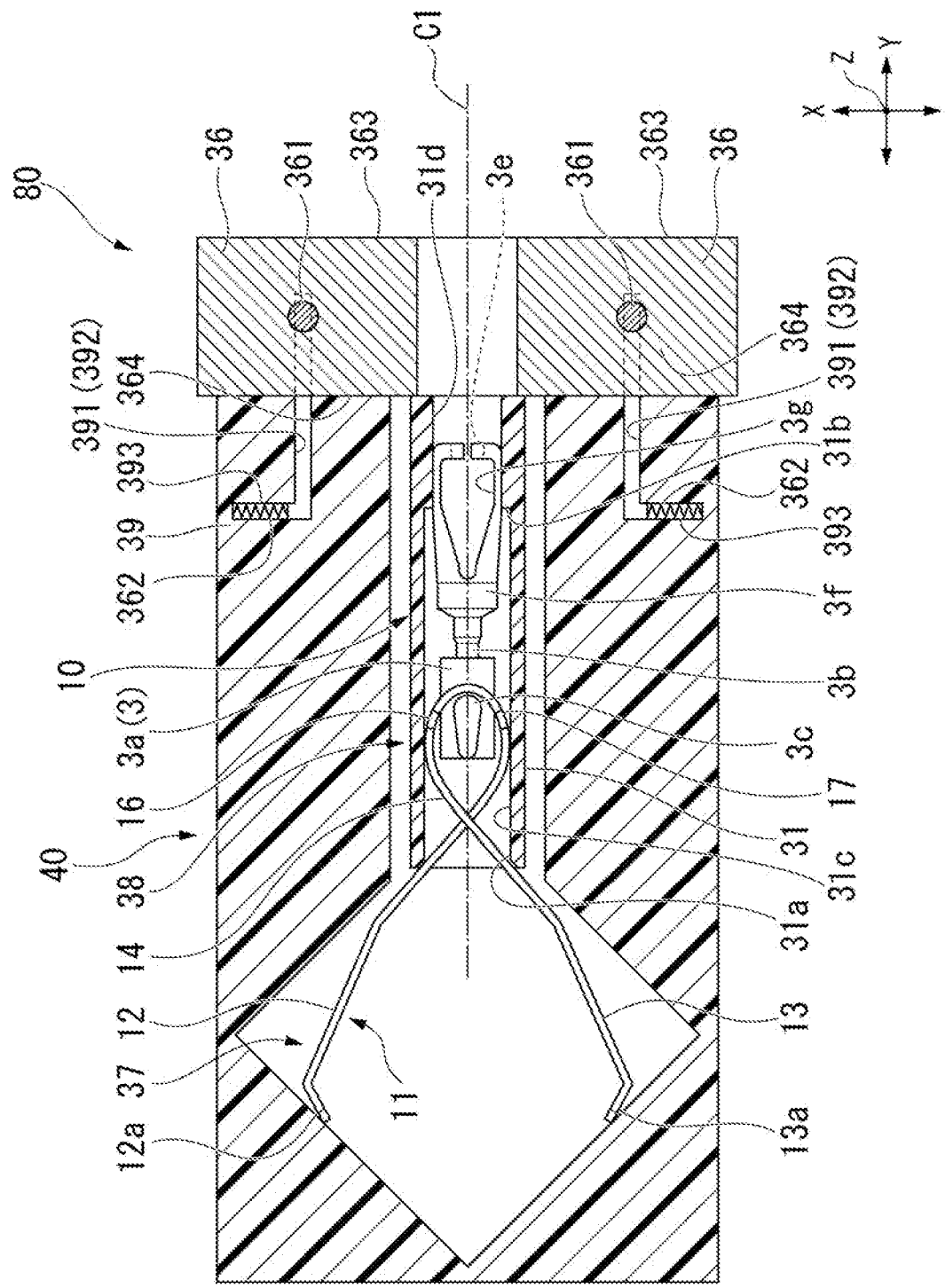
FIG. 4 is a partial cross-sectional planar view showing a state in which the clip unit is accommodated in the clip cartridge according to the present embodiment.

Next, the configuration of the clip cartridge 80 according to the present embodiment will be described. The clip cartridge 80 is configured to facilitate transportation during the process from the manufacturing of the clip 10 to the actual use thereof and to prevent the clip 10 from being contaminated by the external environment. As shown in FIG. 4, the clip cartridge 80 according to the present embodiment is configured to include the clip 10 and a housing 40 configured to be able to accommodate the clip 10 inside. FIG. 4 is a partial cross-sectional view showing a state where the clip 10 is accommodated inside the housing 40 in the clip cartridge 80 at the time of shipping.

According to the present embodiment, FIG. 4 is used only to show the positional relationship between the clip 10 and the housing 40. The housing 40 according to the present embodiment is not limited to the configuration shown in FIG. 4. The housing 40 according to the present embodiment only has to be able to suitably accommodate the clip 10 and has a size that is easy for the operator to grasp, and the shape thereof is not particularly limited. The housing 40 according to the present embodiment may employ the shape and configuration of the clip case described in Japanese Unexamined Patent Application, First Publication No. 2009-011852, for example.

As shown in FIG. 4, the housing 40 according to the present embodiment is formed to have the clip storage portion 37 and the lumen 38 along the longitudinal axis in the main body 39. In the clip storage portion 37, an inner cavity is formed in which the arm member 11 in the open configuration can be stored. The lumen 38 is provided at the proximal end side of the clip storage portion 37 and is configured to be able to accommodate the pressing tube 31. That is, in the housing 40, the clip storage portion 37 and the lumen 38 are formed along the axis Y direction shown in FIG. 4. In the clip storage portion 37, the dimension of the inner cavity in the direction of the axis X shown in FIG. 4 may be equal to or larger than the maximum value of the distance between the first arm 12 and the second arm 13 of the arm member 11 in the open configuration. The inner diameter of the lumen 38 in the direction of the axis X may be larger than the outer diameter of the pressing tube 31. The main body 39 of the housing 40 according to the present embodiment may be formed of, for example, various known resin materials that have a certain rigidity and are transparent.

Since the housing 40 according to the present embodiment has the above-described configuration, the housing 40 may be advanced and retracted along the longitudinal axis direction (the direction along the axis C1) while the clip 10 is accommodated in the housing 40.

As shown in FIG. 4, the housing 40 according to the present embodiment has two L-shaped grooves 391 formed on the proximal end side of the main body 39. More specifically, the groove 391 formed in the main body 39 includes a horizontal groove (first groove) 392 formed to extend along the longitudinal axis direction, and a vertical groove (second groove) 393 formed at more distal end side than the horizontal groove 392 and extending in the direction orthogonal to the horizontal groove 392. According to the present embodiment, the end surface of the horizontal groove 392 at the proximal end side is referred to as a proximal end surface of the groove 391, and the end surface of the vertical groove 393 on the outer side in the radial direction of the housing 40 is referred to as the distal end surface of the groove 391.

Figure 5:
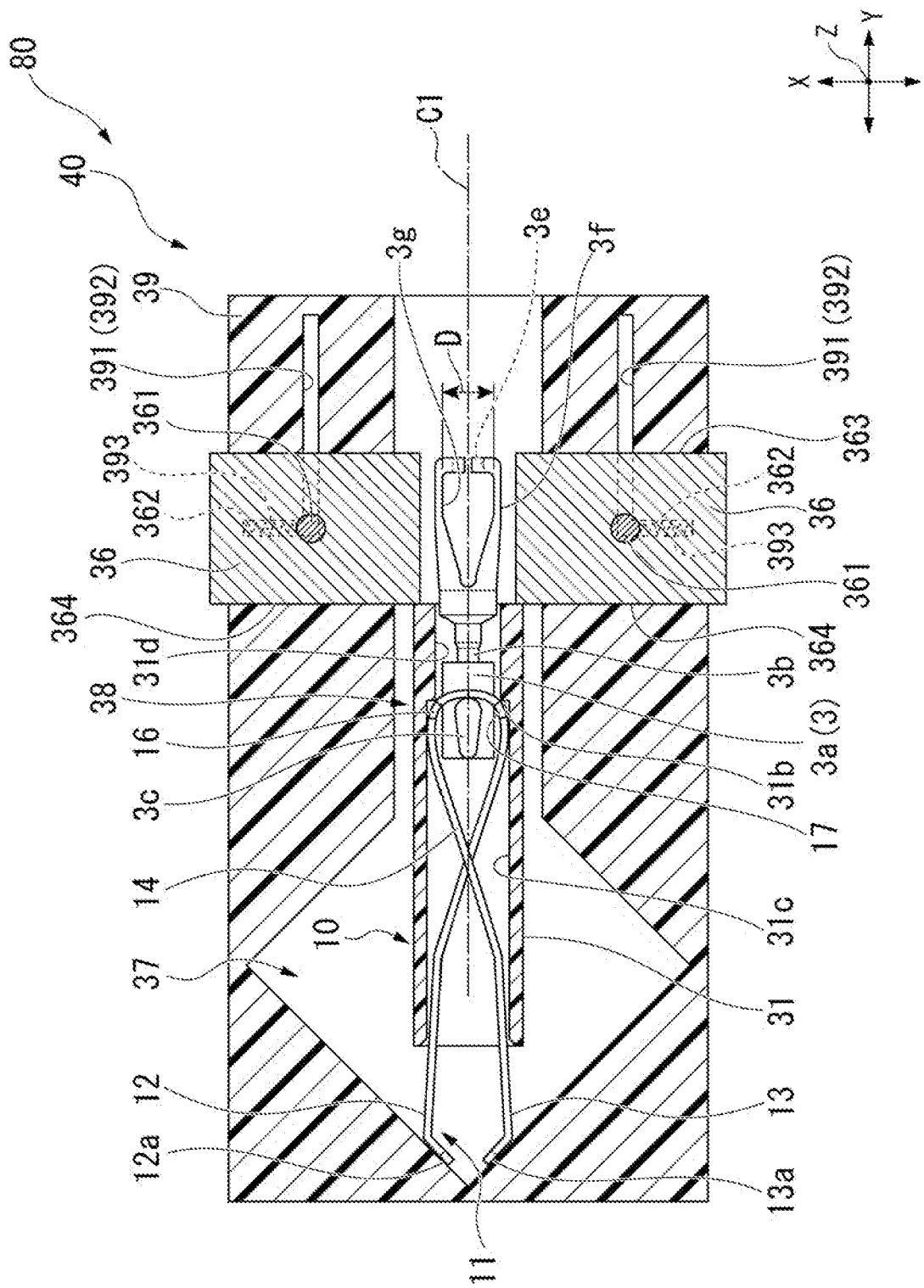
FIG. 5 is a view showing an operation of attaching the clip unit to an applicator according to the present embodiment.

As shown in FIG. 4, at the proximal end side of the housing 40, a pair of stoppers 36 being in contact with the proximal end surface of the pressing tube 31 are provided. The stopper 36 may be formed integrally with the pin 361 provided in the groove 391. Therefore, the pair of stoppers 36 may be moved along the groove 391 since the movement directions thereof are restricted by the pair of pins 361 respectively. Although details will be described later, as shown in FIG. 5, when the operator grasps the pair of stoppers 36 and moves the stoppers 36 toward the distal end side along the longitudinal axis direction of the housing 40 (direction along the axis C1), the pressing tube 31 may be moved to the distal end side in a state where the stopper 36 is in contact with the proximal end surface of the pressing tube 31.

As shown in FIG. 4, for convenience of description, an example in which the stopper 36 is formed to have a rectangular shape will be described according to the present embodiment; however, the present disclosure is not limited to this configuration. According to the present embodiment, the stopper 36 only has to be in contact with the proximal end surface of the pressing tube 31 so as to move the pressing tube 31 toward the distal end side, and the shape and the dimension thereof is not particularly limited.

As shown in FIG. 4, the distance between the pair of stoppers 36 in the direction of the axis X is larger than the inner diameter of the large-diameter portion 31c of the pressing tube 31. Although details will be described later, according to the present embodiment, in the state in which the pair of stoppers 36 are arranged in the horizontal groove 392, and the stoppers 36 are in contact with the proximal end surface of the pressing tube 31, the operator may move the pressing tube 31 toward the distal end side such that the operator may insert the hook 62a of the operation wire 62 into the notch portion 3g of the connection portion 3 when at least the proximal end portion 3f of the connection portion 3 protrudes from the opening at the proximal end side of the pressing tube 31 (see FIG. 6 and FIG. 7). In other words, the distance between the pair of stoppers 36 in the direction of the axis line X is equal to or larger than the maximum width of the proximal end portion 3f in the X direction when the hook 62a is inserted into the insertion hole 3e such that the pair of legs in the proximal end portion 3f are elastically deformed. Further, in the state in which the pair of stoppers 36 are arranged in the horizontal groove 392, the distance between the pair of stoppers 36 in the axis X direction is equal to or less than the outer diameter of the pressing tube 31.

According to the present embodiment, the pair of stoppers 36 and the pair of L-shaped grooves 391 may be provided in line symmetry with respect to the longitudinal axis C1 of the housing 40.

According to the present embodiment, the configuration in which the pair of stoppers 36 are provided in the main body 39 of the housing 40 is described as an example; however, the present disclosure is not limited to this configuration. With the configuration in which the housing 40 includes the pair of stoppers 36, it is possible to uniformly apply the force at the proximal end surface of the pressing tube 31 in the operation of moving the pressing tube 31 to the distal end side as described below so as to smoothly move the pressing tube 31 to the distal end side. According to the present embodiment, only one stopper 36 may be provided as long as the pressing tube 31 can be moved to the distal end side.

As shown in FIG. 4, an elastic member 362 is arranged in the vertical groove 393 formed in the main body 39. The elastic member 362 is fixed to the end surface positioned at the outer side of the vertical groove 393 in the axis X direction, that is, the outer side in the radial direction of the housing 40. The elastic member 362 is biased in the direction toward the longitudinal axis of the housing 40, that is, inward in the radial direction of the housing 40.

(Configuration of Applicator)

Subsequently, the configuration of the applicator 30 according to the present embodiment will be described with reference to FIG. 10. As shown in FIG. 10, the applicator 30 according to the present embodiment is configured to have an insertion portion 65 and an operation portion 100.

(Structure of Insertion Portion)

The insertion portion 65 of the applicator 30 includes a sheath 66 and an operation wire (wire) 62. The operation wire 62 is inserted into the sheath 66 so as to be advanceable and retractable therein. The operation wire 62 is configured to transmit the force with which the operator operates the operation portion 100 on the proximal end side (for example, the operation of pushing in the slider 102 and the operation of retracting the slider 102) to the clip 10.

The sheath 66 may be a coil sheath made of stainless steel such as SUS301 having high compression resistance strength. In this case, a coil formed by closely winding a wire (not shown) in the axial direction Y may be used as the sheath 66. The sheath 66 has flexibility and is strong against the compressive force in the axial direction Y.

According to the present embodiment, the sheath 66 is formed to have an inner diameter substantially equal to the inner diameter of the small-diameter portion 31d of the pressing tube 31 (see FIG. 8). Therefore, the clip 10 cannot be attached to the operation wire 62 inside the sheath 66. Further, when the hook 62a is located inside the sheath 66 in a state of being engaged with the notch portion 3g, it is possible to prevent the hook 62a from being unintentionally slipped from the notch portion 3g.

According to the present embodiment, the operation wire 62 is formed of, for example, a metal single wire or a twisted wire. The hook (second link) 62a formed in the arrowhead shape, a shaft portion 62c, and a fixation portion 62b are connected to the distal end side of the operation wire 62. The fixation portion 62b is a cylindrical member made of a metal material such as the stainless steel or the like, for example. The operation wire 62 is fixed to the fixation portion 62b by various known methods such as bonding, welding or the like. Further, the hook 62a and the fixation portion 62b are connected by the shaft portion 62c formed in a rod shape. Therefore, according to the present embodiment, the operation wire 62 is integrally formed with the hook 62a, the fixation portion 62b, and the shaft portion 62c. The hook 62a may advance and retract together with the operation wire 62 by the advancement and retraction operation of the operation wire 62.

Figure 7:
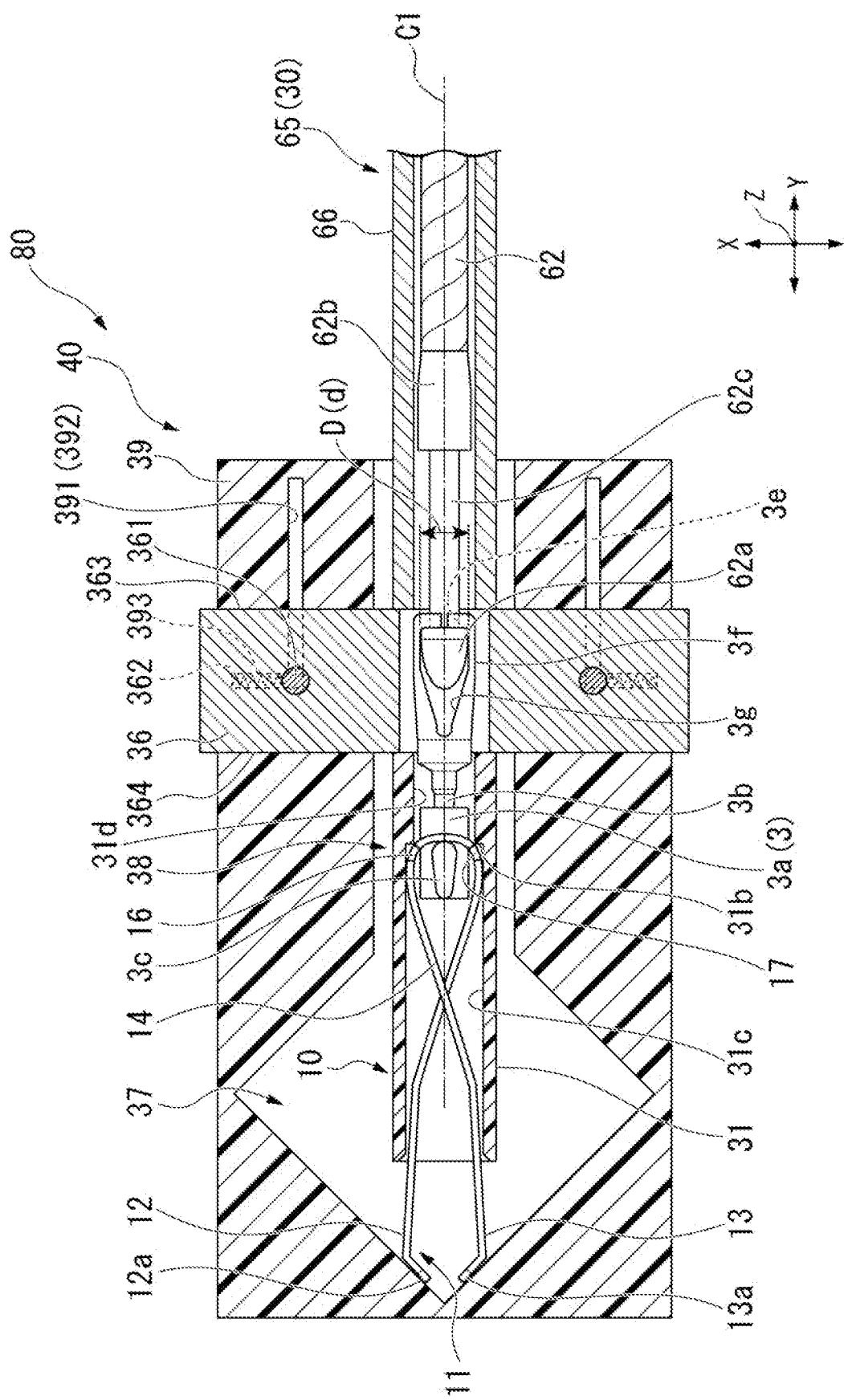
FIG. 7 is a view showing the operation of attaching the clip unit to an applicator according to the present embodiment.

The hook 62a is formed to have a conical shape. As shown in FIG. 10, the hook 62a has an outer circumferential surface formed in an inclined surface shape in which the outer diameter gradually decreases toward the distal end side. The outer diameter (width) d in the proximal end surface of the hook 62a is larger than the diameter of the insertion hole 3e formed in the proximal end portion 3f and equal to or less than the width D of the notch portion 3g in the state when the proximal end portion 3f of the connection portion 3 is not elastically deformed. As shown in FIG. 7, an example in which the width D of the notch portion 3g is substantially equal to the width d of the hook 62a is described according to the present embodiment; however, the present disclosure is not limited to this configuration.

(Structure of Operation Portion)

As shown in FIG. 10, the operation portion 100 includes an operation portion main body (handle) 101 and a slider 102.

The operation portion main body 101 is attached to the proximal end portion of the sheath 66. The operation portion main body 101 is formed in a rod shape extending in the axial direction Y, and has a finger hook portion 101a at the proximal end portion. The operation portion main body 101 is provided with a slit 101b extending in the axial direction Y.

The slider 102 is provided to be inserted into the operation portion main body 101. The slider 102 is slidable (advanceable and retractable) in the Y-axis direction with respect to the operation unit body 101. According to the present embodiment, when the slider 102 is advanced and retracted in the axial direction Y, the operation wire 62 and the hook 62a fixed to the distal end of the operation wire 62 are advanced and retracted. In the state in which the operation wire 62 and the connection portion 3 are connected, the arm member 11 of the clip 10 may advance or retract together with the operation wire 62 by the advancement or retraction of the operation wire 62. As a result, the pair of first arm 12 and second arm 13 of the arm member 11 may be opened or closed.

The slider 102 is formed in a cylindrical shape. On the outer circumferential surface of the slider 102, a recess 102a is formed over the entire circumference. On the slider 102, a flange portion 102b, the recess 102a, and a flange portion 102c are formed in this order from the distal end side to the proximal end side in the axial direction Y. The pair of flange portion 102b and flange portion 102c have elliptical shapes when viewed in the axial direction Y. As a result, the slider 102 can be easily grasped, and space can be saved when the operation portion 100 is packed.

The slider 102 engages with the slit 101b of the operation portion main body 101 to limit the movement range of the slider 102 in the axial direction Y with respect to the operation portion main body 101.

According to the present embodiment, the operation portion 100 may be adopted by using the configuration of the operation unit of various known endoscope treatment devices.

(Operation to Attach the Clip to the Applicator)

Hereinafter, with reference to FIGS. 4 to 9, an operation of attaching the clip 10 according to the present embodiment to the applicator 30 will be described as preparation before the treatment with respect to the target tissue in the body.

As shown in FIG. 4, the clip 10 is shipped while being accommodated in the housing 40. In this state, the pressing tube 31 including the connection portion 3 is located inside the lumen 38 of the housing 40.

As shown in FIG. 4, the clip 10 has an open configuration in which the first arm 12 and the second arm 13 of the arm member 11 protrude from the opening at the distal end side of the pressing tube 31 and separate from each other in the state in which the first arm 12 and the second arm 13 of the arm member 11 are in contact with the tapered surface 31a formed at the distal end side of the pressing tube 31. The first arm 12 and the second arm 13 of the arm member 11 are formed to have a pair of claws 12a and 13a provided on the distal end side are in contact (abut) with the inner wall of the clip storage portion of the housing 40. In the clip storage portion 37 of the housing 40 according to the present embodiment, an inner cavity having a size larger than the maximum value of the distance between the first arm 12 and the second arm 13 of the arm member 11 in the open configuration is formed such that it is impossible that the first arm 12 and the second arm 13 of the arm member 11 are bent by abutting the inner wall of the clip storage portion.

The intermediate portion 14 of the arm member 11 forms a loop shape so as to be hooked on the hook portion 3c of the connection portion 3. That is, the clip 10 and the connection portion 3 are engaged with each other by the intermediate portion 14 being hooked to the hook portion 3c. The elastic restoring force of the first arm 12 and the second arm 13 of the arm member 11 applies on the connection portion 3 such that the connection portion 3 is located inside the pressing tube 31.

As shown in FIG. 4, the pair of stoppers 36 are positioned at the proximal end side of the housing 40, and the respective distal end surfaces 364 are in contact (abut) with the proximal end surface of the pressing tube 31. The pressing tube 31 receives both the pressing force of the first arm 12 and the second arm 13 of the arm member 11 on the tapered surface 31a at the distal end side and the restriction force of the stopper 36 on the proximal end surface. The pressing force of the first arm 12 and the second arm 13 of the arm member 11 is applied to move the pressing tube 31 to the proximal end side. On the other hand, the movement of the pressing tube 31 toward the proximal end side is restricted by the restriction force on the distal end surface of the stopper 36. In other words, the pressing tube 31 is held at the position in the lumen 38 formed in the housing 40 since the two forces are simultaneously applied on the pressing tube 31 in a state in which the two forces are balanced.

Next, the operator grasps the pair of stoppers 36 and moves (slides) the pair of stoppers 36 together with the pin 361 toward the distal end side. As shown in FIG. 5, the pressing tube 31 moves to the distal end side together with the movement of the pair of stoppers 36 being in contact with the proximal end surface of the pressing tube 31 toward the distal end side. In this process, since the pair of stoppers 36 move in the horizontal groove 392 along the longitudinal axis direction of the housing 40, the distance between the pair of stoppers 36 is constant. As described above, since the distance between the pair of stoppers 36 is set to be larger than the width of the connection portion 3, the pressing tube 31 does not collide with the connection portion 3 in the process of moving to the distal end side.

As shown in FIG. 5, during the process in which the pressing tube moves toward the distal end side, the first arm 12 and the second arm 13 of the arm member 11 of the clip 10 come in contact with the tapered surface 31a and press the tapered surface 31a. The claws 12a and 13a of the first arm 12 and the second arm 13 of the arm member 11 move along the inner wall of the clip storage portion 37 of the housing 40 in the direction in which the distance therebetween decreases. As a result, the first arm 12 and the second arm 13 of the arm member 11 may transition from the above-mentioned open configuration to a closed configuration in which the first arm 12 and the second arm 13 of the arm member 11 are in contact with each other or the distance therebetween is substantially zero. At this time, the first arm 12 and the second arm 13 of the arm member 11 are partially inserted into the pressing tube 31.

When the operator moves the pair of stoppers 36 while holding them until the pin 361 reaches the distal end of the horizontal groove 392, the connection portion 3 protrudes from the opening at the proximal end side of the pressing tube 31, as shown in FIG. 5. According to the present embodiment, a state in which the connection portion 3 protrudes from the opening on the proximal end side of the pressing tube 31 is referred to as a protrusion configuration of the connection portion 3. In the protrusion configuration in which the connection portion 3 protrudes from the opening at the proximal end side of the pressing tube 31, at least part of the proximal end portion 3f including the notch portion 3g of the connection portion 3 protrudes from the opening at the proximal end side of the pressing tube 31; however, the present disclosure is not limited to this configuration. According to the present embodiment, at a position where part of the proximal end portion 3f of the connection portion 3 protrudes from the pressing tube 31, it is only necessary that the operation for connecting the hook 62a provided at the distal end of the operation wire 62 described later to the connection portion 3 may be performed. The protrusion amount of the connection portion 3 from the pressing tube 31 is not particularly limited.

Due to the elastic restoring force of the first arm 12 and the second arm 13 of the arm member 11 in the closed configuration, the pressing tube 31 tends to move to the proximal end side. However, since the proximal end surface of the pressing tube 31 is in contact with the distal end surfaces 364 of the pair of stoppers 36 and the position of the stopper 36 is held by the operator, the movement of the pressing tube 31 toward the proximal end side is restricted. In other words, the stopper 36 and the pressing tube 31 are in contact with each other such that the protrusion configuration of the connection portion 3 may be maintained. The stopper 36 may regulate the transition from the protrusion configuration in which the connection portion 3 protrudes from the pressing tube 31 to the accommodation configuration in which the connection portion 3 is accommodated in the pressing tube 31.

According to the present embodiment, the stopper 36 moves along the horizontal groove 392 in the L-shaped groove 391 such that the relative position between the connection portion 3 and the pressing tube 31 may be controlled.

According to the present embodiment, since the elastic member 362 that is biased radially inward of the housing 40 is provided in the vertical groove 393 of the L-shaped groove 391, unless the operator moves the pin 361, it is impossible for the pin 361 to move radially outward of the housing 40 in the vertical groove 393. Therefore, the state in which the stopper 36 and the pressing tube 31 are engaged is not released by the unintentionally movement of the pin 361.

According to the present embodiment, the state in which the stopper 36 is positioned at the distal end of the horizontal groove 392 is maintained by the operator grasping the stopper 36 is described as an example; however, the present disclosure is not limited to this configuration. By appropriately configuring the horizontal groove 392 and the pin 361, the position of the stopper 36 may be maintained even if the operator does not grasp the stopper 36.

For example, an elastically deformable restriction member (not shown) may be provided on the inner wall of the horizontal groove 392 at the distal end side to restrict the movement of the pin 361 toward the proximal end side. At this time, at the position where the restriction member is provided in the horizontal groove 392, a portion where the inner diameter of the horizontal groove 392 becomes smaller is formed. When the operator operates the stopper 36 to move the pin 361 toward the distal end side in the horizontal groove 392, the pin 361 and the restriction member abut against each other and the restriction member elastically deforms, the pin 361 may climb over the restriction member to reach the connection portion between the horizontal groove 392 and the vertical groove 393. However, it is impossible for the pin 361 to climb over the restriction member only by the press force for moving the pressing tube 31 and the stopper 36 that abuts the pressing tube 31 toward the proximal end side due to the elastic restoring force of the first arm 12 and the second arm 13 of the arm member 11.

Accordingly, even if the operator does not grasp the stopper 36, the state in which the stopper 36 is positioned at the distal end of the horizontal groove 392 may be maintained.

For example, the frictional force between the horizontal groove 392 and the pin 361 may be increased by appropriately selecting the materials for the inner wall of the horizontal groove 392 and the outer circumferential surface of the pin 361. In this case, due to the frictional force between the horizontal groove 392 and the pin 361, the pin 361 may be arranged at a desired position in the horizontal groove 392 unless the operator operates the stopper 36.

In the state in which the stopper 36 positioned at the distal end of the horizontal groove 392, the operator subsequently operates the operation portion 100 (see FIG. 10) of the applicator 30 to move the sheath 66 of the insertion portion 65 toward the connection portion 3 at the distal end side so as to cause the distal end surface of the sheath 66 to come in contact with the proximal end surface 363 of the stopper 36.

Figure 6:
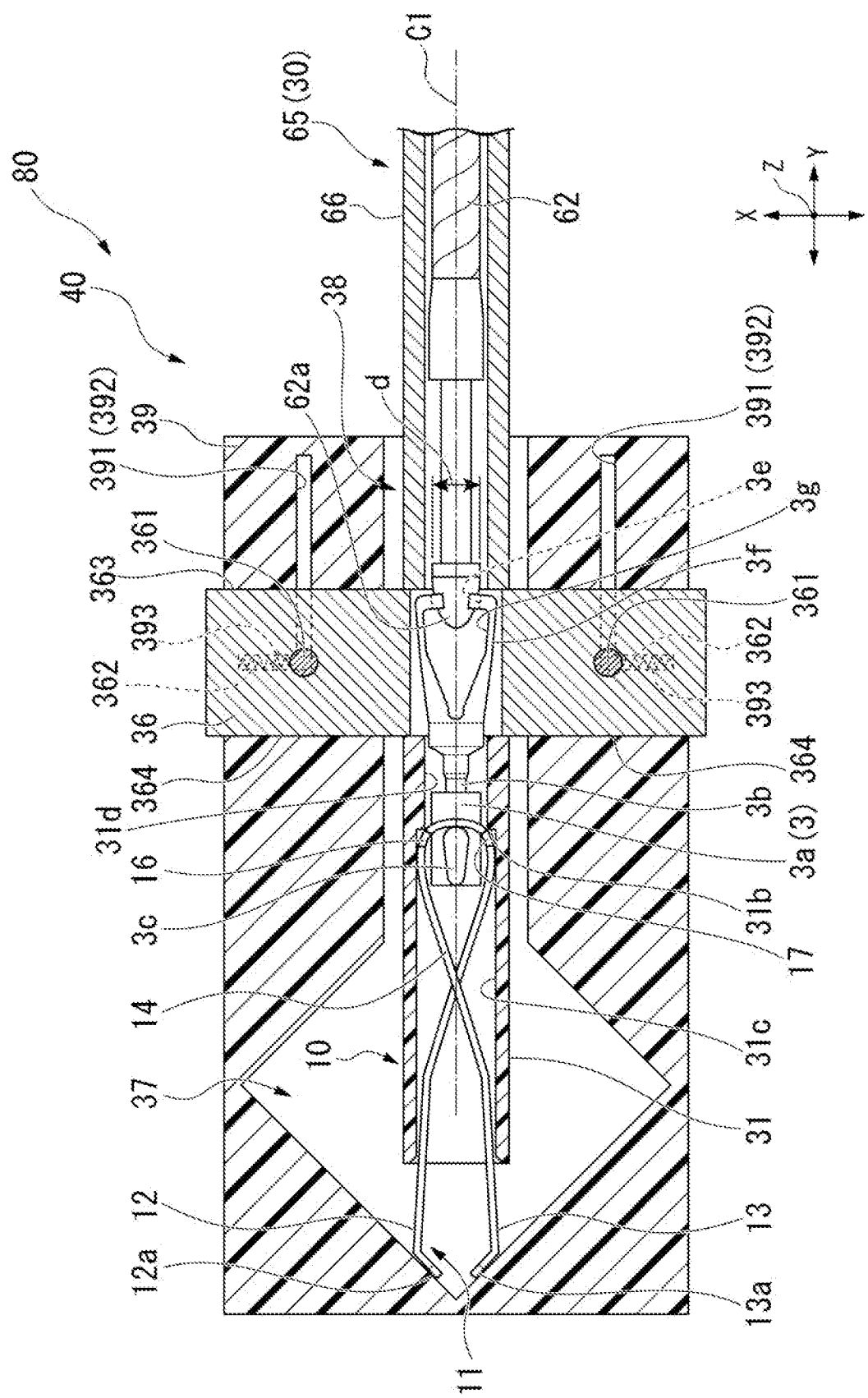
FIG. 6 is a view showing the operation of attaching the clip unit to an applicator according to the present embodiment.

In this state, as shown in FIG. 6, at least part of the proximal end portion 3f of the connection portion 3 protrudes from the pressing tube 31 toward the proximal end side to be located between the pair of stoppers 36. In this state, due to the operation of the operator to push the slider 102 toward the distal end side along the slit 101b of the operation portion main body 101, the hook 62a provided at the distal end of the operation wire 62 advances together with the operation wire 62, and the hook 62a comes in contact and presses the insertion hole 3e of the proximal end portion 3f of the connection portion 3.

When the operator pushes the slider 102 toward the distal end side, as shown in FIG. 6, the pair of legs of the proximal end portion 3f of the connection portion 3 are elastically deformed radially outward with respect to the longitudinal axis C1. The hook 62a passes through the insertion hole 3e formed in the proximal end portion 3f of the connection portion 3 and enters the notch portion 3g of the connection portion 3. As shown in FIG. 6, when the hook 62a passes through the insertion hole 3e of the connection portion 3, the pair of legs of the base end portion 3f of the connection portion 3 are elastically deformed such that the maximum value of the width of the proximal end portion 3f of the connection portion 3 in the X axis direction is equal to or less than the distance between the pair of stoppers 36 and larger than the inner diameter of the sheath 66 and the inner diameters of the large-diameter portion 31c and the small-diameter portion 31d of the pressing tube 31. In other words, according to the present embodiment, as shown in FIG. 6, the hook 62a of the operation wire 62 passes through the insertion hole 3e to be engaged with the notch portion 3g only in the state when the proximal end portion 3f of the connection portion 3 is not accommodated inside the pressing tube 31 and the sheath 66.

As a result, as shown in FIG. 7, the hook 62a is engaged with the notch 3g of the connection portion 3, and the connection portion where the connection portion 3 and the hook 62a are engaged with each other is located between the pair of stoppers 36, and the state of the hook 62a protruding from the opening at the proximal end side of the pressing tube 31 is maintained. That is, the protrusion configuration of the connection portion 3 is maintained.

More specifically, when the operator pushes the slider 102 to insert the hook 62a provided at the distal end of the operation wire 62 into the insertion hole 3e formed in the proximal end portion 3f of the connection portion 3, part of the proximal end portion 3f is elastically deformed. Therefore, the elastic restoring force generated by the partial elastic deformation of the proximal end portion 3f may be transmitted to the operator via the operation wire 62. When the hook 62a climbs over the proximal end portion 3f of the connection portion 3 and enters the notch portion 3g, the proximal end portion 3f is restored to the original shape and the hook 62a is accommodated in the notch portion 3g. By the operations described above, the operation wire 62 and the clip 10 are connected by the connection portion 3.

It is preferable for the operator since it is easy to confirm that the hook 62a enters the notch portion 3g of the connection portion 3 and engages with the notch portion 3g when the operator pushes the slider 102 until the slider 102 comes in contact with the distal end surface of the slit 101b during the operation of the operator pushing the slider 102. However, the present disclosure is not limited to this case.

That is, the hook 62a may enter the notch 3g of the connection portion 3 along the slit 101b and be engaged therewith before the slider 102 comes into contact with the distal end surface of the slit 101b. At this time, when the hook 62a enters the notch portion 3g of the connection portion 3 and is engaged therewith, the position of the slider 102 in the operation portion 100 within the slit 101b may be considered as the most advanced position of the slider 102. In this case, since the hook 62a is accommodated in the notch portion 3g, even if the operator pushes the slider 102, the resistance by the notch portion 3g may be transmitted to the operator, and the operator may similarly confirm that the connection portion 3 and the hook 62a are engaged with each other.

In the state in which the operation wire 62 and the clip 10 are connected to each other, the clip 10 may advance and retract together with the operation wire 62 by the operation to the slider 102 by the operator. More specifically, the first arm 12 and the second arm 13 of the arm member 11 of the clip 10 may advance and retract together with the operation wire 62 due to the advancement and the retraction of the operation wire 62. At this time, the first arm 12 and the second arm 13 of the arm member 11 may move relative to the pressing tube 31, as described below. As a result, the first arm 12 and the second arm 13 of the arm member 11 are in contact with the tapered surface 31a formed at the distal end side of the pressing tube 31, while the opening width of the arm member 11 therebetween is increased or decreased.

As shown in FIG. 7, in the state in which the operation wire 62 and the clip 10 are connected, the operator moves (slides) the pair of stoppers 36 outward in the radial direction of the housing 40 along the vertical groove 393. When the pair of stoppers 36 move outward in the radial direction of the housing 40 along the vertical groove 393, the engagement between the proximal end surface of the pressing tube 31 and the distal end surface 364 of the stopper 36 is released.

At this time, the pressing tube 31 moves to the proximal end side by the elastic restoring force of the first arm 12 and the second arm 13 of the arm member 11 of the clip 10. As described above, the pressing tube 31 according to the present embodiment is formed to have the outer diameter larger than the inner diameter of the sheath 66. Therefore, the pressing tube 31 moves toward the proximal end side until the proximal end surface comes in contact with the distal end surface of the sheath 66. As shown in FIG. 8, the connection portion where the connection portion 3 and the operation wire 62 are engaged with each other is accommodated in the pressing tube 31. In this state, even if the operator operates the slider 102 to advance or retract the operation wire 62, the connection portion between the connection portion 3 and the hook 62a is located inside the pressing tube 31 or the sheath 66, and thus it is impossible to unintentionally release the engagement between the connection portion 3 and the hook 62a.

In other words, when the operator moves the stopper 36 outward in the radial direction of the housing 40 along the vertical groove 393, the restriction to the transition of the connection portion 3 from the protrusion configuration to the accommodation configuration by the stopper 36. Accordingly, due to the elastic restoring force of the first arm 12 and the second arm 13 of the arm member 11, the pressing tube 31 moves toward the sheath 66 to the proximal end side and contacts the sheath 66. On the other hand, the connection portion 3 may transition from the protrusion configuration of protruding from the pressing tube 31 to the accommodation configuration of being accommodated in the pressing tube 31.

According to the present embodiment, the stopper 36 moves outward in the radial direction of the housing 40 along the vertical groove 393 of the L-shaped groove 391, so as to release the restriction with respect to the transition of the connection portion 3 from the protrusion configuration to the housing shape by the stopper 36. Accordingly, the vertical groove 393 in the L-shaped groove 391 according to the present embodiment is considered as a release mechanism for releasing the restriction to the transition of the connection portion 3 from the protrusion configuration to the accommodation configuration.

According to the present embodiment, in a case in which the elastic member 362 is not provided, it is possible that the pin 361 enters the vertical groove 393 and unintentionally moves in the direction toward the distal end surface of the L-shaped groove 391, that is, outward in the radial direction of the housing 40. When the pin 361 moves, the stopper 36 formed integrally with the pin 361 similarly moves outward in the radial direction of the housing 40. At this time, the state in which the stopper 36 and the pressing tube 31 are engaged with each other may be unintentionally released. As a result, the elastic restoring force of the arm member 11 of the clip 10 applies on the pressing tube 31 and moves the pressing tube 31 to the proximal end side.

According to the present embodiment, the elastic member 362 is configured to restrict the unintentional movement of the stopper 36 outward in the radial direction of the housing 49 together with the pin 361. Various known springs may be adopted as the elastic member 362. However, if the operator may grasp the stopper 36 so as to restrict the unintentional movement of the stopper 36, it is not necessary to provide the elastic member 362. That is, the elastic member 362 is not an essential configuration component of the housing 40.

Thereafter, the operator operates the operation portion main body 101 of the operation portion 100, and as shown in FIG. 9, the operation wire 62 and the clip 10 engaged with the operation wire 62 may be removed from the opening at the proximal end side of the lumen 38 of the housing 40. At this time, as shown in FIG. 9, the stopper 36 may be maintained to be at the position in the vertical groove 393 at the outside in the radial direction of the housing 40 by the operator, or the operator may release the stopper 36.

By the operations described above, the clip 10 according to the present embodiment is attached to the applicator 30. As shown in FIG. 9, in the state in which the clip 10 is attached to the applicator 30, the connection portion 3 is in the accommodation configuration of being accommodated in the pressing tube 31.

(Procedure with Medical Device)

Hereinafter, procedures for ligating the target tissue T using the medical device 1 according to the present embodiment having the above-described configuration will be described with reference to FIG. 10 to FIG. 12.

When the clip 10 is taken out from the housing 40 in the state of being attached to the applicator 30, the first arm 12 and the second arm 13 of the arm member 11 of the clip 10 are in the open configuration of separating from each other due to the elastic restoring force themselves, as shown in FIG. 10. In this state, the slider 102 is at the most advanced position in the slit 101b in the operation portion 100 at the proximal end side. Although it is not shown in figures, for example, the slider 102 may be at the position in contact with the distal end surface of the slit 101b, or the slider 102 may be at the position on the proximal end side in the slit 101b, which is separated from the distal end surface.

As described above, the elastic restoring force of the first arm 12 and the second arm 13 of the arm member 11 has an effect of moving the pressing tube 31 to the proximal end side. Therefore, as shown in FIG. 8 to FIG. 9, the proximal end surface of the pressing tube 31 is in contact with the distal end surface of the sheath 66. However, since the pressing tube 31 is formed to have the outer diameter larger than the inner diameter of the sheath 66, it is impossible for the pressing tube 31 to enter the sheath 66. In this state, the connection portion between the connection portion 3 and the hook 62a is located inside the pressing tube 31.

The operator inserts an endoscope (not shown) into the body of the patient. Subsequently, the operator inserts the medical device 1 from the proximal end portion of the channel of the endoscope, operate the medical device 1 to protrude from the distal end portion of the channel of the endoscope, and moves the medical device 1 to the vicinity of the target tissue T as the treatment target. In this process, the first arm 12 and the second arm 13 of the arm member 11 are maintained in the closed configuration by the operator continuing to grasp the slider 102.

The operator inserts the medical device 1 through the channel of the endoscope and moves the medical device 1 to the vicinity of the target tissue T so as to cause the arm member 11 to transition from the closed configuration to the open configuration.

At this time, the operator may operate the slider 102 to advance and retract so as to adjust the opening width between the first arm 12 and the second arm 13 of the arm member 11 to an optimum value in accordance with the size of the target tissue T. As a result, as shown in FIG. 10, the operator may adjust the opening width between the first arm 12 and the second arm 13 of the arm member 11 to the appropriate value with respect to the size of the target tissue T.

More specifically, according to the present embodiment, the operator operates the slider 102 of the operation portion 100 to advance and retract such that the clip 10 advances and retracts together with the operation wire 62. That is, the first arm 12 and the second arm 13 of the arm member 11 of the clip 10 may move relative to the pressing tube 31 together with the advancement and retraction of the operation wire 62. As a result, the first arm 12 and the second arm 13 of the arm member 11 are in contact with the tapered surface 31a provided on the distal end side of the pressing tube 31, while the opening width of the arm member 11 therebetween is increased or decreased. For example, as shown in FIG. 10, when the operator retracts the slider 102 toward the proximal end side, in the arm member 11, the intermediate portion 14 (the portion at more proximal end side than the location where the first arm 12 and the second arm 13 intersect) enters the large-diameter portion 31c of the pressing tube 31, and the first arm 12 and the second arm 13 are separated from each other in the radial direction of the arm member 11. As a result, the operator may adjust the opening width of the arm member 11 in accordance with the size of the target tissue T.

Next, the operator operates an endoscope (not shown) to adjust the orientation and posture of the arm member 11 of the clip 10 and then presses the arm member 11 toward the target tissue T. By such operations, the target tissue T is located between the first arm 12 and the second arm 13 of the arm member 11 in the open configuration. When the operator confirms that the target tissue T is located between the first arm 12 and the second arm 13, the operator may operate the endoscope to grasp the target tissue with the first arm 12 and the second arm 13 of the arm member 11.

When the operator can confirm that the target tissue T is located between the first arm 12 and the second arm 13, the operator grasps the operation portion main body 101 and moves the slider 102 to the proximal end side, as shown in FIG. 10. At this time, the operation wire 62, the hook 62a and the connection portion 3 which are engaged with each other, and the first arm 12 and the second arm 13 move together toward the proximal end side. The first arm 12 and the second arm 13 come in contact with the tapered surface 31a provided on the distal end side of the pressing tube 31, while the first arm 12 is elastically deformed toward the second arm 13 side and the second arm 13 is elastically deformed toward the first arm 12 side. As a result, the claw 12a provided on the distal end side of the first arm 12 and the claw 13A provided on the distal end side of the second arm 13 approach each other. In other words, the opening width of the arm member 11 between the first arm 12 and the second arm 13 is decreased, and the arm member 11 transitions from the open configuration to the closed configuration.

Figure 11:
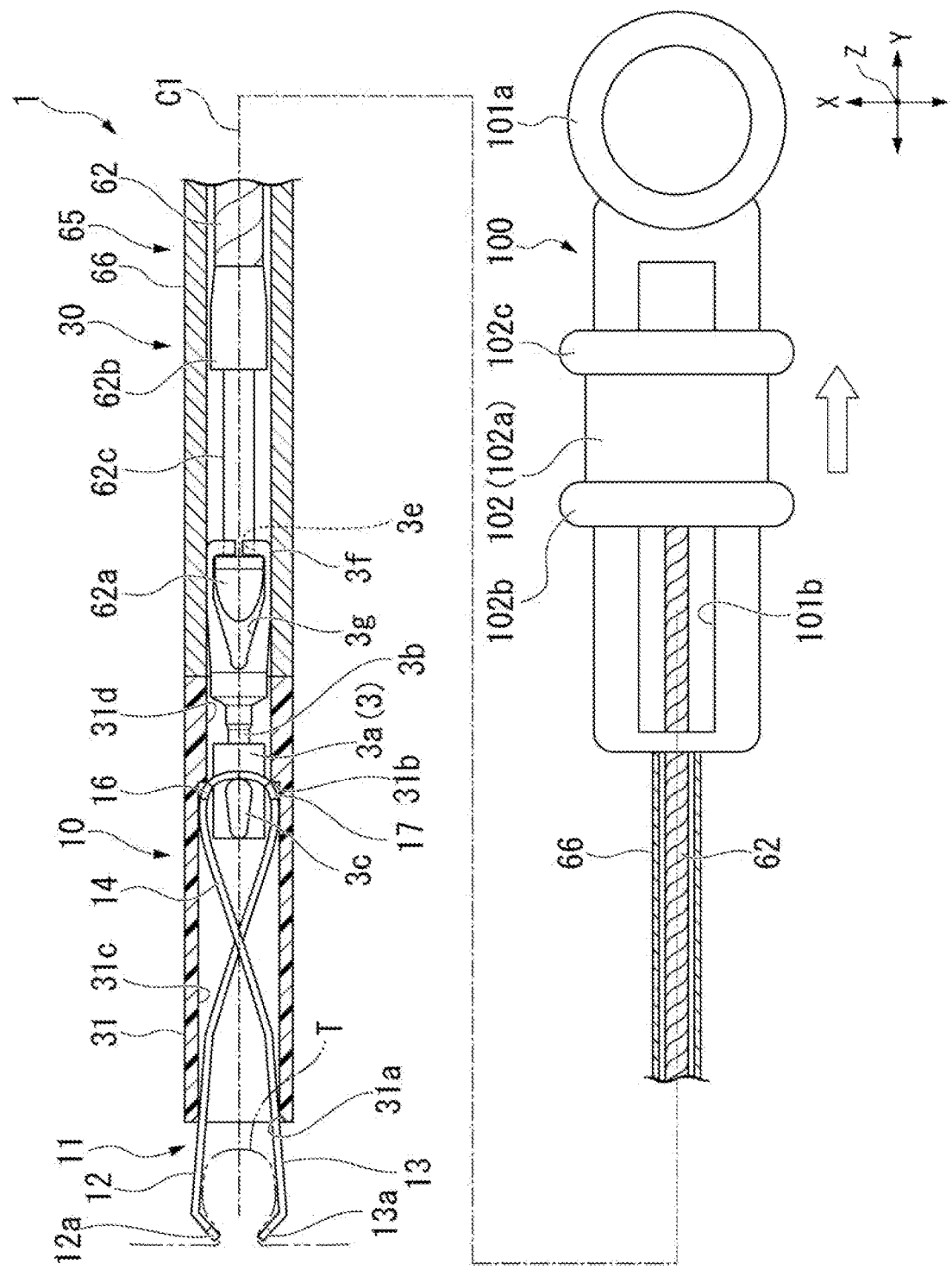
FIG. 11 is a view showing the operation of treating the target tissue using a medical device according to the present embodiment.
Figure 12:
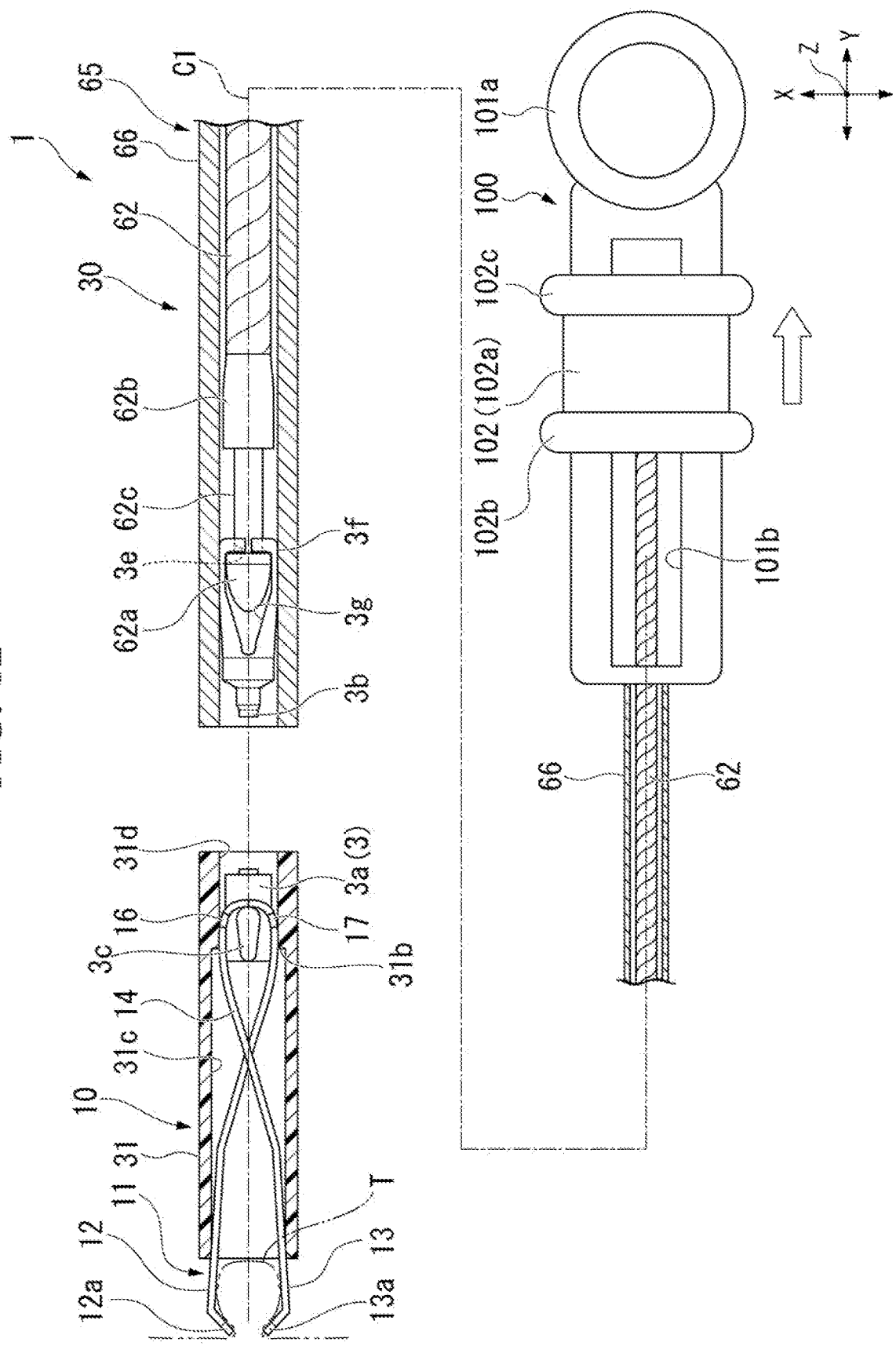
FIG. 12 is a view showing the operation of treating the target tissue using a medical device according to the present embodiment.

As shown in FIG. 10 and FIG. 11, in the process in which the operator retracts the slider 102 to the proximal end side, the proximal end portion of the arm member 11 including the intermediate portion 14 is retracted to the proximal end side in the pressing tube 31. According to the present embodiment, when the pair of first locked portions 16, 17 provided at the proximal end portion of the arm member 11 are located at more distal end side than the step portion 31b in the pressing tube 31, the operator may move the arm member 11 toward the distal end side by pushing the slider 102 toward the distal end side. In other words, in the state in which the pair of first locked portions 16, 17 of the arm member 11 are located at more distal end side than the step portion 31b, the operator may cause the arm member 11 to transition from the closed configuration to the open configuration by pushing the slider 102 toward the distal end side. By this operation, the operator may re-grasp the target tissue T using the arm member 11.

That is, in the process of retracting the slider 102 until the above-described state, the operator may operate the endoscope so as to direct the clip 10 toward the target tissue T again. Subsequently, the target tissue T maybe re-grasped by the clip 10 by the procedure described above.

As a result of the operator retracting the slider 102 to the proximal end side, as shown in FIG. 11, the target tissue T is grasped by the arm member 11 in the state of being tightly bound by the first arm 12 and the second arm 13 at the root of the target tissue T. According to the present embodiment, the state in which the distance between the first arm 12 and the second arm 13 is substantially zero is included in the closed configuration of the arm member 11. In this procedure, as shown in FIG. 11, the connection portion of the hook 62*a* and the connection portion 3 is moved toward the proximal end side in the pressing tube 31 and partially enters the sheath 66. According to the present embodiment, since the inner diameter of the sheath 66 is substantially equal to the inner diameter of the small-diameter portion 31*d* of the pressing tube 31, it is impossible for the engagement between the hook 62*a* and the connection portion 3 in the sheath 66 to be unintentionally released.

When the operator confirms that the target tissue T is grasped in a desired state by the arm member 11 in the closed state, the operator may retract the slider 102 toward the proximal end side until the pair of first locked portions 16, 17 provided on the arm member 11 climb over the step portion 31*b* in the pressing tube 31 to be positioned in the small-diameter portion 31*d*. In this state, the pair of first locked portions 16 and 17 cuts into the inner wall of the small-diameter portion 31*d* of the pressing tube 31 so as to restrict the arm member 11 from moving toward the distal end side with respect to the pressing tube 31. In other words, when the pair of first locked portions 16, 17 provided on the arm member 11 are located in the small-diameter portion 31*d* of the pressing tube 31, the state in which the arm member 11 in the closed configuration grasps the target tissue T is maintained.

According to the present embodiment, even if the operator operates the slider 102 (pushing the slider 102 toward the distal end side or retracting the slider 102 toward the proximal end side), the state in which the connection portion between the connection portion 3 and the hook 62*a* is positioned in the pressing tube 31 or the sheath 66 is maintained. Accordingly, according to the present embodiment, even if the operator operates the slider 102 to re-grasp the target tissue T using the arm member 11, the engagement between the connection portion 3 and the hook 62*a* is not released.

The operator may confirm the state in which the target tissue T is grasped by the arm member 11 in the closed configuration. If the operator confirms that the target tissue T is grasped by the arm member 11 of the clip 10 in the desired state, the operator may lock the state in which the target tissue T is grasped by the clip 10 and indwell the clip 10 in the body.

Specifically, the operator further retracts the slider 102 toward the proximal end side such that the pair of first locked portions 16, 17 provided on the arm member 11 are positioned in the small-diameter portion 31*d* of the pressing tube 31. In this state, the first arm 12 and the second arm 13 of the arm member 11 come into contact with the tapered surface 31*a* at the distal end side of the pressing tube 31 and pressed by the tapered surface 31*a*. Accordingly, the state in which the first arm 12 and the second arm 13 of the arm member 11 grasp the target tissue T in the closed configuration is maintained. At this time, the force of retracting the slider 102 to the proximal end side by the operator concentrates on the connection portion 3 such that the most fragile rod-shaped portion 3*b* in the connection portion 3 is broken. As a result, as shown in FIG. 12, when the target tissue T is tightly bound by the clip 10, the connection portion 3 is broken at the rod-shaped portion 3*b*, the distal end portion 3*a* of the connection portion 3 is indwelled in the body together with the clip 10, and the proximal end portion 3*f* in the state of engaging with the hook 62*a* is removed from the body by the operation wire 62.

After the clip 10 ligating the target tissue T is indwelled in the body, the operator operates the endoscope to take out the medical device 1 from the channel of the endoscope. Subsequently, the operator takes necessary measures and finishes the series of procedures.

As shown in FIG. 13 and FIG. 14, the situation in which the connection portion between the connection portion 3 and the hook 62*a* is located outside the pressing tube 31 is assumed. In this case, when the connection portion 3 is rotated along the direction indicated by the arrow D and intersecting the direction of the axis C1, the hook 62*a* may be pulled out from the side of the notch portion 3*g* of the connection portion 3. In other words, when the connection portion between the connection portion 3 and the hook 62*a* is located outside the pressing tube 31, there is possibility that the engagement state of the connection portion 3 and the hook 62*a* is unintentionally released. As a result, the clip 10 may be unintentionally slipped from off the applicator 30.

According to the medical device 1 according to the present embodiment, during the operation of attaching the clip 10 to the applicator 30, the connection portion between the connection portion 3 and the hook 62*a* may be accommodated in the pressing tube 31 by engaging the hook 62*a* provided at the distal end of the operation wire 62 to the notch portion 3*g* of the connection portion 3 and subsequently moving the stopper 36 outward in the radial direction of the housing 40 along the vertical groove 393. In the state in which the connection portion between the connection portion 3 and the hook 62*a* is accommodated in the pressing tube 31, the connection portion 3 cannot rotate with respect to the hook 62*a*.

Furthermore, in the process of treating the target tissue T with the clip 10 attached to the applicator 30, during the operation of the operator to push the slider 102 of the operation portion 100 toward the distal end side or retract the slier 102 toward the proximal end side, the state in which the connection portion between the connection portion 3 and the hook 62*a* is accommodated in the pressing tube 31 is maintained.

According to the medical device 1 according to the present embodiment, it is possible to prevent the clip 10 from unintentionally slipping from the applicator 30.

According to the medical device 1 according to the present embodiment, the relative position between the connection portion 3 engaged with the clip 10 and the pressing tube 31 may be controlled by the stopper 36 in the housing 40 that accommodates the clip 10. Specifically, when the stopper 36 moves toward the distal end side along the horizontal groove 392, the pressing tube 31 advances with respect to the connection portion 3 and the connection portion 3 protrudes from the opening of the pressing tube 31 at the proximal end side. On the other hand, when the stopper 36 moves to the proximal end side along the horizontal groove 392, the pressing tube 31 retracts with respect to the connection portion 3, and the connection portion 3 or the connection portion 3 and the hook 62a that engage with each other are accommodated in the pressing tube 31.

According to the clip cartridge 80 according to the present embodiment, without changing the configuration of the clip 10, it may be easy to protrude the connection portion 3 from the opening of the pressing tube 31 at the proximal end side at the time of attaching the clip 10 to the applicator 30 by providing the L-shaped groove 391 and the stopper 36 in the housing 40. On the other hand, after attaching the clip 10 to the applicator 30, it may be easy to accommodate the connection portion between the connection portion 3 and the hook 62a in the pressing tube 31. That is, according to the stopper 36 of the housing 40 according to the present embodiment, it is possible to control the transition of the connection portion 3 between the accommodation configuration and the protrusion configuration and the protrusion amount of the connection portion 3 from the pressing tube 31 when the connection portion 3 is in the protrusion configuration.

According to the clip cartridge 80 according to the present embodiment, both goals of the reloadable operation of the clip 10 with respect to the applicator 30 and the operation of re-grasping the target tissue T may be achieved.

According to the present embodiment, for convenience of description, the example in which the inner diameter of the sheath 66 is substantially the same with the inner diameter of the small-diameter portion 31d of the pressing tube 31 has been described; however, the present disclosure is not limited to this configuration. As described above, in the present embodiment, the hook 62a of the operation wire 62 only has to be engaged with the notch portion 3g by pressing the pair of legs of the proximal end portion 3f to cause the pair of legs to be elastically deformed in the state in which the proximal end portion 3f of the connection portion 3 is not accommodated in the pressing tube 3 or the sheath 66. For example, both of the inner diameter of the sheath 66 and the inner diameter of the pressing tube 31 only have to be smaller than the width of the proximal end portion 3f of the connection portion 3 in the direction of the axis X when the hook 62a enters the insertion hole 3e of the connection portion 3, and the inner dimeter of the sheath 66 and the inner diameter of the pressing tube 31 may be different.

According to the medical device 1 according to the present embodiment, the housing 40 may be easily configured by forming the L-shaped groove 391 and the stopper 36 in various known configurations, and thus the manufacturing may be easy. Accordingly, the medical device 1 may be manufactured at low cost.

(Modification)

The configuration of a medical device according to a modification of the first embodiment of the present disclosure will be described below with reference to FIG. 15A to FIG. 19C. Hereinafter, the same configurations as those of the medical device 1 according to the above-described embodiment will be designated by the same reference numerals, the description thereof will be omitted, and differences from the above-described embodiment will be mainly described.

A medical device 1A according to the present modification includes a clip 10A instead of the clip 10 as compared with the medical device 1 according to the above embodiment. The clip 10A includes a pressing tube 31A, an arm member 11A, and a connection portion 3. A support portion 66A configured to support the clip 10A is formed at the distal end portion of the sheath 66 of the applicator 30. The medical device 1A according to the present modification includes the housing 40 of the medical device 1 according to the first embodiment described above. That is, the clip cartridge 80 according to the present modification is configured to accommodate the clip 10A in the housing 40.

FIG. 15A to FIG. 16E are views showing operations of attaching the clip 10A to the applicator 30A in the medical device 1A according to the present modification. FIG. 17A to FIG. 19C are views showing a procedure using the medical device 1A according to the present modification.

As shown in FIG. 15A, the clip 10A of the medical device 1A according to the present modification includes an elastic member 35 and a locking portion 32 provided inside the pressing tube 31A. Further, the arm member 11A of the clip 10A has protrusions 18, 19, 23, 24 connected to the elastic member 35 and the locked portions 16, 17, 21, 22 which may be locked by the locking portion 32.

(Structure of Elastic Member)

The elastic member 35 is configured to have a distal end portion locked to the protrusions 18, 19, 23, 24 and a proximal end portion locked to the locking portion 32 in the pressing tube 31A. The proximal end portion of the elastic member 35 and the locking portion 32 may be fixed by welding or the like.

The portion at more proximal end side than the protrusions 18, 19 in the first arm 12, the portion at more proximal end side than the protrusions 23, 24 in the second arm 13, and the intermediate portion 14 are insertable through the elastic member 35.

According to the present modification, the elastic member 35 is compressed in the axial direction Y when the protrusions 18, 19, 23, 24 are moved to the proximal end side together with the first arm 12 and the second arm 13 of the arm member 11A. When the elastic member 35 is compressed, an elastic force that pushes the arm member 11A from the pressing tube 31A in the axial direction Y is generated. According to the present modification, the elastic member 35 may be configured by, for example, a spiral spring.

According to the present modification, since the elastic member 35 is configured in the pressing tube 31A, the pair of legs of the connecting member 3 may interfere with the elastic member 35 in the pressing tube 31A, and thus it is impossible for the pair of legs to elastically deform outward in the radial direction. In other words, according to the present modification, similar to the above-described first embodiment, it is impossible for the hook 62a of the operation wire 62 to pass through the insertion hole 3e of the connection portion 3 to be engaged with the notch portion 3g in the pressing tube 31A.

(Structure of Arm Member)

As shown in FIG. 15A, according to the present modification, two of first locked portions 16, 17 are provided at the proximal end portion of the first arm 12 of the arm member 11A. The first locked portions 16, 17 are disposed to protrude from the side surface of the first arm 12 in the orthogonal direction Z on a plane parallel to the longitudinal axis of the pressing tube 31A. The first locked portions 16, 17 are formed to protrude in directions opposite to each other.

Figure 15B:
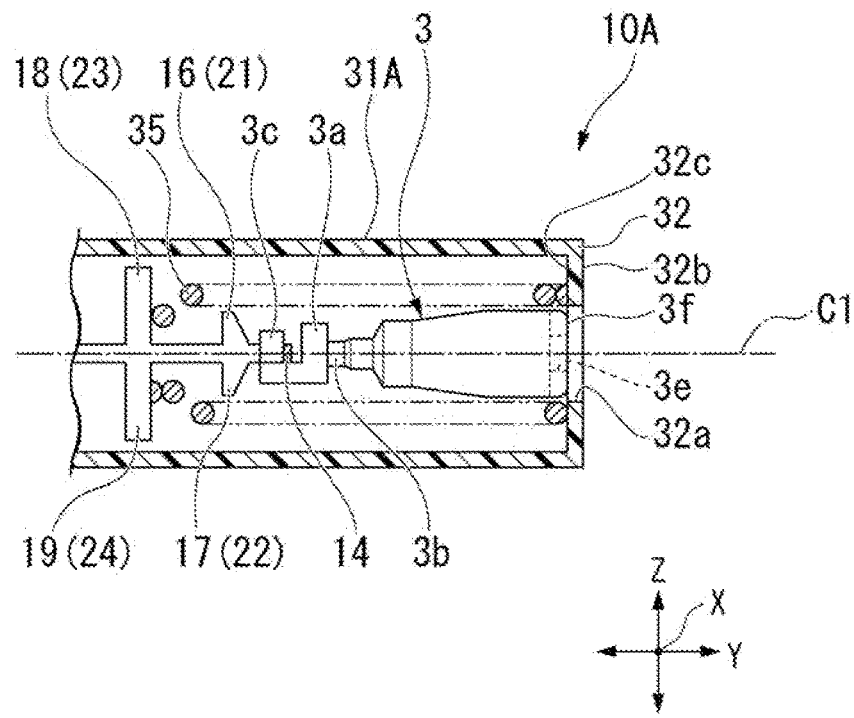
FIG. 15B is a partial cross-sectional side view showing the clip unit according to the present modification.

In the planar view shown in FIG. 15B, the first locked portion 16 and the first locked portion 17 are formed line-symmetrically with respect to the longitudinal axis of the pressing tube 31A. The proximal end surface 16a of the first locked portion 16 is separated from the first arm 12 toward the distal end side, and the proximal end surface 16a is inclined with respect to the longitudinal axis along which the first arm 12 extends. The distal end surface 16b of the first locked portion 16 is orthogonal to the axial direction Y. The proximal end surface 17a of the first locked portion 17 and the proximal end surface 16a of the first locked portion 16 are line-symmetric with respect to the longitudinal axis of the pressing tube 31A. The distal end surface 17b of the first locked portion 17 and the distal end surface 16b of the first locked portion 16 are line-symmetric with respect to the longitudinal axis of the pressing tube 31A.

As shown in FIG. 15A, in the first arm 12, the two of protrusions 18, 19 are provided at more distal end side than the first locked portions 16, 17. As shown in FIG. 15B, the protrusions 18, 19 protrude from the side surface of the first arm 12 in the orthogonal direction Z. The protrusion 18 and the protrusion 19 are line-symmetric with respect to the longitudinal axis of the pressing tube 31A in the planar view. The protrusion lengths of the protrusions 18, 19 protruding from the first arm 12 may be larger than the protrusion lengths of the first locked portions 16, 17 protruding from the first arm 12 in the orthogonal direction Z.

The second arm 13 is configured to include the second locked portions 21, 22 and protrusions 23, 24 formed in the same manner as the first locked portions 16, 17 and the protrusions 18, 19 of the first arm 12. That is, the second locked portions 21, 22 protrude from the side surface of the second arm 13 in the orthogonal direction Z which is a direction in which the second arm 13 is separated from the second arm 13. The protrusions 23, 24 protrude in the orthogonal direction Z from the side surface of the second arm 13 and disposed at more distal end side than the second locked portions 21 and 22 of the second arm 13. The second locked portions 21, 22 and the first locked portions 16, 17 are arranged in the opposite direction X while the protrusions 23, 24 and the protrusions 18, 19 are arranged in the opposite direction X. In the planar view shown in FIG. 15B, the second locked portions 21, 22 overlap the first locked portions 16, 17, and the protrusions 23, 24 overlap the protrusions 18, 19, respectively.

(Structure of Locking Portion)

Figure 15C:
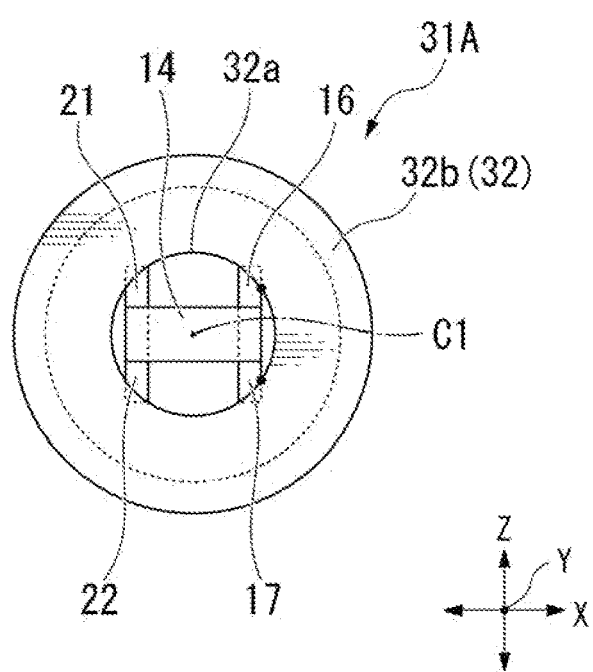
FIG. 15C is a view viewed from the proximal end side of the clip unit according to the present modification.

As shown in FIG. 15A and FIG. 15B, a locking portion 32 is formed to protrude over the whole circumference on the inner wall of the proximal end portion of the pressing tube 31A. As shown in FIG. 15C, an edge portion 32a of the locking portion 32 on the axis C1 side is formed in a circular shape coaxial with the pressing tube 31A. As shown in FIG. 15A and FIG. 15B, the proximal end surface (proximal end side end surface) 32b and the distal end surface (distal end side surface) 32c of the locking portion 32 are orthogonal to the axial direction Y. The portion of the first arm 12 at the more proximal end side than the protrusions 18, 19, the portion of the second arm 13 at the more proximal end side than the protrusions 23, 24, and the intermediate portion 14 are insertable into the locking portion 32.

(Configuration of Sheath)

Figure 16A:
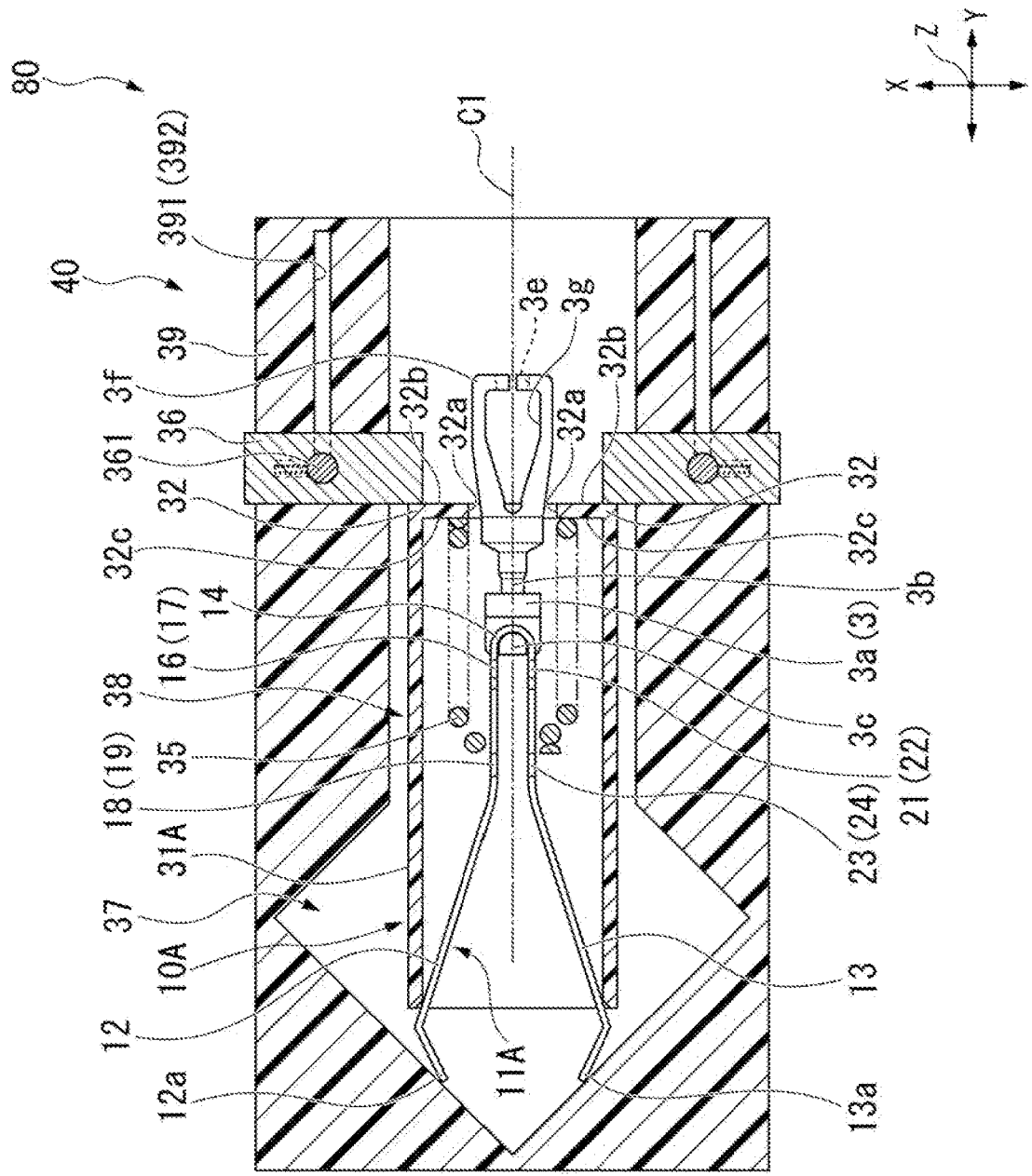
FIG. 16A is a view showing an operation of attaching the clip unit to the applicator according to the present modification.
Figure 16B:
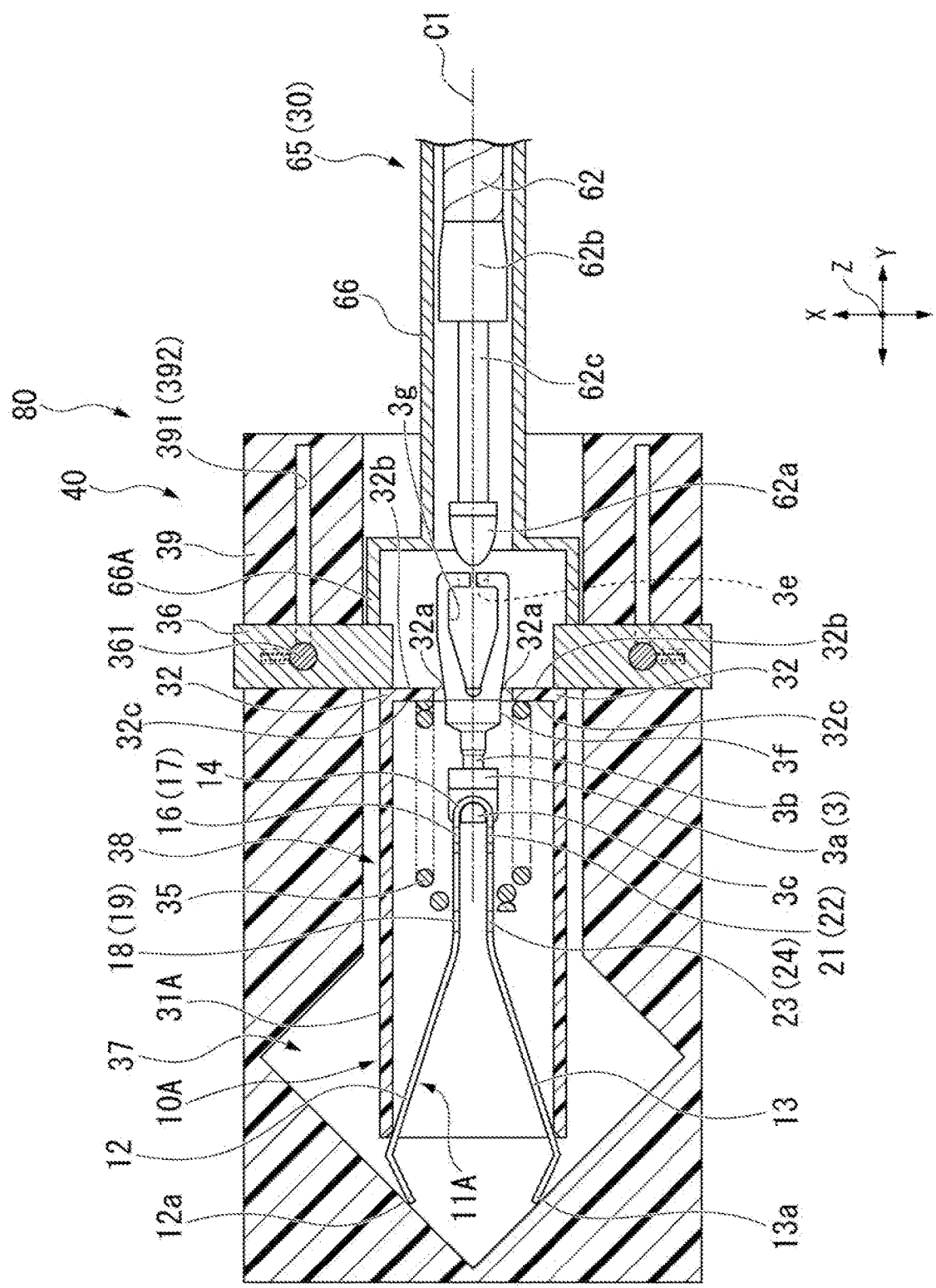
FIG. 16B is a view showing the operation of attaching the clip unit to the applicator according to the present modification.

As shown in FIG. 16B, a support portion 66A supporting the proximal end portion of the pressing tube 31A is formed on the distal end side of the sheath 66 of the applicator 30 according to the present modification. The inner diameter of the support portion 66A may be equal to or larger than the width of the pressing tube 31A in the radial direction. The outer diameter of the sheath 66 in the support portion 66A is smaller than the inner diameter of the lumen 38 of the housing 40. According to the present modification, the sheath 66 having such a structure may be inserted into the lumen 38 of the housing 40 to abut on the stopper 36 and support the pressing tube 31A as shown in FIG. 16B.

According to the present modification, for convenience of description, the example in which the inner diameter of the support portion 66A of the sheath 66 is larger than the inner diameters of the other portions of the sheath 66 is described; however, the present disclosure is not limited to this configuration. For example, the support portion that supports the pressing tube 31A may be formed by cutting off a part of the inner circumferential surface of the distal end portion of the sheath 66.

According to the present modification, the sheath 66 is formed such that the inner diameter thereof is substantially equal to the distance between the pair of elastic members 35 provided in the pressing tube 31A. Therefore, in the present modification, it is impossible for the hook 62a of the operation wire 62 to pass through the insertion hole 3e of the connection portion 3 and engage with the notch portion 3g in the sheath 66.

(Operation to Attach the Clip to the Applicator)

Hereinafter, with reference from FIG. 15A to FIG. 16E, an operation of attaching the clip 10A according to the present modification to the applicator 30 will be described.

FIG. 15A is a view showing a state in which the clip 10A according to the present modification is accommodated in the housing 40. As shown in FIG. 15A, the pair of stoppers 36 are located on the proximal end side of the housing 40, and the respective distal end surfaces 364 are in contact with the proximal end surface 32b of the locking portion 32 of the pressing tube 31A. In this state, the elastic member 35 in the pressing tube 31A may be in a non-pressed state, for example. Further, the connection portion 3 is in the accommodated configuration of being accommodated in the pressing tube 31A.

Next, the operator grasps the pair of stoppers 36 to move the pair of stoppers along the horizontal groove 392 toward the distal end side. By this operation, as shown in FIG. 16A, the proximal end surface 32b of the locking portion 32 of the pressing tube 31A engages with the distal end surface 364 of the stopper 36 so as to move the pressing tube 31A toward the distal end side with respect to the clip 10A. As a result, when the pin 361 formed integrally with the stopper 36 reaches the distal end of the horizontal groove 392, the connection portion 3 is in the protrusion configuration protruding from the opening on the proximal end side of the pressing tube 31A. In the pressing tube 31A, the elastic member 35 is compressed in the longitudinal axis direction of the pressing tube 31A. Further, the first arm 12 and the second arm 13 of the arm member 11A transition from the open configuration shown in FIG. 15A to the closed configuration.

As shown in FIG. 16A, in the state in which the connection portion 3 protrudes from the opening on the proximal end side of the pressing tube 31A, the operator may move the operating wire 62 toward the pressing tube 31A so as to engage the hook 62a disposed on the distal end of the operation wire 62 with the notch portion 3g via the insertion hole 3e of the connection portion 3. As shown in FIG. 16B, the operator operates the operation portion 100 of the applicator 30 to insert the sheath 66 into the lumen 38 of the housing 40, and makes the distal end surface of the support portion 66A of the sheath 66 to be in contact with the proximal end surface 363 of the stopper 36. In this state, the hook 62a is located at the proximal end side of the connection portion 3 and apart from the connection portion 3.

Figure 16C:
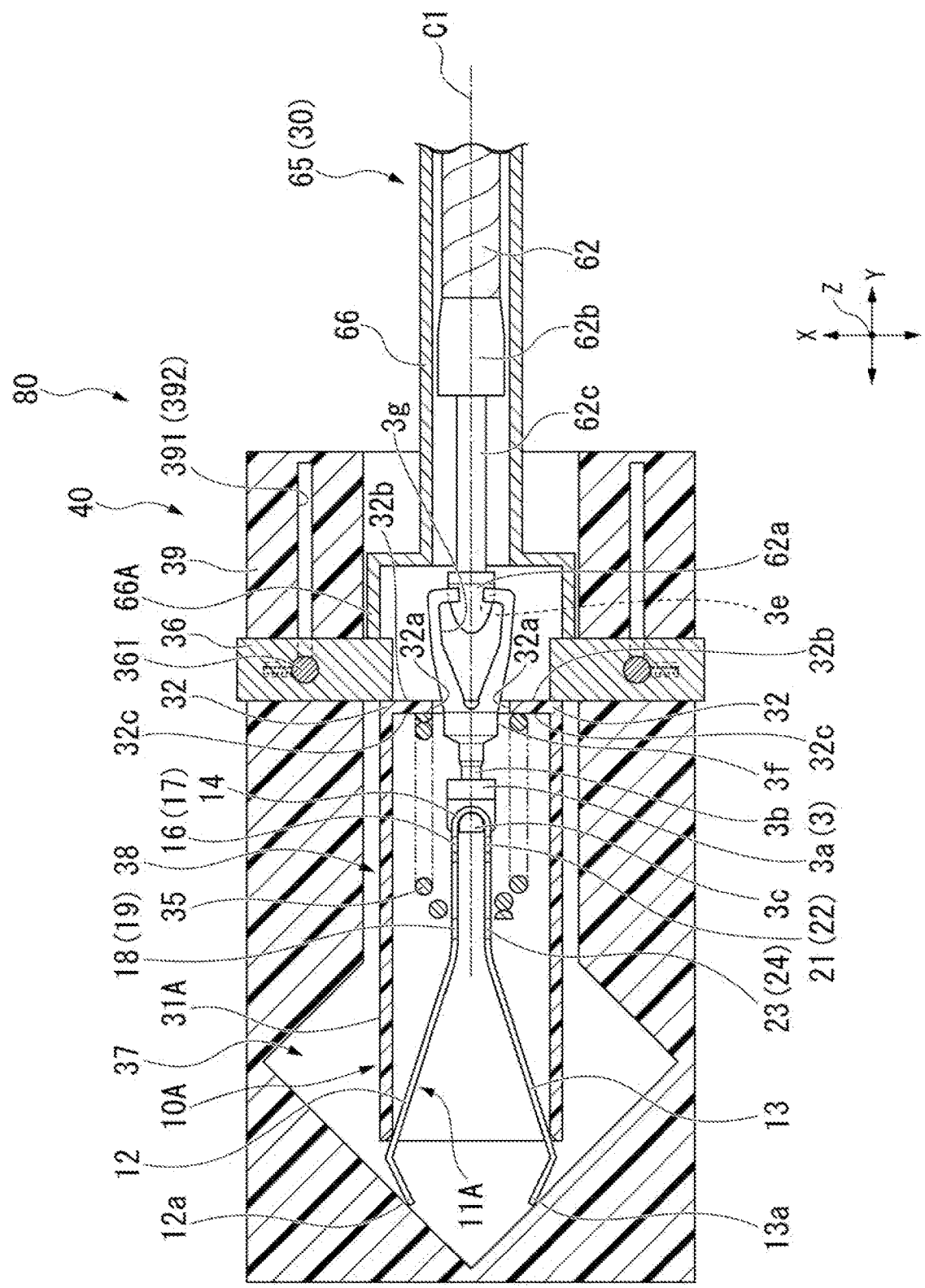
FIG. 16C is a view showing the operation of attaching the clip unit to the applicator according to the present modification.

Subsequently, the operator pushes the slider 102 toward the distal end side along the slit 101b of the operation section body 101. By this operation, as shown in FIG. 16C, the hook 62a is moved toward the connection portion 3 and toward the distal end side together with the operation wire 62. The hook 62a passes through the insertion hole 3e formed in the proximal end portion 3f of the connection portion 3 and enters the notch portion 3g of the connection portion 3. At this time, the hook 62a presses the proximal end surface of the insertion hole 3e formed in the proximal end portion 3f of the connection portion 3, and the pair of legs of the proximal end portion 3f of the connection portion 3 elastically deforms radially outward such that the width of the insertion hole 3e increases. When the width of the deformed insertion hole 3e becomes equal to or larger than the width d of the hook 62a, the hook 62a can pass through the insertion hole 3e and enter the notch portion 3g of the connection portion 3. As shown in FIG. 16C, in this state, the width of the proximal end portion 3f of the connection portion 3 is smaller than the distance between the pair of stoppers 36, and larger than the distance between the pair of elastic members 35 in the pressing tube 31A or the inner diameter of the sheath 66. As a result, the hook 62a is engaged with the notch portion 3g of the connection portion 3 such that the operation wire 62 and the clip 10A are connected with each other in the engaged state.

According to the present modification, similar to the above-described first embodiment, only in the state in which at least part of the proximal end portion 3f of the connection portion 3 is not accommodated in the pressing tube 31A or the sheath 66 and is exposed to the outside (for example, positioned between the pair of stoppers 56), the operator may engage the hook 62a with the notch portion 3g of the connection portion 3.

Figure 16D:
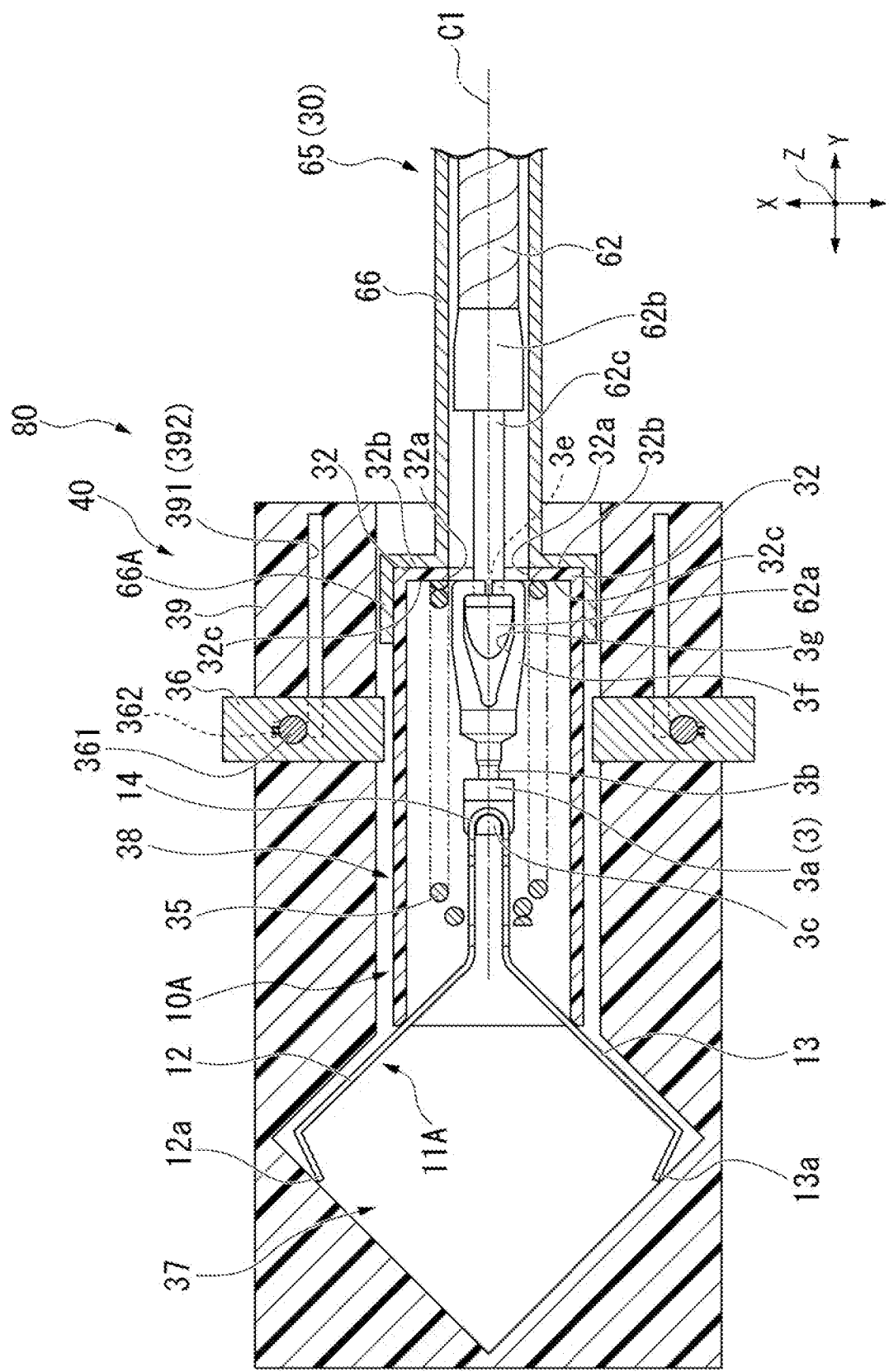
FIG. 16D is a view showing the operation of attaching the clip unit to the applicator according to the present modification.

As shown in FIG. 16D, the operator moves the pair of stoppers 36 along the vertical groove 393 outward in the radial direction of the housing 40 while the hook 62a is engaged with the notch portion 3g of the connection portion 3. As a result, the engagement between the proximal end surface of the pressing tube 31A (proximal end surface 32b of the locking portion 32) and the distal end surface 364 of the stopper 36 is released. As shown in FIG. 16D, the elastic restoring force of the first arm 12 and the second arm 13 of the arm member 11 of the clip 10 applies on the pressing tube 31A such that the pressing tube 31A moves toward the proximal end side, and the proximal end surface of the pressing tube 31A and a surface of the support portion 66A of the sheath 66 that faces toward the distal end side are in contact with each other. That is, the pressing tube 31A is supported by the support portion 66A of the sheath 66.

By this operation, the restriction to the transition from the protrusion configuration to the accommodation configuration of the connection portion 3 by the stopper 36 is released, and the pressing tube 31A is moved to the proximal end side with respect to the connection portion 3 such that the connection portion 3 transitions from the protrusion configuration to the accommodation configuration. As shown in FIG. 16D, the connection portion 3 between the connection portion 3 and the hook 62a is located inside the pressing tube 31A.

Figure 16E:
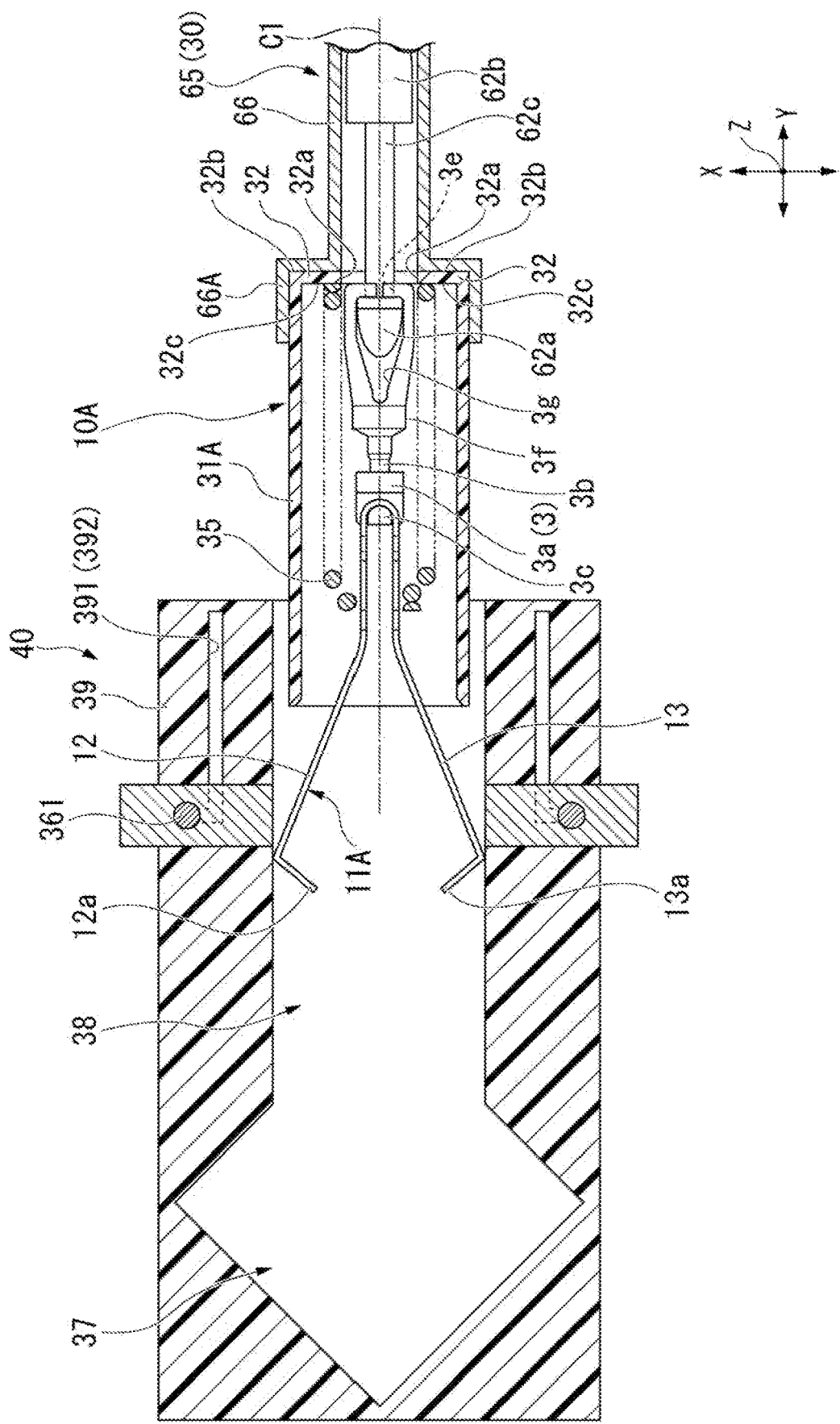
FIG. 16E is a view showing the operation of attaching the clip unit to the applicator according to the present modification.

Similar to the above-described first embodiment, the operator operates the operation portion main body 101 of the operation portion 100, and as shown in FIG. 16E, the operation wire 62 and the clip 10A engaged with the operation wire 62 may be removed from the opening at the proximal end side of the lumen 38 of the housing 40. As described above, the clip 10A according to the present modification is attached to the applicator 30. As shown in FIG. 16E, in the state in which the clip 10A is attached to the applicator 30, the connection portion 3 is in the accommodation configuration of being accommodated in the pressing tube 31A.

(Procedure with Medical Device)

Next, a procedure for ligating the target tissue T with the medical device 1A according to the present modification will be described with reference to FIG. 17A to FIG. 19C.

When the clip 10A is taken out from the housing 40 by the elastic restoring force of the first arm 12 and the second arm 13 of the arm member 11A of the clip 10A, the first arm 12 and the second arm 13 of the arm member 11A are separated from each other to be in the open configuration.

Figure 17A:
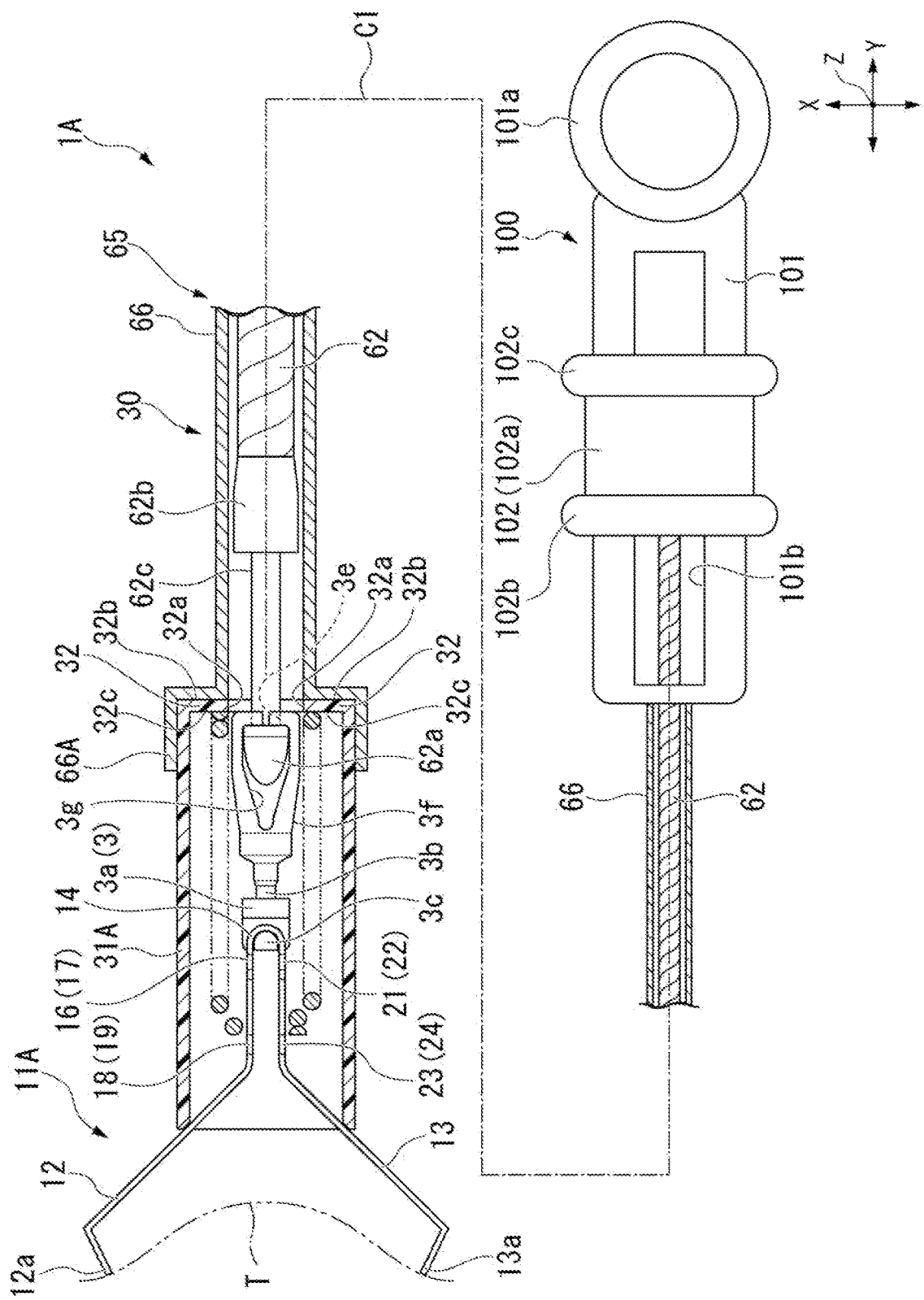
FIG. 17A is a view showing an operation of treating the target tissue using a medical device according to the present modification.

In this state, the operator moves the medical device 1A to the vicinity of the target tissue T to be treated in the same manner as in the first embodiment. Subsequently, the operator operates the slider 102 to adjust the opening width between the first arm 12 and the second arm 13 of the arm member 11A in accordance with the size of the target tissue T, and as shown in FIG. 17A, the arm member 11A is pressed against the target tissue T.

Figure 17B:
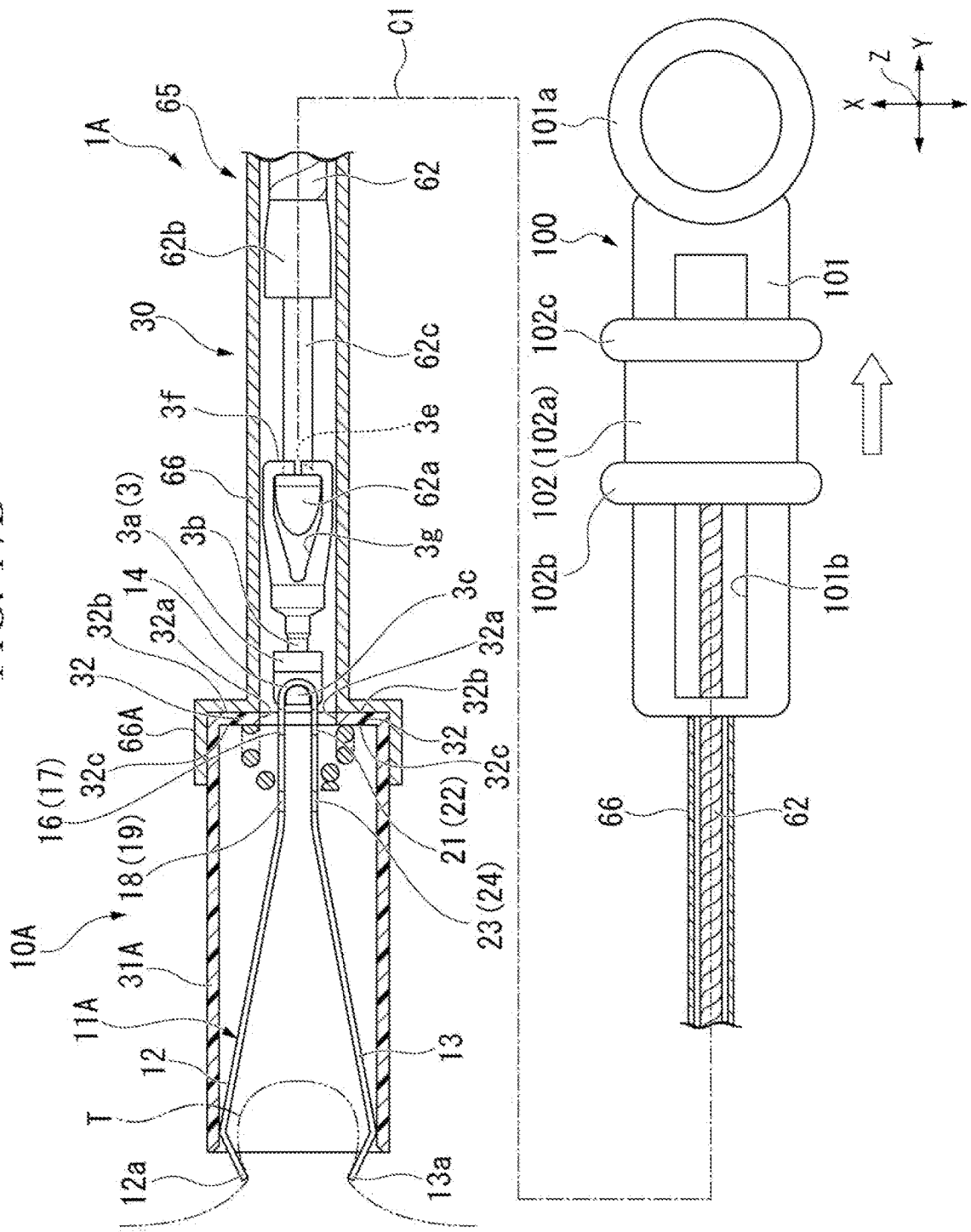
FIG. 17B is a view showing the operation of treating the target tissue using the medical device according to the present modification.

When the operator can confirm that the target tissue T is located between the first arm 12 and the second arm 13, the operator grasps the operation portion main body 101 and retracts the slider 102. At this time, the first arm 12 and the second arm 13 are moved to the proximal end side together with the operation wire 62, and the opening width therebetween is decreased. By this operation, as shown in FIG. 17B, the first arm 12 and the second arm 13 of the arm member 11A may grasp the target tissue T.

Figure 17C:
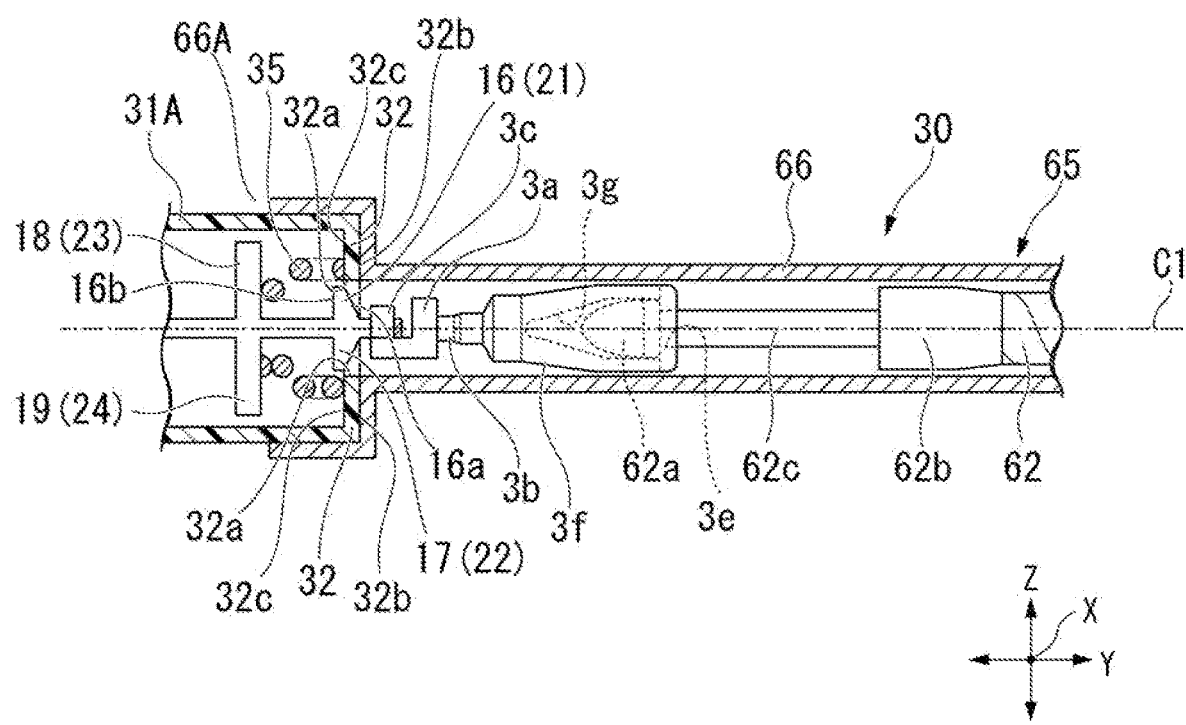
FIG. 17C is a view showing the operation of treating the target tissue using the medical device according to the present modification.

At this time, as shown in FIG. 17C, the elastic member 35 in the pressing tube 31A is compressed, and the first locked portions 16, 17 of the first arm 12 and the second locked portions 21, 22 of the second arm 13 of the arm member 11A partially enter the locking portion 32. More specifically, for example, the proximal end surface 16a of the first locked portion 16 is partially located at more proximal end side than the distal end surface 32c of the locking portion 32. Further, the connection portion 3 including the connection portion between the connection portion 3 and the hook 62a climbs over the locking portion 32 to be positioned inside the sheath 66 at more proximal end side than the proximal end surface 32b of the locking portion 32.

Figure 18A:
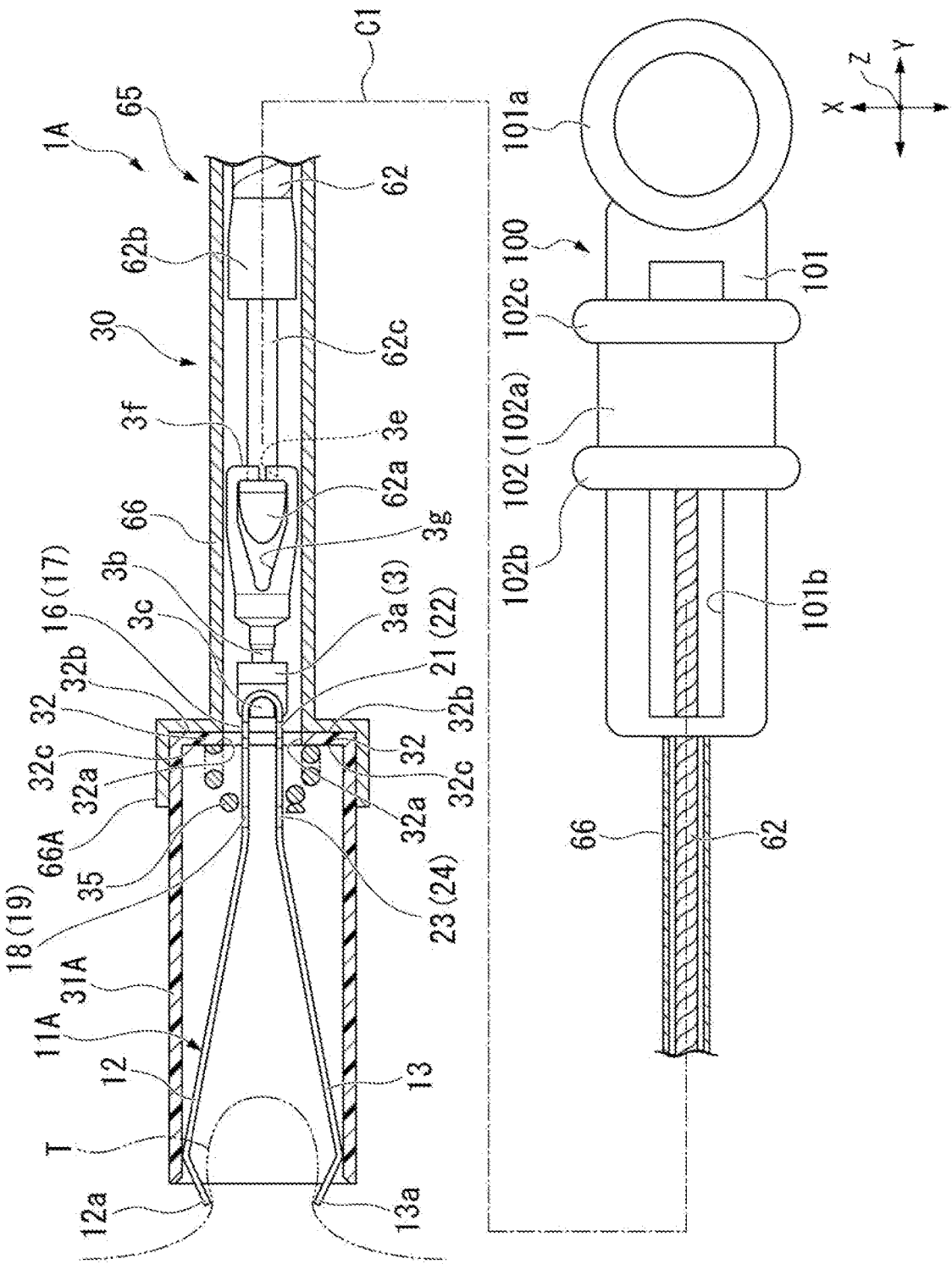
FIG. 18A is a view showing the operation of treating the target tissue using the medical device according to the present modification.
Figure 18B:
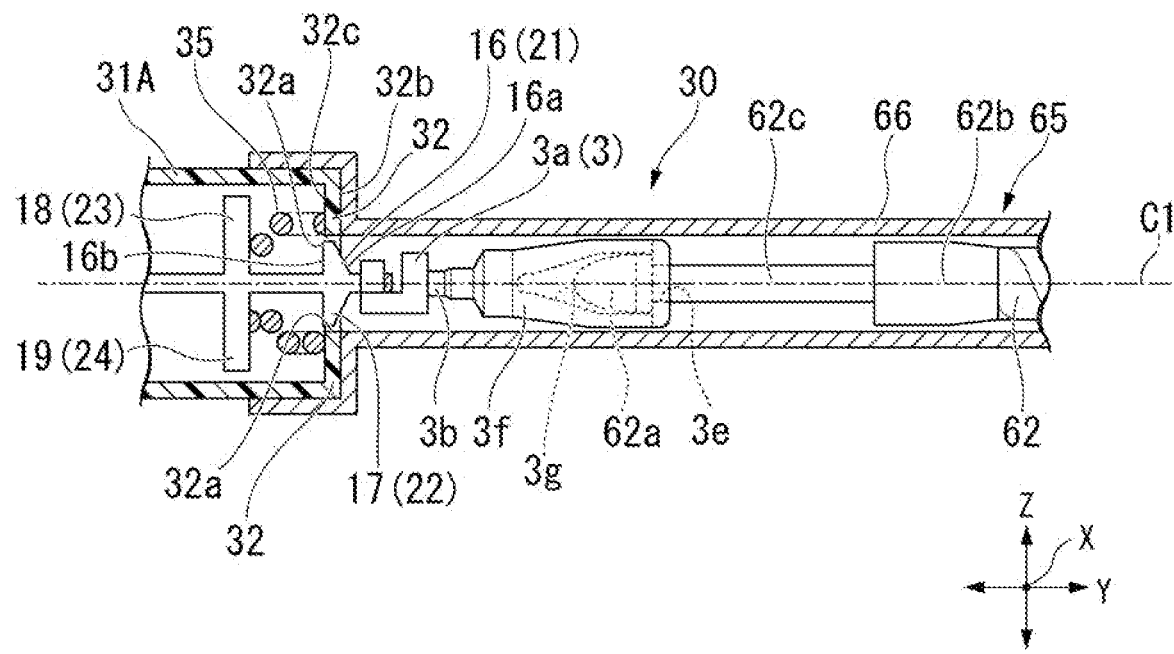
FIG. 18B is a view showing the operation of treating the target tissue using the medical device according to the present modification.
Figure 18C:
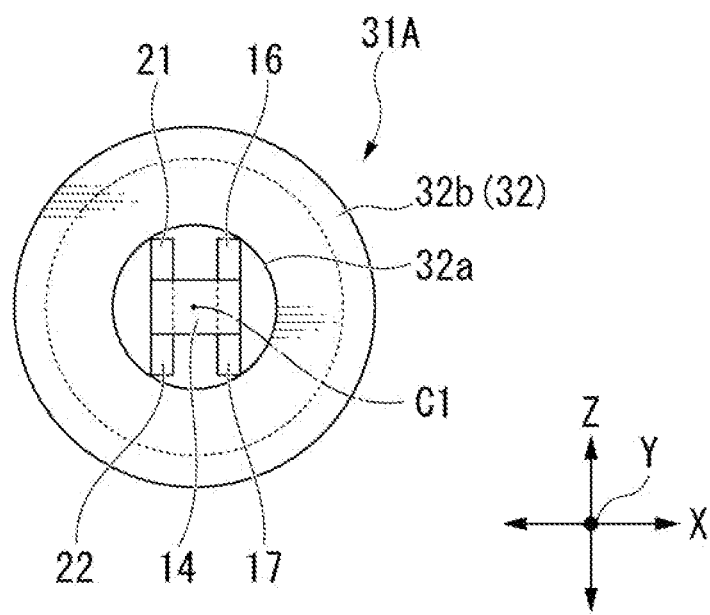
FIG. 18C is a view showing the operation of treating the target tissue using the medical device according to the present modification.

Due to the operation by the operator to further retract the slider 102 to the proximal end side, as shown in FIG. 18A to FIG. 18C, the first locked portions 16, 17 and the second locked portions 21, 22 of the arm member 11A completely enter the locking portion 32, and at least part of the first locked portions 16, 17 and the second locked portions 21, 22 is located at more distal end side than the proximal end surface 32b of the locking portion 32. At this time, as shown in FIG. 18B, the elastic member 35 in the pressing tube 31A is further compressed, and for example, the distal end of the proximal end surface 16a of the first locked portion 16 is positioned at more proximal end side than the distal end surface 32c of the locking portion 32, and at more distal end side than the proximal end surface 32b of the locking portion 32.

In this state, the intermediate portion 14 between the first arm 12 and the second arm 13 of the arm member 11A is compressed, and the distance between the proximal end portion of the first arm 12 and the proximal end portion of the second arm 13 is decreased. More specifically, as shown in FIG. 18C, when viewed from the proximal end side of the clip 10A along the direction of the longitudinal axis of the pressing tube 31A, the distance between the first locked portions 16, 17 and the second locked portions 21, 22 is smaller than that in the state shown in FIG. 15C.

According to the present modification, in the process of retracting the slider 102 from the state shown in FIG. 18A to FIG. 18C, the operator may move the operation wire 62 and the clip 10A to the distal end side by pushing the slider 102 toward the distal end side. By such operations, the first arm 12 and the second arm 13 of the clip 10A may transition from the closed configuration to the open configuration again. That is, in the medical device 1A according to the present modification, the operator only has to operate the slider 102 to re-grasp the target tissue T using the clip 10A.

In the operation of re-grasping the target tissue T using the clip 10A, the connection portion between the connection portion 3 and the hook 62a is moved from the sheath 66 to the distal end side and then accommodated in the pressing tube 31A again. Further, by the elastic force of the elastic member 35, the state in which the pressing tube 31A is supported by the support portion 66A of the sheath 66 is maintained. Accordingly, in the operation of re-grasping the target tissue T, the connection portion between the connection portion 3 and the hook 62a moves between the sheath 66 and the pressing tube 31; however, the connection portion thereof is not exposed to the outside. That is, it is possible to prevent the clip 10A from being unintentionally slipped from the applicator 30.

When the operator confirms that the target tissue T is grasped by the arm member 11A in the desired state, the operator may further retract the slider 102 to the proximal end side to move the first locked portions 16, 17 and the second locked portions 21, 22 of the arm member 11A such that the first locked portions 16, 17 and the second locked portions 21, 22 of the arm member 11A climb over the locking portion 32 to the position at more proximal end side than the locking portion 32.

Figure 19A:
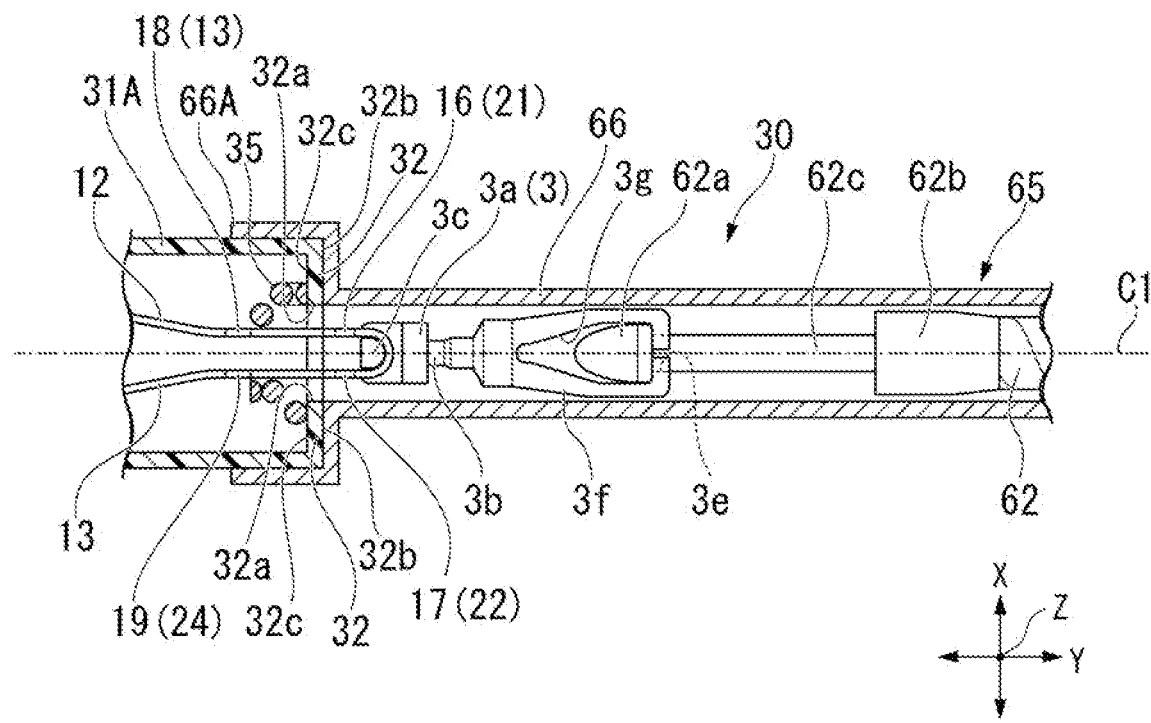
FIG. 19A is a view showing the operation of treating the target tissue using the medical device according to the present modification.
Figure 19B:
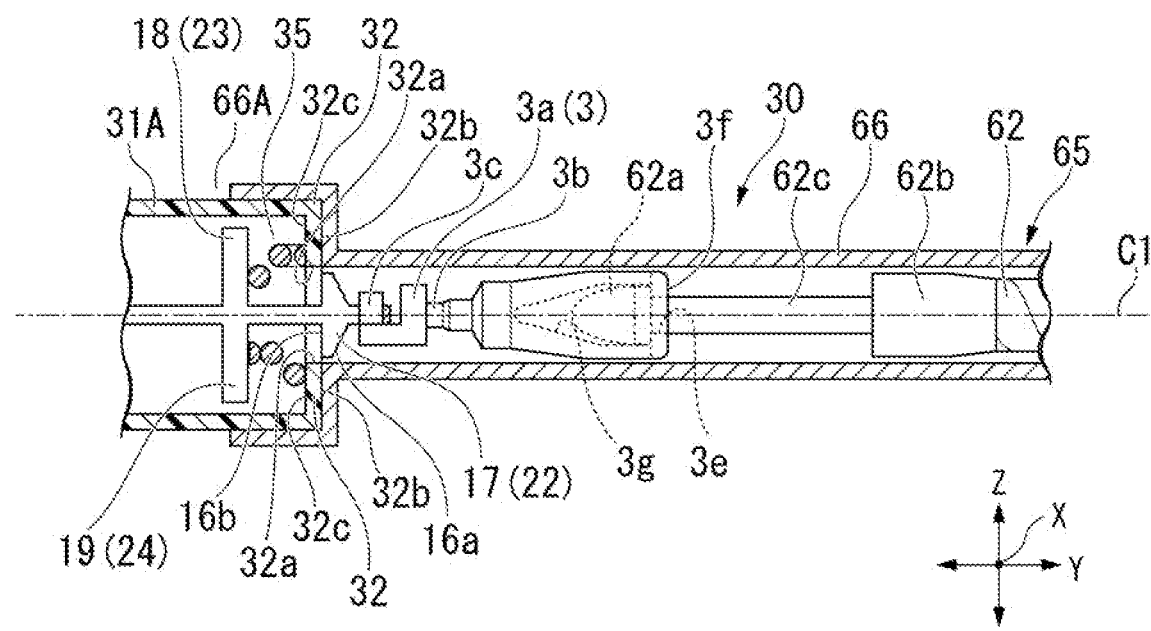
FIG. 19B is a view showing the operation of treating the target tissue using the medical device according to the present modification.

As shown in FIG. 19A to FIG. 19B, at this time, both the distal end surface 16b of the first locked portion 16 and the distal end surface 17b of the first locked portion 17 contact the proximal end surface 32b of the locking portion 32 such that the first locked portion 16 and the first locked portion 17 are locked to the locking portion 32. Similarly, both the distal end surface (not shown) of the second locked portion 21 and the distal end surface (not shown) of the second locked portion 22 contact the proximal end surface 32b of the locking portion 32 such that the second locked portion 21 and the second locked portion 22 are locked to the locking portion 32. At this time, the arm member 11A is in the closed configuration in which the distance between the first arm 12 and the second arm 13 is substantially zero. That is, the root of the target tissue T is tightly bound by the first arm 12 and the second arm 13 of the arm member 11A.

Figure 19C:
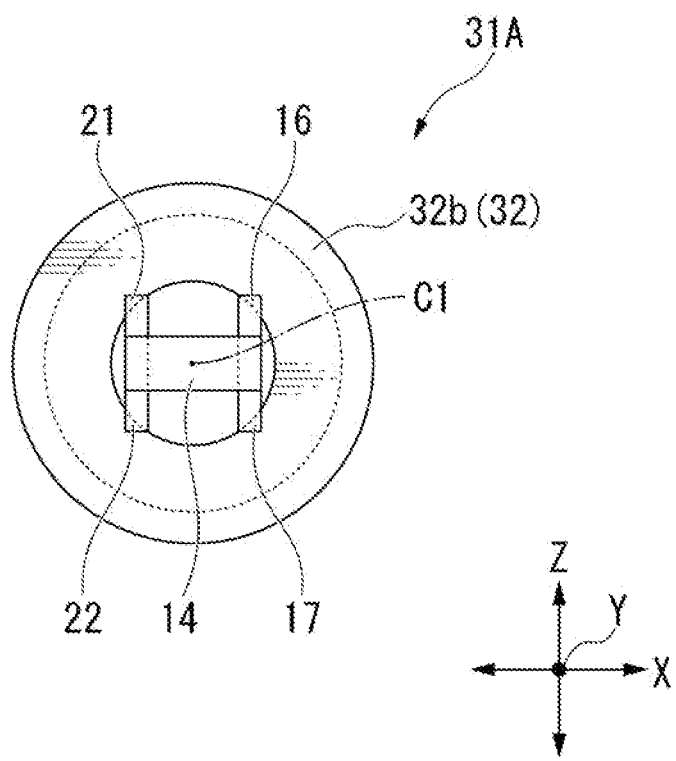
FIG. 19C is a view showing the operation of treating the target tissue using the medical device according to the present modification.

As shown in FIG. 19C, when viewed from the proximal end side of the clip 10A along the direction of the longitudinal axis of the pressing tube 31A, the distance between the first locked portions 16, 17 and the second locked portions 21, 22 in the radial direction of the clip 10A may be substantially the same as that in the state shown in FIG. 15C.

In this state, the elastic member 35 provided in the pressing tube 31A is in a tightly wound state in which the strands adjacent to each other in the axial direction Y are substantially in close contact with each other. In the clip 10A, the locking force generated since the first locked portions 16, 17 are locked to the proximal end surface 32b of the locking portion 32 and the elastic force of the elastic member 35 are in balance. Accordingly, unless there is an external force applied, the support portion 66A of the sheath 66 and the pressing tube 31A contact each other; however, the support portion 66A and the pressing tube 31A do not press each other. As a result, the operator operates the slider 102 such that the operation wire 62 and the clip 10A may move integrally.

Subsequently, when the operator further pulls back the slider 102 to the proximal end side, the pressing tube 31A cannot move to the proximal end side due to the support portion 66A of the sheath 66 such that the force for retracting the slider 102 to the proximal end side is concentrated in the connection portion 3. Similar to the first embodiment described above, the connection portion 3 is broken at the proximal end portion 3f. As a result, the clip 10A may be indwelled in the body while the target tissue T is ligated by the clip 10A in the closed configuration. The operator takes necessary measures and finishes a series of procedures.

The housing 40 according to the present modification has the same effects as the housing 40 according to the above-described first embodiment. The medical device 1A according to the present modification has the same effects as the medical device 1 according to the above-described first embodiment.

Further, in the medical device 1A according to the present modification, the locking portion 32 is formed to protrude over the entire circumference on the inner wall of the proximal end portion of the pressing tube 31A. Accordingly, as shown in FIG. 15A, the area of the contact surface where the stopper 36 and the pressing tube 31A come into contact with each other is larger than that of the medical device 1 according to the first embodiment. According to the medical device 1A of the present modification, the operation of moving the stopper 36 with the stopper 36 and the pressing tube 31A in contact with each other becomes simple.

Second Embodiment

Hereinafter, a clip cartridge according to a second embodiment of the present disclosure will be described with reference to FIG. 20 to FIG. 23. Hereinafter, the same configurations as those of the above-described first embodiment will be designated by the same reference numerals, the description thereof will be omitted, and the description will focus on points different from the above-described first embodiment.

Figure 20:
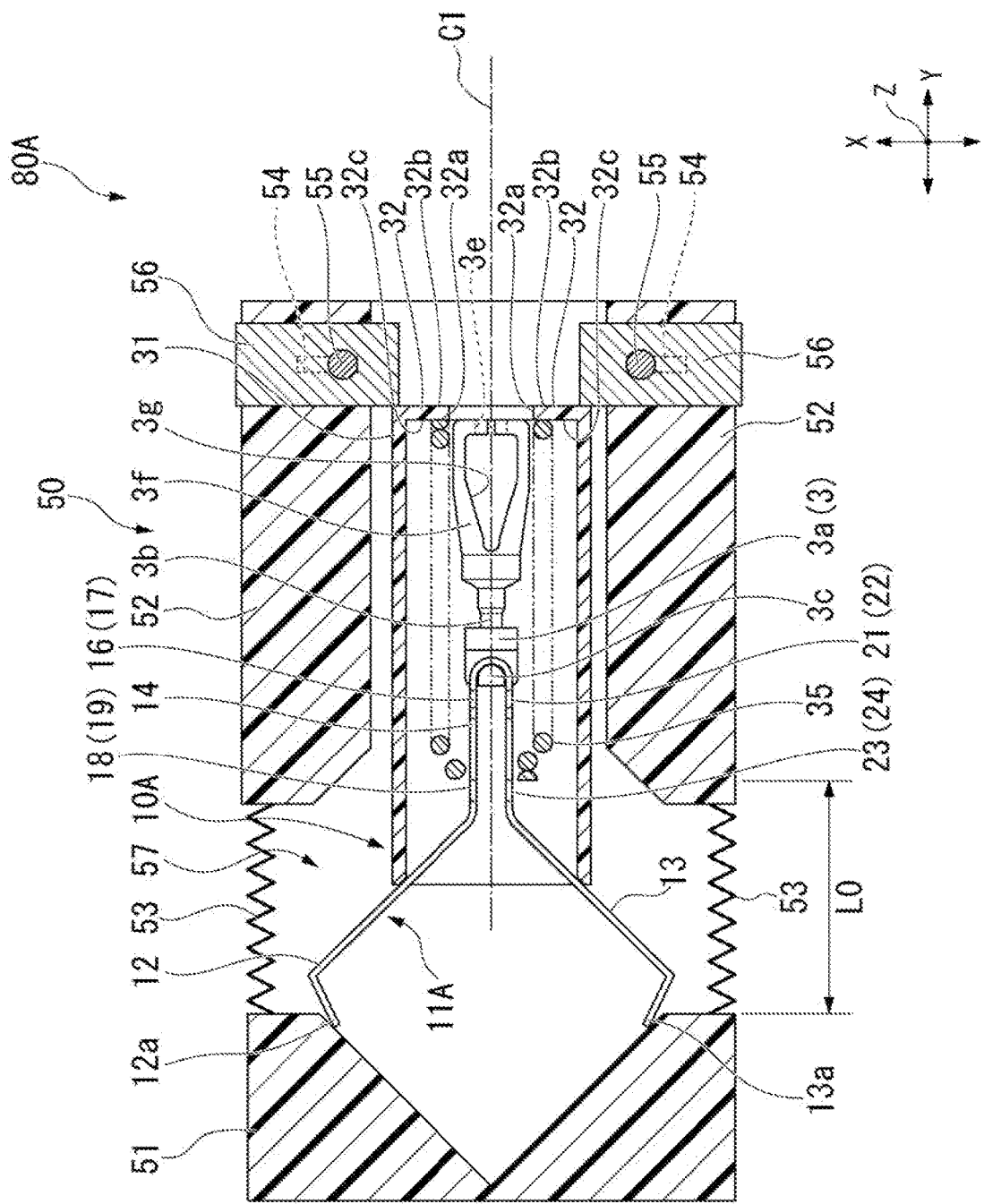
FIG. 20 is a partial cross-sectional planar view showing a state in which a clip unit is accommodated in a clip cartridge according to a second embodiment of the present disclosure.
Figure 21:
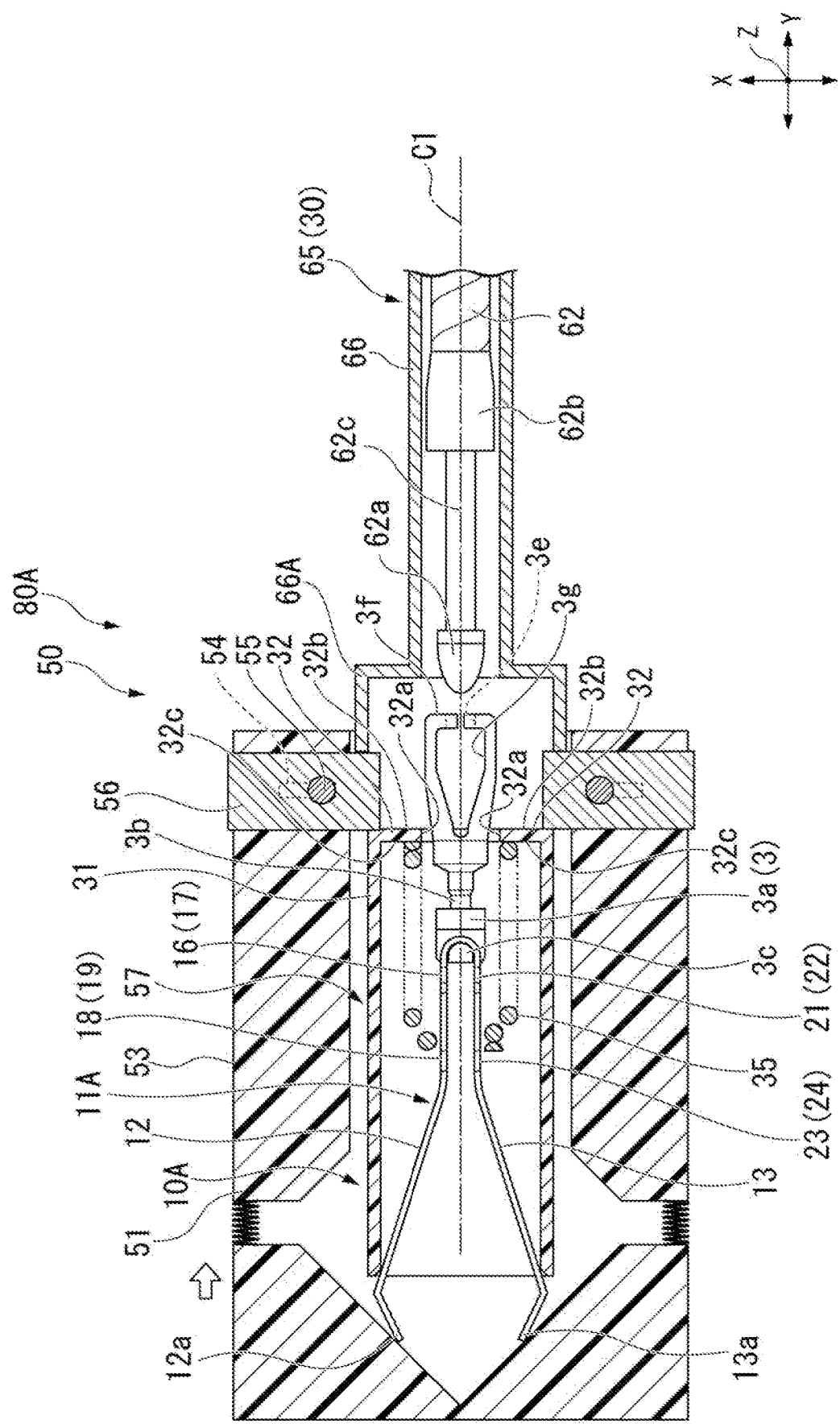
FIG. 21 is a view showing an operation of attaching the clip unit to the applicator according to the present embodiment.
Figure 22:
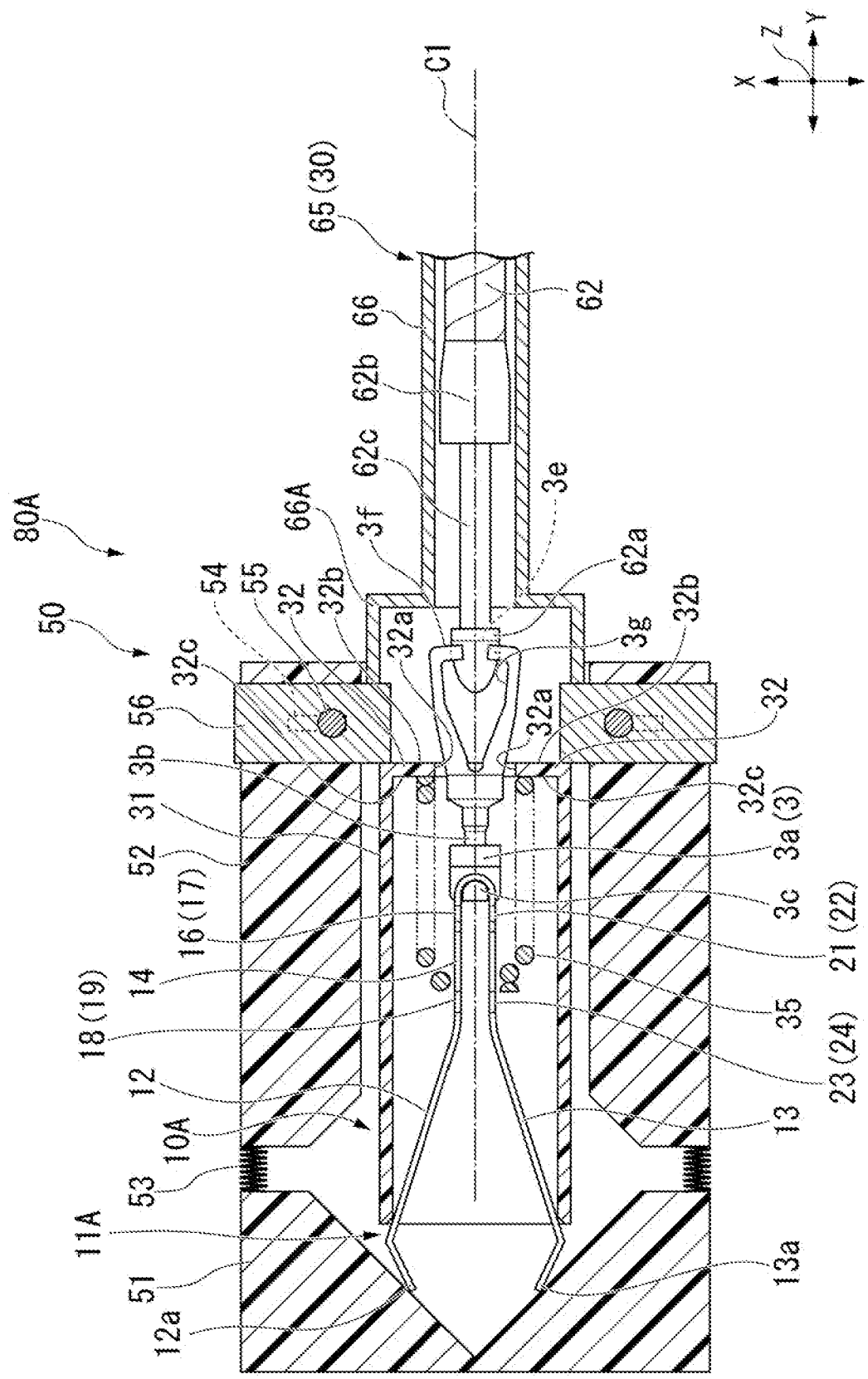
FIG. 22 is a view showing the operation of attaching the clip unit to the applicator according to the present embodiment.
Figure 23:
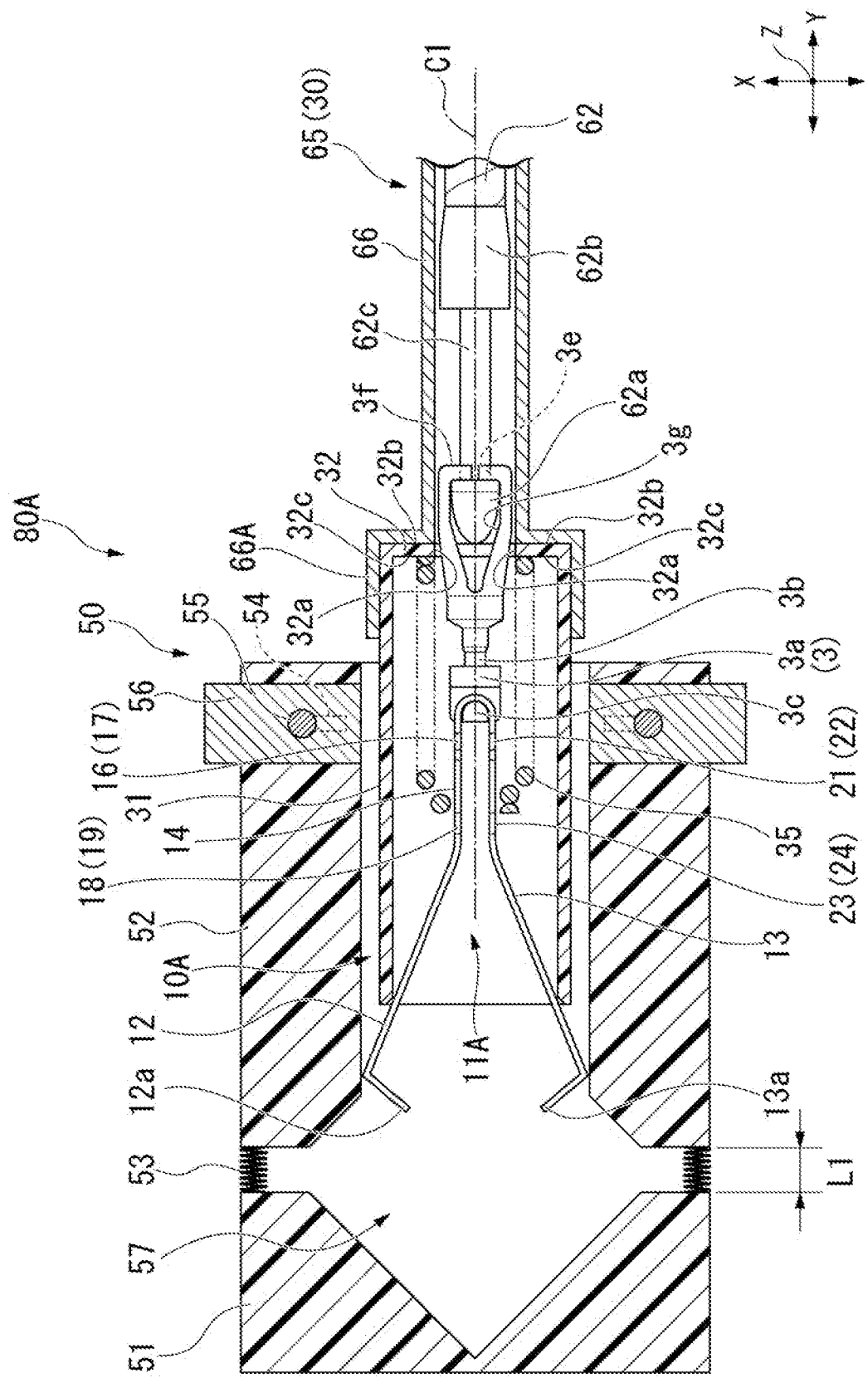
FIG. 23 is a view showing the operation of attaching the clip unit to the applicator according to the present embodiment.

FIG. 20 is a partial cross-sectional planar view showing a state where the clip 10A is accommodated in the housing 50 according to the second embodiment of the present disclosure. FIG. 21 to FIG. 23 are views showing operations of attaching the clip 10A according to the present embodiment on the applicator 30.

As shown in FIG. 20, a clip cartridge 80A according to the present embodiment is configured to have the clip 10A according to the above-described modification of the first embodiment and a housing 50. The housing 50 includes a distal-main-body portion 51, a proximal-main-body portion 52, an elastic member 53 that connects the distal-main-body portion 51 and the proximal-main-body portion 52, a vertical groove 54 formed in the proximal-main-body portion 52, and a stopper 56 integrally formed with a pin 55. According to the present embodiment, by disposing the pin 55 in the vertical groove 54, the stopper 56 may slide in the radial direction of the housing 50 along the vertical groove 54.

Similar to the above-described first embodiment, FIG. 20 to FIG. 23 are used only to show the positional relationship between the clip 10A and the housing 50. The housing 50 according to the present embodiment is not limited to the configurations shown in these figures.

As shown in FIG. 20, in a state before the clip 10A is attached to the applicator 30, the arm member 11A is accommodated in a clip accommodation portion 57 formed between the distal-main-body portion 51 and the proximal-main-body portion 52 in the housing 50, and the pressing tube 31 is disposed in the lumen 38 formed in the proximal-main-body portion 52.

As shown in FIG. 20, at the proximal end side of the proximal-main-body portion 52, a pair of stoppers 56 are provided in contact with the proximal end surface of the pressing tube 31. The pair of stoppers 56 may be moved outward in the radial direction of the housing 50 along the vertical groove 54 by the operation of the operator. When the pair of stoppers 56 moves outward in the radial direction of the housing 50 along the vertical groove 54, the engagement between the stoppers 56 and the pressing tube 31 may be released.

As shown in FIG. 20, an elastic member 53 is provided between the proximal-main-body portion 52 and the distal-main-body portion 51. The elastic member 53 may be configured using, for example, various known springs; however, the elastic member 53 is not limited to this configuration. For example, the elastic member 53 may be formed from a material that is elastically deformable to a certain extent when it receives the pressing force in the longitudinal axis direction itself.

The clip 10A and the applicator 30 according to the present embodiment have the same configurations as that in the modification of the first embodiment described above.

(Operation to Attach the Clip to the Applicator)

According to the present embodiment, when the clip 10A is attached to the applicator 30, in the state shown in FIG. 20, the operator grasps the proximal-main-body portion 52 and presses the distal-main-body portion 51 toward the proximal end side in the longitudinal axis direction of the housing 50 (direction along the axis C1). By this operation, the elastic member 53 between the distal-main-body portion 51 and the proximal-main-body portion 52 is compressed, and the distal-main-body portion 51 is moved toward the proximal end and toward the proximal-main-body portion 52.

As shown in FIG. 21, the elastic member 53 is compressed, and the distance between the distal-main-body portion 51 and the proximal-main-body portion 52 changes from L0 shown in FIG. 20 to L1 which is a value smaller than L0. On the other hand, the claws 12a, 13a provided on the distal ends of the first arm 12 and the second arm 13 of the arm member 11A of the clip 10A approach the longitudinal axis of the housing 50 along the inner wall of the clip housing 57. That is, the first arm 12 and the second arm 13 of the arm member 11A are gradually closed from the open configuration shown in FIG. 20.

According to the present embodiment, when the distal-main-body portion 51 is pressed and moves toward the proximal-main-body portion 52, the pressing force applies on the arm member 11A and the pressing tube 31. However, the pressing tube 31 is configured such that the movement of the pressing tube 31 toward the proximal end side is restricted by the stopper 56 provided at the proximal end portion of the proximal-main-body portion 52. Accordingly, the pressing force that presses the distal-main-body portion 51 applies on the arm member 11A, and the arm member 11A and the connection portion 3 that engages with the arm member 11A move to the proximal end side with respect to the pressing tube 31.

As shown in FIG. 21, the connection portion 3 is moved toward the proximal end side with respect to the pressing tube 31 such that the connection portion 3 protrudes from the opening at the proximal end side of the pressing tube 31 and the connection portion 3 is moved to the position at more proximal end side than the locking portion 32. In this state, the elastic member 35 in the pressing tube 31 is compressed. In other words, by pressing the distal-main-body portion 51 toward the proximal end side, it is possible for the connection portion 3 to transition from the accommodation configuration of being accommodated in the pressing tube 31 to the protrusion configuration of protruding from the pressing tube 31.

Subsequently, as shown in FIG. 21 and FIG. 22, similarly to the above-described modification of the first embodiment, the operator operates the operation portion (not shown) to move the support portion 66A provided at the distal end portion of the sheath 66 until coming in contact with the stopper 56. Subsequently, the operator may engage the hook 62a provided at the distal end of the operation wire 62 with the connection portion 3 protruding from the pressing tube 31 by pushing the slider of the operation portion (not shown) toward the distal end side. As shown in FIG. 22, when the hook 62a enters the notch portion 3g of the connection portion 3 to be engaged with the connection portion 3, the pair of stoppers 56 are in contact with the proximal end surface of the pressing tube 31 such that the transition of the connection portion 3 from the protrusion configuration to the accommodation configuration is restricted.

According to the present embodiment, similarly to the above-described modification of the first embodiment or the first embodiment, only in the state in which at least part of the proximal end portion 3f of the connection portion 3 is not accommodated in the pressing tube 31A and the sheath 66 and exposed to the outside (for example, positioned between the pair of stoppers 56), the operator may engage the hook 62a to the notch portion 3g of the connection portion 3.

When the operator confirms that the hook 62a engages with the connection portion 3, the operator moves the pair of stoppers 56 together with the pin 55 along the vertical groove 54 outward in the radial direction of the housing 50, as shown in FIG. 23. As a result, the engagement between the pair of stoppers 56 and the proximal end surface of the connection portion 3 is released. In other words, the restriction with respect to the transition of the connection portion 3 from the protrusion configuration to the accommodation configuration by the pair of stoppers 56 is released. Accordingly, as shown in FIG. 23, due to the elastic restoring force of the first arm 12 and the second arm 13 of the arm member 11A of the clip 10A, the pressing tube 31 is moved to the proximal end side and toward the sheath 66 until the proximal end surface of the pressing tube 31 comes in contact with the distal end surface of the sheath 66. The connection portion 3 transitions to the accommodation configuration of being accommodated in the pressing tube 31. Due to the above-described operations, the clip 10A according to the present embodiment is attached to the applicator 30.

Subsequently, similarly to the above-described modification of the first embodiment described above, the operator operates the operation unit (not shown) to remove the clip 10A and the applicator 30 from the opening at the proximal end side of the housing 50 such that it is possible to perform the ligation treatment on the target tissue T.

According to the clip cartridge 80A according to the present embodiment, if the length of the elastic member 53 of the housing 50 in the longitudinal axis direction is adjusted, the transition between the protrusion configuration and accommodation configuration of the clip 10A, and the protrusion length from the pressing tube 31 in the protrusion configuration of the clip 10A may be controlled. According to the clip cartridge 80A of the present embodiment, similarly to the above-described first embodiment and the modification, when the clip 10A is attached to the applicator 30, it is easy to cause the connection portion 3 of the clip 10A to transition from the accommodation configuration to the protrusion configuration.

Third Embodiment

Next, a clip cartridge 80B according to a third embodiment of the present disclosure will be described with reference to FIG. 24 to FIG. 27. Hereinafter, the same configurations as those of the above-described respective embodiments will be designated by the same reference numerals, the description thereof will be omitted, and the description will be focused on the points different from the above-described respective embodiments. In the present embodiment, the clip 10A and the applicator 30 have the same configurations as those of the above-described embodiments.

Figure 24:
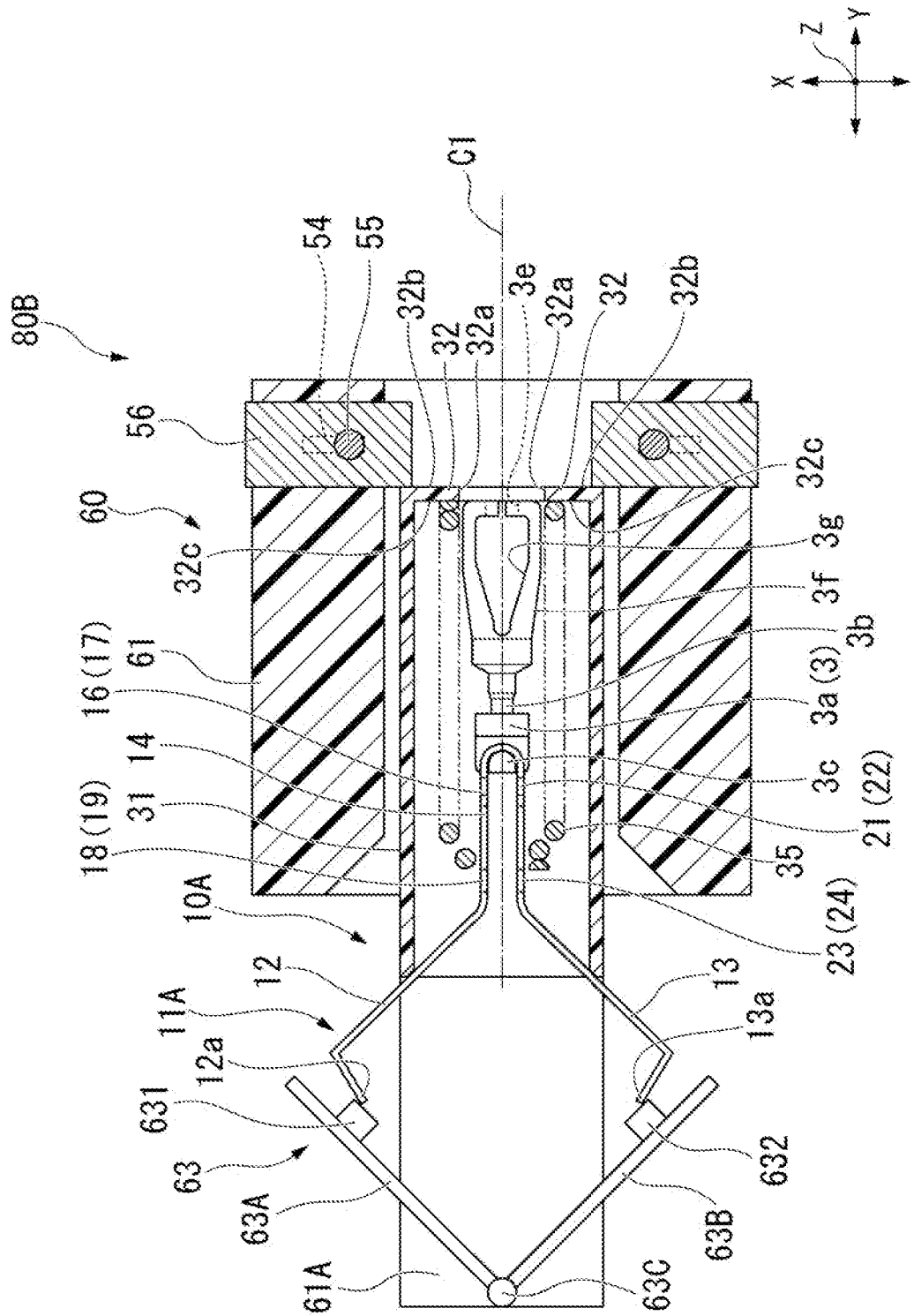
FIG. 24 is a partial cross-sectional planar view showing a state in which a clip unit is accommodated in a clip cartridge according to a third embodiment of the present disclosure.
Figure 25:
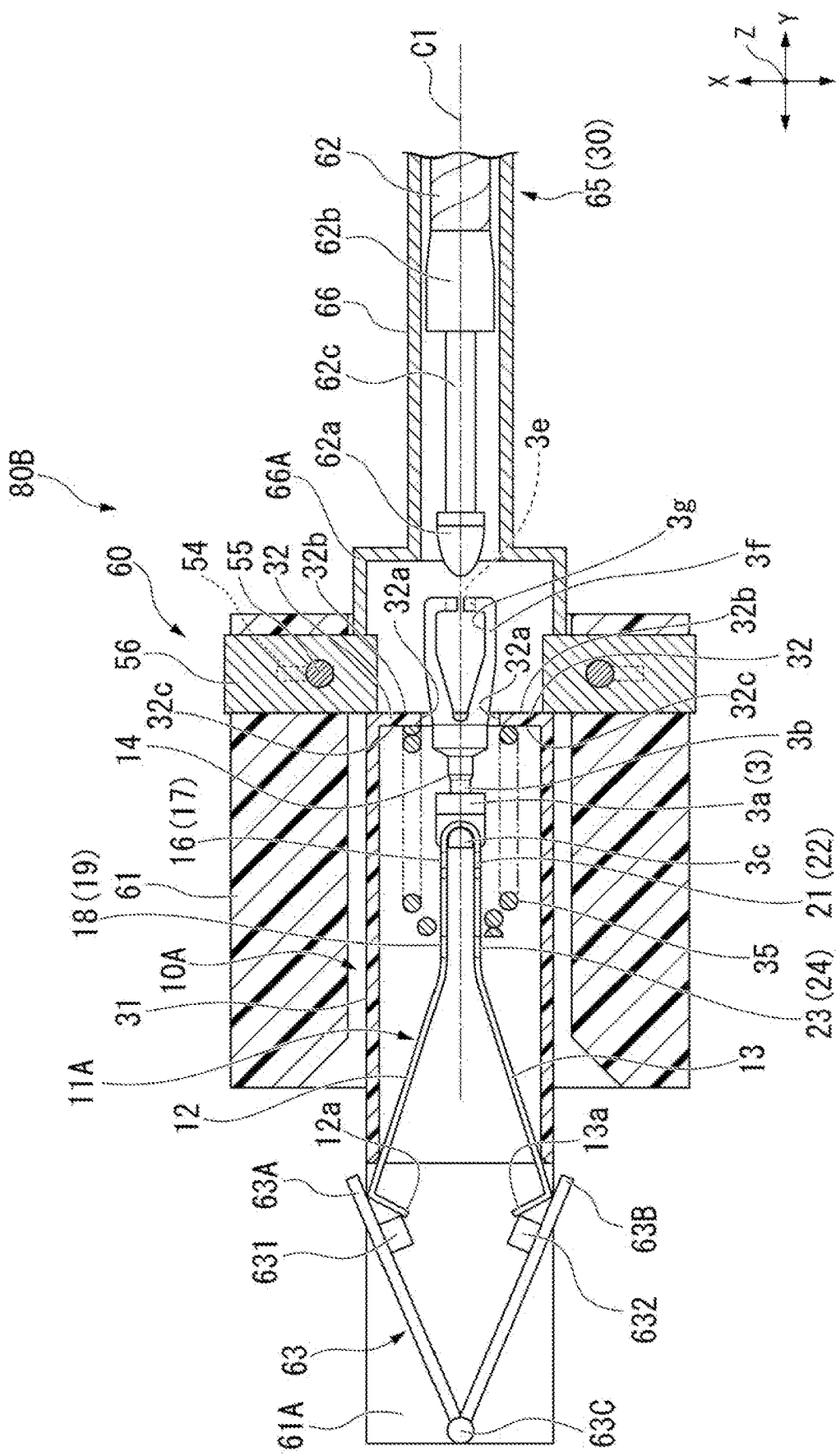
FIG. 25 is a view showing an operation of attaching the clip unit to the applicator according to the present embodiment.
Figure 26:
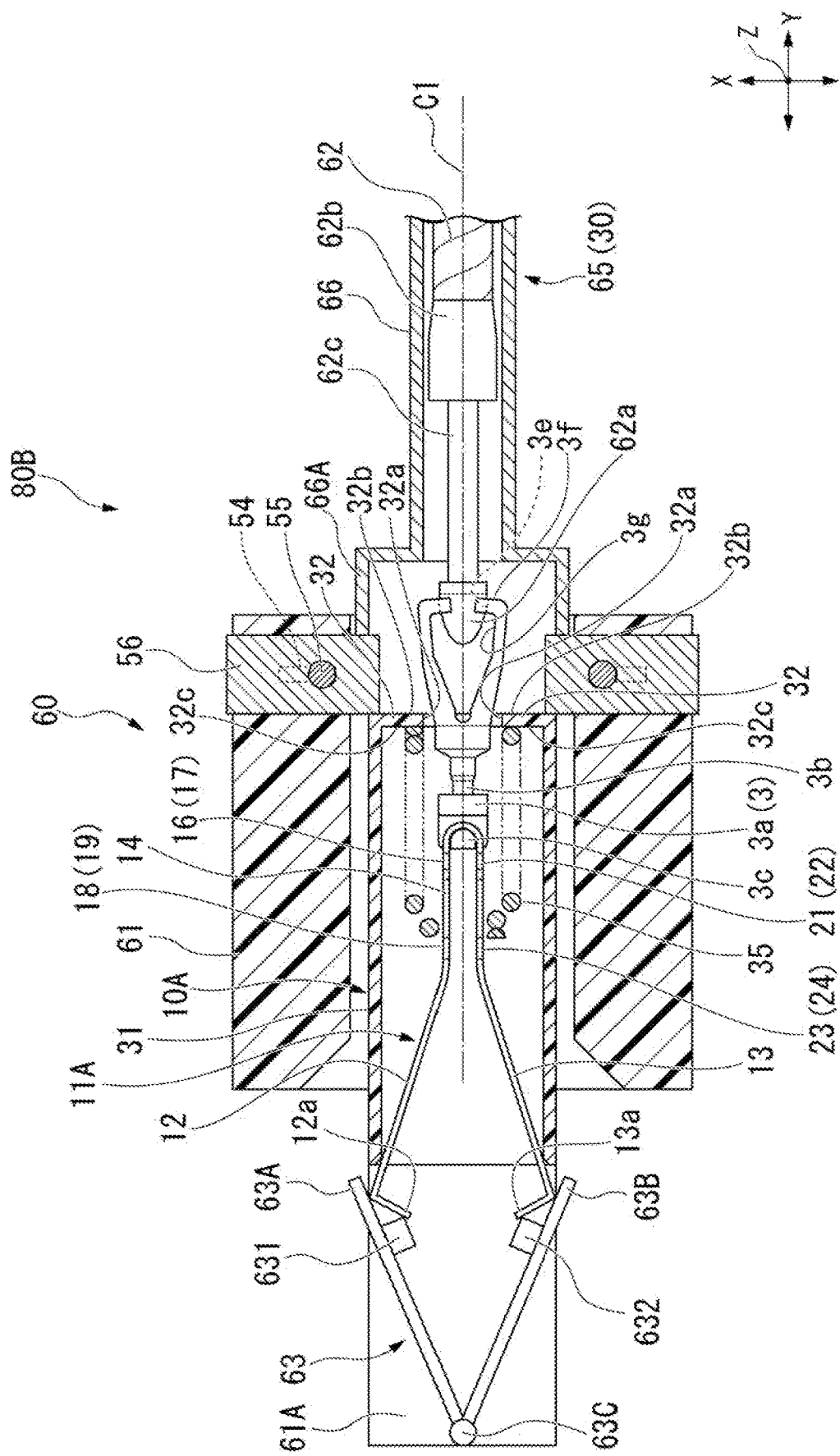
FIG. 26 is a view showing the operation of attaching the clip unit to the applicator according to the present embodiment.
Figure 27:
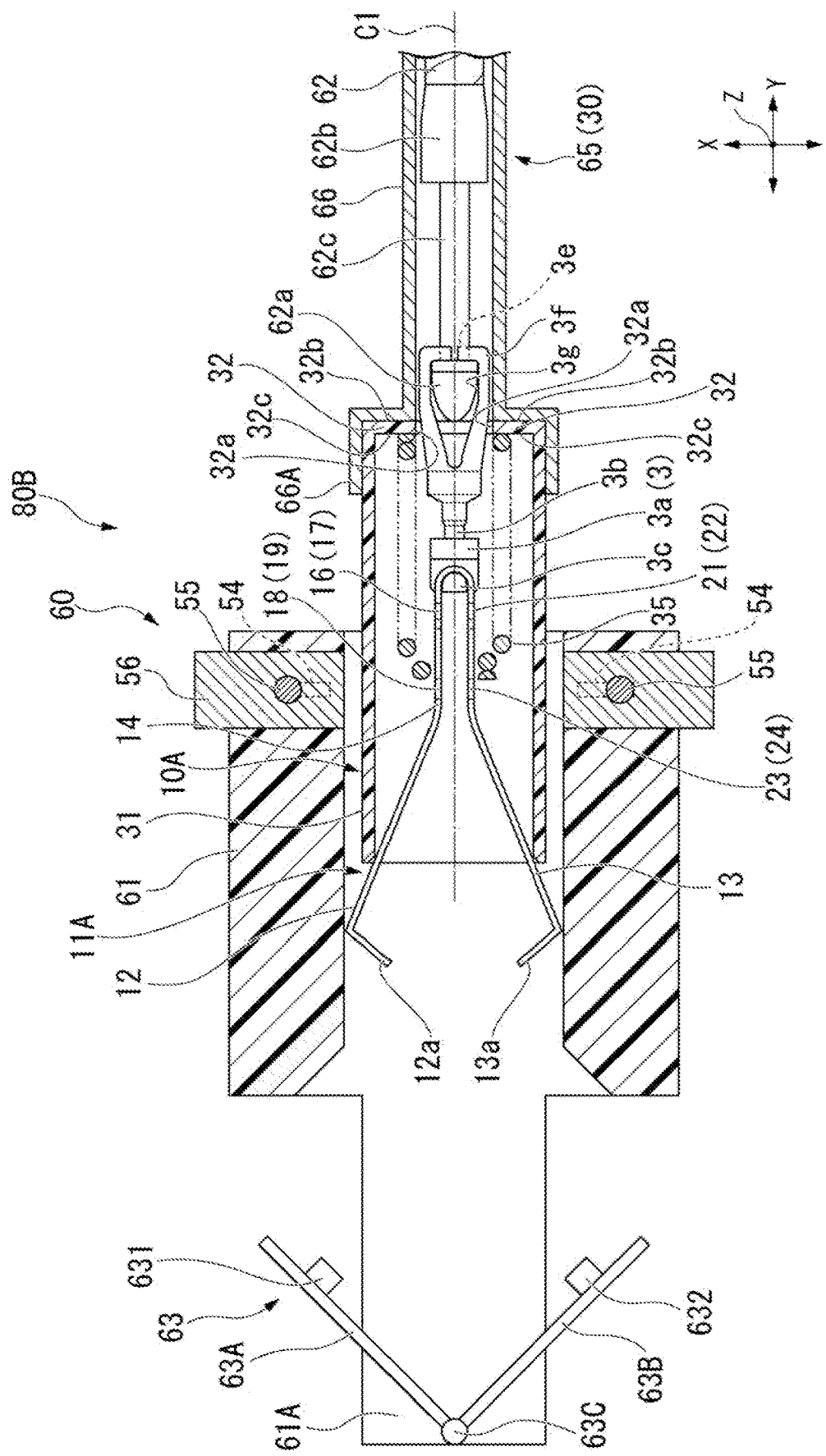
FIG. 27 is a view showing the operation of attaching the clip unit to the applicator according to the present embodiment.

FIG. 24 is a partial cross-sectional planar view showing a state where the clip 10A is housed in the housing 60 in the clip cartridge 80B according to the present embodiment. FIG. 25 to FIG. 27 are views showing operations of attaching the clip 10A according to the present embodiment to the applicator 30.

As shown in FIG. 24, in the housing 60 of the clip cartridge 80B according to the present embodiment, a protrusion 61A is provided on the distal end side of the main body 61. A control mechanism 63 configured to abut the claws 12a, 13a of the first arm 12 and the second arm 13 of the arm member 11A of the clip 10A is configured in the protrusion 61A.

According to the present embodiment, the control mechanism 63 is configured by connecting a pair of rods 63A, 63B with a pin 63C. The pair of rods 63A, 63B may rotate around the pin 63C as a rotation center. As shown in FIG. 24, the pair of rods 63A and 63B are biased by the elastic member such as a spring or the like to the direction of separating from each other. In other words, in the state in which there is no external force applied thereto, as shown in FIG. 24, the pair of rods 63A, 63B of the control mechanism 63 are separated by a certain distance in the radial direction of the housing 60.

As shown in FIG. 24, a protrusion 631 and a protrusion 632 are formed at the inner side of the pair of rods 63A, 63B of the control mechanism 63, that is, on the side facing the longitudinal axis of the housing 60. According to the present embodiment, the protrusion 631 and the protrusion 632 are formed at positions capable of coming in contact with the first arm 12 and the second arm 13 of the arm member 11A. Further, the protrusion 631 and the protrusion 632 are formed from a slip resistance material such that when the protrusion 631 and the protrusion 632 are engaged with each of the first arm 12 and the second arm 13, the engagement state may be stably maintained. According to the present embodiment, as will be described later, the portions of the first arm 12 and the second arm 13 of the arm member 11A at more proximal end side than the claws 12a, 13a may contact the protrusion 631 and the protrusion 632, respectively.

Since the control mechanism 63 has the above-described configuration, the arm member 11A may be locked without directly contacting the claw 12a of the first arm 12 and the claw 13a of the second arm 13 of the arm member 11A.

Other configurations of the housing 60 according to the present embodiment are the same as those of the housing 50 according to the second embodiment described above.

(Operation to Attach the Clip to the Applicator)

As shown in FIG. 24, in the state in which the clip 10A is accommodated in the housing 60, the claw 12a of the first arm 12 and the second claw 13a of the second arm 13 of the arm member 11A are in contact with the protrusion 631 of the rod 63A and the protrusion 632 of the rod 63B of the control mechanism 63, respectively. The arm member 11A is in the open configuration in which the first arm 12 and the second arm 13 are separated from each other. The connection portion 3 of the clip 10A is arranged in the pressing tube 31 located in the lumen 38 formed in the main body 61. Further, the pair of stoppers 56 are arranged at the positions protruding into the lumen 38 so as to come in contact with the proximal end surface of the pressing tube 31.

The operator may close the control mechanism 63 as shown in FIG. 25 by grasping and pressing the pair of rods 63A, 63B of the control mechanism 63. At this time, the first arm 12 and the second arm 13 of the arm member 11A are closed together with the control mechanism 63. In this process, the rod 63A of the control mechanism 63 comes into contact with a portion of the first arm 12 at slightly proximal end side than the claw 12a, and the arm 63B of the control mechanism 63 comes into contact with a portion of the second arm 13 at slightly proximal end side than the claw 13a. That is, the rods 63A, 63B of the control mechanism 63 do not directly apply the load to the claw 12a of the first arm 12 and the claw 13a of the second arm 13 of the arm member 11A. As a result, when the operator operates the control mechanism 63 to close the first arm 12 and the second arm 13 of the arm member 11A, it is possible to prevent the claws 12a, 13a from being unintentionally deformed.

When the operator presses and closes the control mechanism 63, the arm member 11A transitions from the open configuration to the closed configuration, and the connection portion 3 on which the intermediate portion 14 of the arm member 11A is hooked is moved toward the proximal end side along the longitudinal axis of the housing 60 (the direction along the axis C1). As a result, as shown in FIG. 25, the connection portion 3 moves toward the proximal end side with respect to the pressing tube 31, and the connection portion transitions from the accommodation configuration of being accommodated in the pressing tube 31 to the protrusion configuration of climbing over the locking portion 32 to protrude from the opening at the proximal end side of the pressing tube 31. In this state, since the proximal end surface of the pressing tube 31 is in contact with the stopper 56, the movement of the pressing tube 31 to the proximal end side is restricted. The elastic member 35 is compressed in the pressing tube 31.

Subsequently, similarly to each of the above-described embodiments, the operator operates the operation portion (not shown) to insert the applicator 30 to the housing 60 until the support portion 66A provided at the distal end portion of the sheath 66 comes in contact with the stopper 56. In the state in which the support portion 66A is in contact with the stopper 56, the operator pushes the slider of the operation portion (not shown) to move the hook 62a provided at the distal end of the operating wire 62 to the distal end side together with the operating wire 62 itself. As a result, as shown in FIG. 26, the hook 62a enters the notch portion 3g of the connection portion 3, and the hook 62a and the connection portion 3 are engaged with each other.

According to the present embodiment, similarly to the above-described each embodiment and the modification, only in the state in which at least part of the proximal end portion 3f of the connection portion 3 is not accommodated in the sheath 66 and exposed to the outside (for example, positioned between the pair of stoppers 56), the operator may engage the hook 62a with the notch portion 3g of the connection portion 3.

When it is confirmed that the hook 62a and the connection portion 3 are engaged with each other, the operator moves (slides) the pair of stoppers 56 along the vertical groove 54 outward in the radial direction of the housing 60 while grasping the control mechanism 63. By this operation, the engagement between the pressing tube 31 and the stopper 56 is released. In other words, the restriction with respect to the transition of the pressing tube 31 from the protrusion configuration to the accommodation configuration by the stopper 56 is released. As a result, due to the elastic restoring force of the first arm 12 and the second arm 13 of the arm member 11A, the pressing tube 31 moves toward the sheath 66 along the longitudinal axis direction of the housing 60 toward the proximal end side. Further, the engagement state between the control mechanism 63 and the first arm 12 and the second arm 13 of the arm member 11 is also released, and the arm member 11A and the control mechanism 63 are separated from each other.

As shown in FIG. 27, the pressing tube 31 moves to the proximal end side until the pressing tube 31 comes into contact with the support portion 66A provided at the distal end portion at the distal end of the sheath 66 such that the connection portion 3 transitions to the accommodation configuration of being accommodated in the pressing tube 31.

Subsequently, the operator operates an operation portion (not shown) to remove the applicator 30 and the clip 10A attached to the applicator 30. The operation of attaching the clip 10A to the applicator 30 according to the present embodiment is finished.

According to the clip cartridge 80B of the present embodiment, by the combination of the control mechanism 63 and the stopper 56, the transition between the protrusion configuration and the accommodation configuration of the connection portion 3 of the clip 10 and the protrusion amount of the connection portion 3 from the pressing tube 31 in the protrusion configuration may be controlled. According to the housing 60 according to the present embodiment, similarly to the above-described embodiments, at the time of attaching the clip 10A to the applicator 30, it is easy to make the connection portion 3 of the clip 10A to transition from the accommodation configuration to the protrusion configuration.

Fourth Embodiment

Hereinafter, a clip cartridge 80C according to the fourth embodiment of the present disclosure will be described with reference to FIG. 28A to FIG. 31. Hereinafter, the same configurations as those of the above-described respective embodiments will be designated by the same reference numerals, the description thereof will be omitted, and the description will be focused on the points different from the above-described respective embodiments.

Figure 28A:
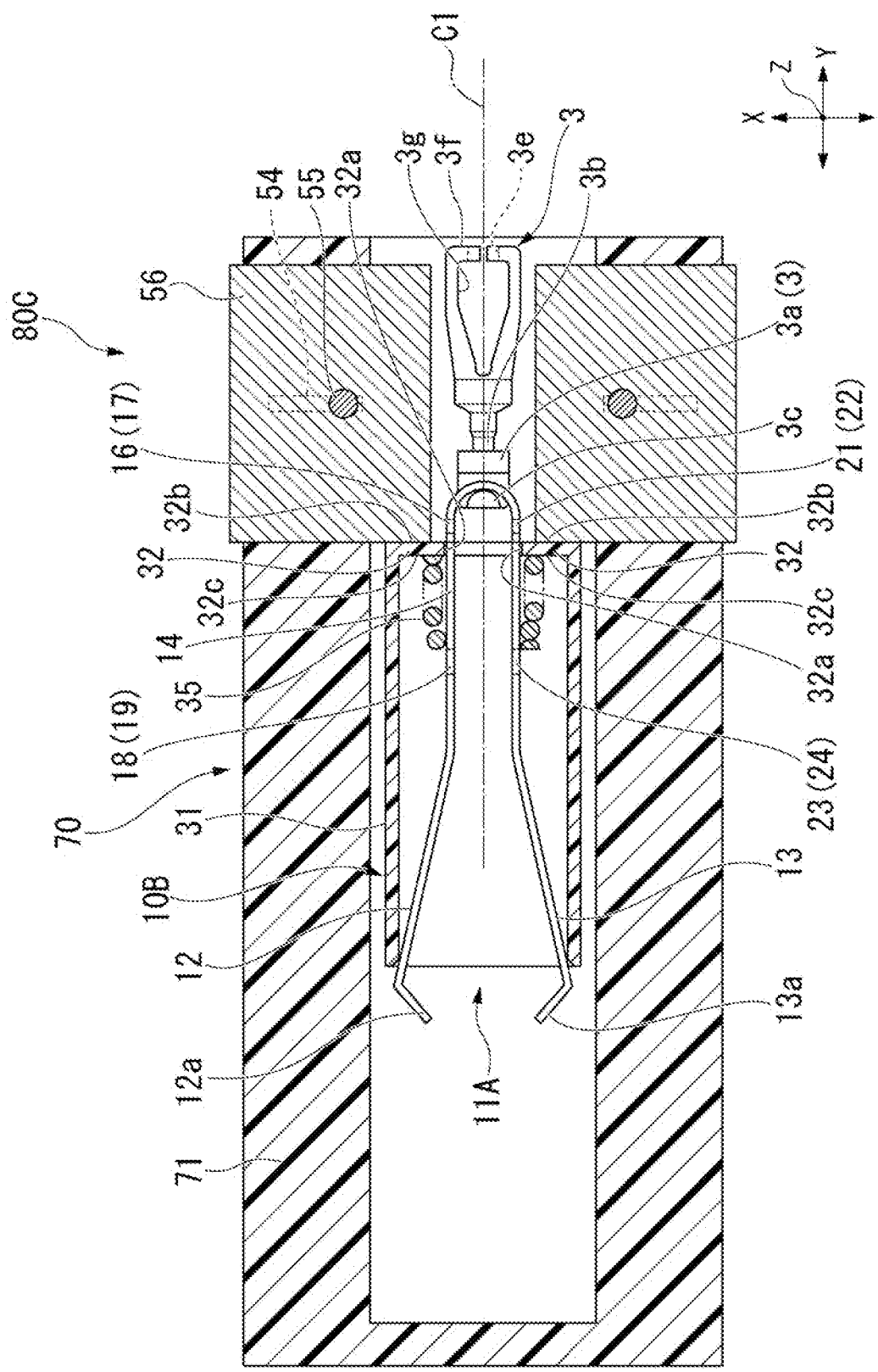
FIG. 28A is a partial cross-sectional planar view showing a state in which a clip unit is accommodated in a clip cartridge according to a fourth embodiment of the present disclosure.
Figure 28B:
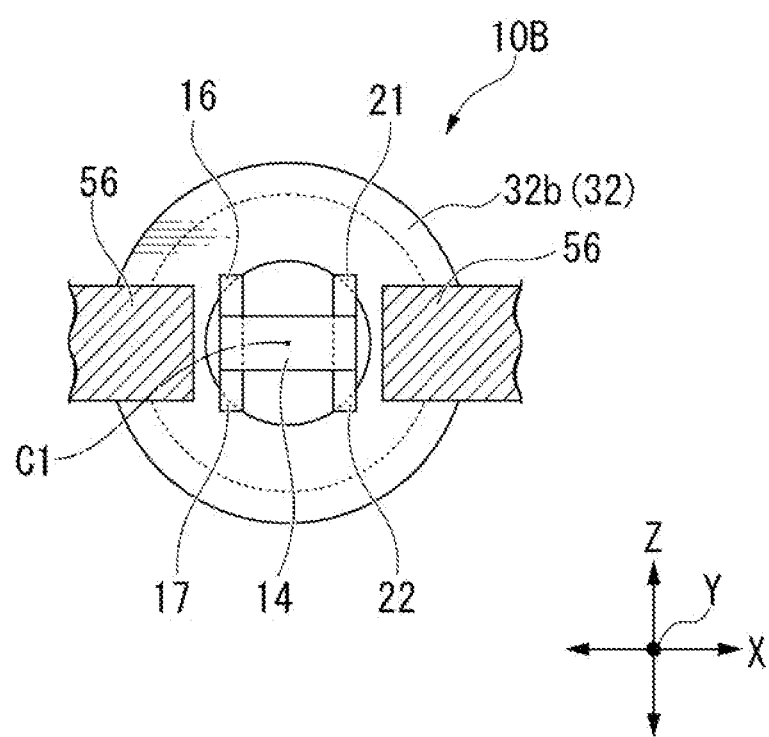
FIG. 28B is a view showing the clip unit when observed from the proximal end side in the state in which the clip unit is accommodated in the cartridge according to the present embodiment.
Figure 30:
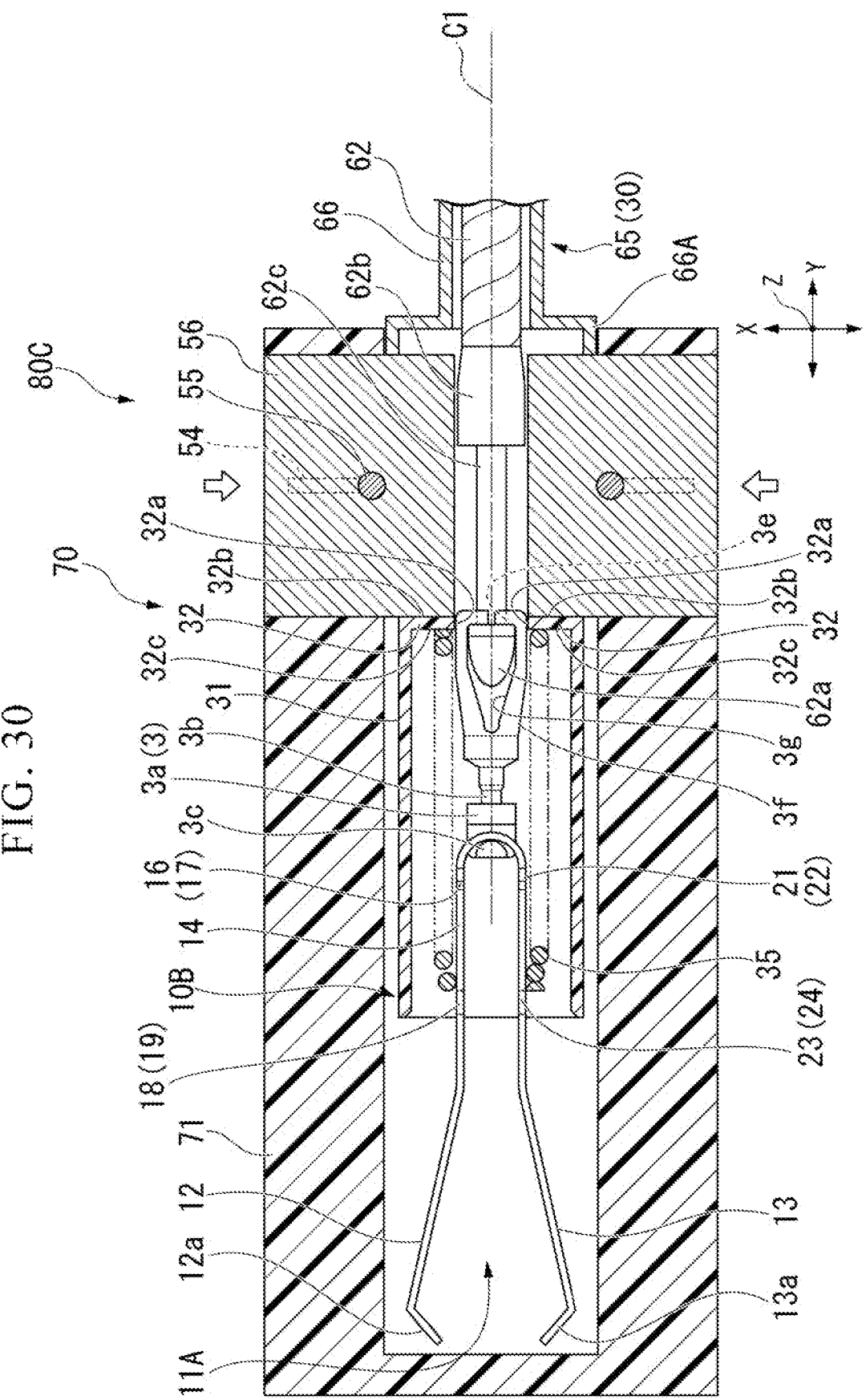
FIG. 30 is a view showing the operation of attaching the clip unit to the applicator according to the present embodiment.
Figure 31:
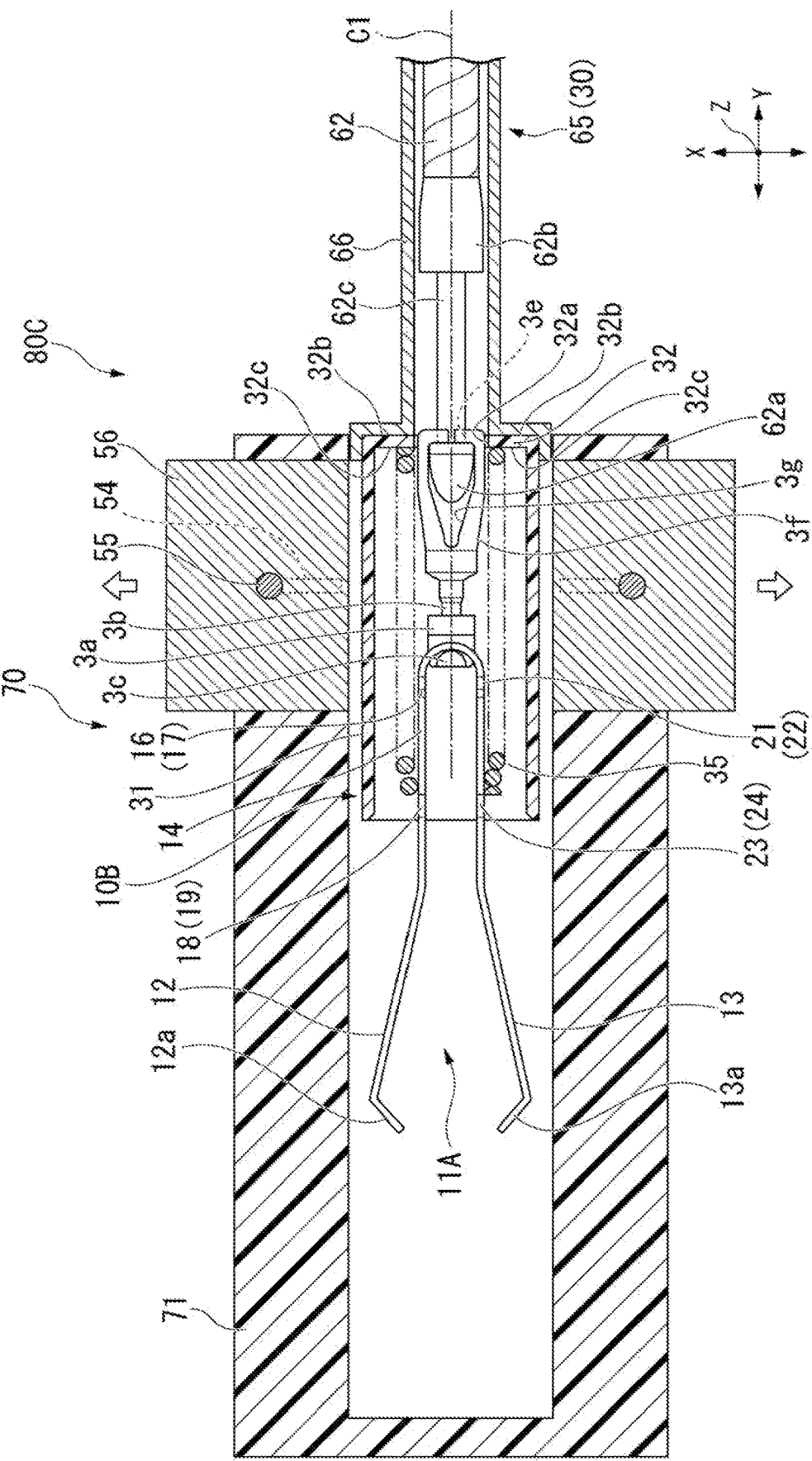
FIG. 31 is a view showing the operation of attaching the clip unit to the applicator according to the present embodiment.

FIG. 28A is a partial cross-sectional planar view showing a state in which the clip unit 10B is accommodated in the housing 70 according to the fourth embodiment of the present disclosure. FIG. 28B is a view of the clip 10B viewed from the proximal end side in a state where the clip 10B is accommodated in the clip cartridge 80C according to the present embodiment. FIG. 29 to FIG. 31 are views showing operations of attaching the clip unit 10B to the applicator 30 according to the present embodiment.

As shown in FIG. 28A and FIG. 28B, in the state in which the clip 10B according to the present embodiment is accommodated in the housing 70 of the clip cartridge 80C, the first locked portions 16, 17 and the second locked portions 21, 22 provided at the proximal end side of the arm member 11A are engaged with the proximal end surface 32b of the locking portion 32 provided at the proximal end portion of the pressing tube 31. Accordingly, the movement of the arm member 11A toward the distal end side with respect to the pressing tube 31 is restricted. As a result, the state in which the connection portion 3 connected to the arm member 11A protrudes from the opening at the proximal end side of the pressing tube 31 is maintained. In this state, the elastic member 35 is compressed inside the pressing tube 31.

In the housing 70 according to the present embodiment, similarly to the above-described embodiments, the stopper 56 and the pin 55 may be integrally moved (slided) in the radial direction of the housing 70 along the vertical groove 54 at the proximal end side of the main body portion 71. As shown in FIG. 28A, the pair of stoppers 56 abuts on the proximal end surface 32b of the locking portion 32 of the pressing tube 31 and the pair of stoppers restrict the movement of the pressing tube 31 toward the proximal end side.

According to the above-described configuration of the housing 70 according to the present embodiment, in the operation of attaching the clip 10B to the applicator 30, the operation of protruding the connection portion 3 from the opening at the proximal end side of the pressing tube 31 by the operation of the operator is unnecessary. As will be described later, according to the present embodiment, when the operator moves (slides) the stopper 56 inward in the radial direction of the housing 70, the pair of stoppers 56 abut the intermediate portion 14 of the arm member 11A, and it is possible to release the engagement between the first locked portions 16, 17 and the second locked portions 21, 22 of the arm member 11A and the proximal end surface 32b of the locking portion 32 of the pressing tube 31.

(Operation to Attach the Clip to the Applicator)

As shown in FIG. 28A and FIG. 28B, in the state in which the clip 10B according to the present embodiment is accommodated in the housing 70, the first locked portions 16, 17 and the second locked portions 21, 22 are in contact with the proximal end surface of the pressing tube 31 such that the protrusion configuration in which the connection portion 3 protrudes from the opening at the proximal end side of the pressing tube 31 is maintained. The operator operates the operation portion (not shown) to move the sheath 66 to the distal end side, as shown in FIG. 29, and causes the support portion 66A provided at the distal end portion of the sheath 66 to come into contact with the stopper 56. In this state, similarly to the above-described embodiments, the proximal end portion 3f of the connection portion 3 is located between the pair of stoppers 56 in the space inside the support portion 66A. Subsequently, the operator pushes the slider of the operation portion (not shown) to insert the hook 62a provided at the distal end of the operation wire 62 into the notch 3g of the connection portion 3 protruding from the opening at the proximal end side of the pressing tube 31.

When the operator confirms that the hook 62a is engaged with the connection portion 3, the operator grasps the pair of stoppers 56 and moves (slides) the pair of stoppers 56 inward in the radial direction of the housing 70 along the vertical groove 54. By this operation, the pair of stoppers 56 press the intermediate portion 14 of the arm member 11A inward in the radial direction of the housing 70.

Due to the pressing force by the stopper 56 inward in the radial direction of housing 70, the intermediate portion 14 of the arm member 11A is elastically deformed and the inner diameter of the loop shape formed in the intermediate portion 14 is decreased. As a result, the distance between the first locked portions 16, 17 and the second locked portions 21, 22 of the arm member 11A in the radial direction of the housing 70 is decreased. The operator moves the pair of stoppers 56, and when the distance between the first locked portions 16, 17 and the second locked portions 21, 22 of the arm member 11A is equal to or less than the inner diameter of the edge portion 32a of the locking portion 32, the engagement between the first locked portions 16, 17, the second locked portions 21, 22 and the proximal end surface 32b of the locking portion 32 of the pressing tube 31 is released (see FIG. 18C).

According to the present embodiment, when the engagement between the first engaged portions 16, 17, the second engaged portions 21, 22 and the proximal end surface 32b of the locking portion 32 is released, the elastic restoring force of the first arm 12 and the second arm 13 of the arm member 11A and the elastic restoring force of the elastic member 35 apply on the connection portion 3 to move the connection portion 3 to the distal end side. As a result, as shown in FIG. 30, the connection portion 3 transitions from the protrusion configuration of protruding from the opening at the proximal end side of the pressing tube 31 to the accommodation configuration of being accommodated in the pressing tube 31. At this time, the locking portion 32 of the pressing tube 31 and the support portion 66A of the sheath 66 are in contact with the distal end surface and the proximal end surface of the stopper 56, respectively, and the pressing tube 31 and the sheath 66 are separated from each other.

Subsequently, the operator moves (slides) the pair of stoppers 56 outward in the radial direction of the housing 70 along the vertical groove 54. As shown in FIG. 31, the engagement between the pressing tube 31 and the stopper 56, and the engagement between the sheath 66 and the stopper 56 are released. In this state, similarly to the above-described embodiments, the elastic restoring force of the first arm 12 and the second arm 13 of the arm member 11A applies on the pressing tube 31, and the pressing tube 31 and the sheath 66 are engaged with each other.

The operator operates the operation portion (not shown) to remove the clip 10B attached to the applicator 30 together with the applicator 30 from the housing 70. The operations to attach the clip 10B to the applicator 30 according to the present embodiment is finished.

According to the clip cartridge 80C of the present embodiment, similarly to the above-described embodiments, when the clip 10B is attached the applicator 30, it is easy to cause the connection portion 3 of the clip 10B to transition from the accommodation configuration to the protrusion configuration.

According to the clip cartridge 80C of the present embodiment, by the first locked portions 16, 17 and the second locked portions 21, 22 provided on the arm member 11A of the clip 10B, when the clip 10B is accommodated in the housing 70, the protrusion configuration that the connection portion 3 protrudes from the opening on the proximal end side of the pressing tube 31 is maintained. Accordingly, the operation by the operator to protrude the connection portion 3 from the opening on the proximal end side of the pressing tube 31 is unnecessary and the attachment operation of the clip 10B becomes simple.

Although the respective embodiments and modifications of the present disclosure have been described above, the technical scope of the present disclosure is not limited to the above-described embodiments, and the configurations of the respective embodiments and modifications within the scope not departing from the spirit of the present disclosure. It is possible to change the combination of elements, make various changes to each constituent element, and delete the constituent element. The present disclosure is not limited by the above description, and only limited by the appended claims.

Figure 32:
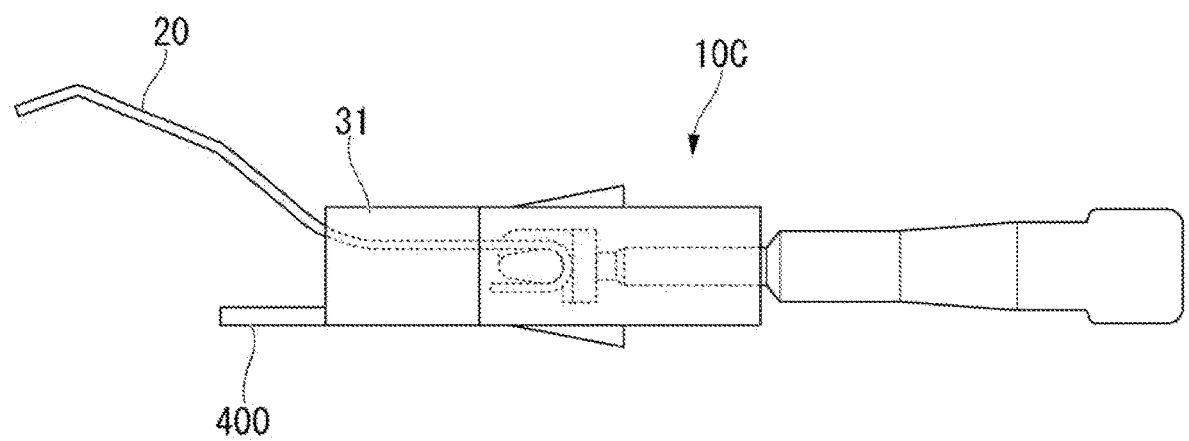
FIG. 32 is a view showing a configuration of a clip unit according to a modification of the present disclosure.

In each of the above-described embodiments, the configuration example of the arm member including the pair of arms has been described; however, the present disclosure is not limited to this configuration. For example, as shown in FIG. 32, the configuration of the clip unit including only one arm 20 is applicable. As shown in FIG. 32, the clip 10C has a rod-shaped member 400 fixed to the distal end surface of the pressing tube 31 and the rod-shaped member 400 protrudes from the distal end surface of the pressing tube 31 toward the distal end side.

According to the clip 10C configured as described above, by operating the operation wire (not shown), the arm 20 advances and retracts together with the operation wire in a state in which the arm 20 is in contact with the distal end surface of the pressing tube 31. For example, when the operator retracts the operation wire to the proximal end side, the arm 20 connected to the operation wire is retracted toward the proximal end side together with the operation wire while contacting the distal end surface of the pressing tube 31. As a result, the distance between the arm 20 and the rod-shaped member 400 decreases as the arm 20 is retracted.

In other words, in the clip 10C shown in FIG. 32, when the arm 20 and the rod-shaped member 400 are regarded as the first arm and the second arm of the arm member according to the above-described embodiments, respectively, only the arm (first arm) 20 is moved to the proximal end side with respect to the pressing tube 31, it is possible to cause the arm member to transition from the open configuration to the closed configuration. Similarly, according to the clip shown as FIG. 32, the operator pushes the operation wire toward the distal end side such that only the arm (first arm) 20 is moved to the distal end side with respect to the pressing tube 31, it is possible to cause the arm member to transition from the closed configuration to the open configuration.

In the clip 10C, since only the arm 20 may move with respect to the pressing tube 31, the arm 20 may be regarded as the movement portion of the arm member. By applying the configuration of the clip 10C shown in FIG. 32 to each of the above-described embodiments and modifications, the same effect can be achieved.

In each of the above-described embodiments and modified examples, the example has been described in which the connection portion and the arm member of the clip are formed individually and connected with each other while being separable has been described; however, the present disclosure is not limited to this configuration. For example, the connection portion may be configured as a part of the arm member. In other words, the connection portion may be integrally formed with the arm member. At this time, the operating wire may directly engages with the connection portion formed at the proximal end side of the arm member so as to connect the clip and the applicator.

What is claimed is:
1. A clip cartridge, comprising:
a clip unit including:
a tube extending along a longitudinal axis;
at least one arm inserted into the tube; and
a connection portion provided on the at least one arm and configured to transition between a protrusion configuration and an accommodation configuration, wherein the connection portion protrudes from the tube in the protrusion configuration, wherein the connection portion is accommodated in the tube in the accommodation configuration; and a housing configured to accommodate the clip unit, the housing including:
a stopper configured to restrict a transition of the connection portion from the protrusion configuration to the accommodation configuration by contacting the at least one arm or the tube; and
a groove configured to receive a biasing force via the stopper to allow the transition of the connection portion from the protrusion configuration to the accommodation configuration, wherein the biasing force is partially generated by the at least one arm biasing the tube proximal relative to the at least one arm.

2. The clip cartridge according to claim 1, wherein: the biasing force is partially generated by an elastic member provided in the tube.

3. The clip cartridge according to claim 1, wherein:
the arm the at least one arm includes an engaging portion configured to restrict movement of the at least one arm relative to the tube by engagement of the engaging portion with an engaged portion on the tube when the at least one arm is in a closed state, and
the engaging portion is configured to disengage from the engaged portion when the connection portion transitions from the protrusion configuration to the accommodation configuration.

4. The clip cartridge according to claim 1, wherein the stopper is configured to cause the connection portion to transition from the accommodation configuration to the protrusion configuration by contacting one of the at least one arm or the tube.

5. The clip cartridge according to claim 1, wherein the groove is configured to permit movement of the stopper in a direction intersecting with the longitudinal axis of the tube.

6. A medical device, comprising:
the clip cartridge according to claim 1; and
an applicator including an operation wire configured to engage with the connecting portion, wherein:
in an engagement configuration, the connection portion is engaged with the operation wire, and in a release configuration, the connection portion and the operation wire are disengaged;
the connection portion is configured to transition from the release configuration to the engagement configuration in the protrusion configuration, and
a transition of the connection portion from the release configuration to the engagement configuration in the accommodation configuration is restricted by an inner wall of the tube.

7. The clip cartridge according to claim 1, wherein the groove extends along the longitudinal axis of the tube and a direction intersecting the longitudinal axis.

8. The clip cartridge according to claim 7, wherein the groove comprises:
a first surface extending along the longitudinal axis; and
a second surface extending along the direction intersecting the longitudinal axis.

9. The clip cartridge according to claim 8, wherein the stopper is configured to move along the first surface and the second surface.

10. The clip cartridge according to claim 8, wherein the second surface is provided distally relative to the first surface.

11. The clip cartridge according to claim 8, the first surface is provided closer to the clip unit than the second surface.

12. The clip cartridge according to claim 1, wherein the stopper comprises a first stopper and a second stopper,
the first and the second stoppers are configured to move together along the longitudinal axis of the tube to transition from the accommodation configuration to the protrusion configuration.

13. The clip cartridge according to claim 12, wherein the first and the second stoppers are configured to:
move away from each other in an opposite direction intersecting the longitudinal axis to release the tube from the housing.

14. The clip cartridge according to claim 12, wherein the groove comprises a first groove and a second groove,
the first groove comprises:
a first surface extending along the longitudinal axis;
a second surface extending along a direction intersecting the longitudinal axis;
the second groove comprises:
a third surface extending along the longitudinal axis, the third surface provided on an opposite side of the first surface with respect to the longitudinal axis; and
a fourth surface extending along the direction intersecting the longitudinal axis, and the fourth surface provided on an opposite side of the first surface with respect to the longitudinal axis.

15. The clip cartridge according to claim 14, wherein the first stopper is configured to move along the first surface and the second surface, and
the second stopper is configured to move along the third surface and the fourth surface.

16. The clip cartridge according to claim 1, wherein when the stopper moves the tube distally and when the connection portion transitions from the accommodation configuration to the protrusion configuration, the tube and the at least one arm move distally relative to the housing.

17. The clip cartridge according to claim 1, wherein when the stopper moves the tube distally and when the at least one arm contacts an inner surface of the housing, the tube moves distally relative to the at least one arm.

18. The clip cartridge according to claim 1, wherein the stopper is provided proximally relative to the tube.

19. The clip cartridge according to claim 18, wherein the stopper is configured to contact a proximal end of the tube.

20. The clip cartridge according to claim 1, wherein when the stopper moves away from the tube to release the tube from the housing, the connection portion transitions from the protrusion configuration to the accommodation configuration.

* * * * *